(12) United States Patent
Chiang et al.

(10) Patent No.: US 10,617,752 B2
(45) Date of Patent: Apr. 14, 2020

(54) INACTIVATED CANINE INFLUENZA VACCINES AND METHODS OF MAKING AND USES THEREOF

(71) Applicant: BOEHRINGER INGELHEIM ANIMAL HEALTH USA INC., Duluth, GA (US)

(72) Inventors: Yu-Wei Chiang, Athen, GA (US); David Cureton, Alpharetta, GA (US); Herve Poulet, Sainte Foy-les Lyon (FR)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 15/846,735

(22) PCT Filed: Jun. 23, 2016

(86) PCT No.: PCT/US2016/038944
§ 371 (c)(1),
(2) Date: Dec. 19, 2017

(87) PCT Pub. No.: WO2016/210083
PCT Pub. Date: Dec. 29, 2016

(65) Prior Publication Data
US 2018/0250382 A1 Sep. 6, 2018

Related U.S. Application Data

(60) Provisional application No. 62/298,285, filed on Feb. 22, 2016, provisional application No. 62/185,266, filed on Jun. 26, 2015.

(51) Int. Cl.
| | | |
|---|---|---|
| *A61K 39/145* | (2006.01) | |
| *A61P 31/16* | (2006.01) | |
| *G01N 33/569* | (2006.01) | |
| *A61K 39/12* | (2006.01) | |
| *A61K 39/00* | (2006.01) | |

(52) U.S. Cl.
CPC .......... *A61K 39/145* (2013.01); *A61K 39/12* (2013.01); *A61P 31/16* (2018.01); *G01N 33/56983* (2013.01); *A61K 2039/5252* (2013.01); *A61K 2039/552* (2013.01); *A61K 2039/55505* (2013.01); *A61K 2039/55566* (2013.01); *A61K 2039/70* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 2008/0075736 A1* | 3/2008 | Crawford | A61K 39/145 424/186.1 |
| 2010/0285063 A1 | 11/2010 | Cho et al. | |
| 2014/0286979 A1 | 9/2014 | Li et al. | |
| 2018/0250382 A1* | 9/2018 | Chiang | A61K 39/145 |

FOREIGN PATENT DOCUMENTS

| | | |
|---|---|---|
| AU | 2013 205112 B2 | 4/2013 |
| KR | 20140129821 A | 11/2014 |

OTHER PUBLICATIONS

Weber et al. (Journal of Infection. 2008; 57: 361-373).*
Alignment of SEQ ID No. 31 with UniProt db access No. A0A088LHI2_9INFA Nov. 2014 by Dalziel et al.*
Alignment of SEQ ID No. 35 with UniProt db access No. A0A088LUP3_9INFA Nov. 2014 by Dalziel et al.*
Alignment of SEQ ID No. 39 with UniProt db access No. I6YLA9_9INFA Oct. 2012 by Pecoraro et al.*
Alignment of SEQ ID No. 33 with UniProt db access No. A0A088LI04_9INFA Nov. 2014 by Dalziel et al.*
Alignment of SEQ ID No. 37 with UniProt db access No. A0A088LIO4_9INFA Nov. 2014 by Dalziel et al.*
Alignment of SEQ ID No. 41 with UniProt db access No. E9P782_9INFA by Bennett et al Apr. 2011.*
Voorhees et al. (Emerging Infectious Diseases. Dec. 2017; 23 (12): 1950-1957).*
Hanson et al. ("Canine Influenza" Sep. 2016; Clinicians Brief, University of Georgia: 97-103).*
Song et al. (Journal of General Virology. 2011; 92: 2350-2355).*
Alignment of SEQ ID No. 1 with GenEmbl db access No. KC755906 by Jeoung et al Jun. 2013.*
Alignment of SEQ ID No. 2 with UniProt db access No. A0A0A7HMJ2_9INFA by Kim et al Mar. 2015.*
Alignment of SEQ ID No. 3 with GenEmbl db access No. KC755906 by Jeoung et al Jun. 2013.*
Alignment of SEQ ID No. 3 with GenEmbl db access No. KT002536 by Killian et al Jun. 2, 2015.*
Alignment of SEQ ID No. 4 with UniProt db access No. A0A0A7HMJ2_9INFA by Kim et al Mar. 2015.*
Alignment of SEQ ID No. 5 with GenEmbl db access No. KC755906 by Jeoung et al Jun. 2013.*

(Continued)

*Primary Examiner* — Shanon A. Foley
(74) *Attorney, Agent, or Firm* — Judy Jarecki-Black; Suzanne Shope

(57) ABSTRACT

The present invention relates to canine influenza virus strains, and vaccines and compositions. The present invention also relates to reagents and methods allowing their detection, methods of vaccination as well as methods of producing these reagents and vaccines.

13 Claims, 21 Drawing Sheets
Specification includes a Sequence Listing.

(56) References Cited

OTHER PUBLICATIONS

Alignment of SEQ ID No. 5 with GenEmbl db access No. KT002536 by Killian et al Jun. 2, 2015.*
Alignment of SEQ ID No. 6 with Geneseq db access No. AZP37098 by Li et al Jan. 2012.*
Alignment of SEQ ID No. 6 with UniProt db access No. A0A0A7HMJ2_9INFA by Kim et al Mar. 2015.*
Alignment of SEQ ID No. 7 with GenEmbl db access No. KT002536 by Killian et al Jun. 2, 2015.*
Alignment of SEQ ID No. 8 with UniProt db access No. R9QHN7_9INFA by Wang et al Sep. 2013.*
Alignment of SEQ ID No. 9 with GenEmbl db access No. KT002536 by Killian et al Jun. 2, 2015.*
Alignment of SEQ ID No. 10 with UniProt db access No. R9QHN7_9INFA by Wang et al Sep. 2013.*
Alignment of SEQ ID No. 11 with GenEmbl db access No. KT002536 by Killian et al Jun. 2, 2015.*
Alignment of SEQ ID No. 12 with UniProt db access No. R9QHN7_9INFA by Wang et al Sep. 2013.*
Lee et al. (Veterinary Microbiology. 2010; 143: 184-188).*
Song et al. (Emerg. Infect. Dis., 2008, 14: 741-746).
Li et al. (Infection, Genetics and Evolution, 2010; 10(8): 1286-1288).
PCT International Search Report (ISR) for related PCT/US2016/038944 dated Jan. 10, 2017.
Database UniProt; Mar. 4, 2015; accession No. A0A0A7HMJ2; XP-002764213 (ISR D2).
IDatabase UniProt; May 29, 2013: accession No. M4YR12; XP-002764214 (ISR D3).
Database UniProt; Sep. 18, 2013; accession No. R9QHN7; XP-002764215 (ISR D4).
Database UniProt; Apr. 7, 2013; accession No. KC755906; XP-002764216 (ISR D5).
Database UniProt; Dec. 15, 2014; accession No. KP137812; XP-002764217 (ISR D6).
N. N.("FAQ about the H3N2 strain of canine influenza" Apr. 14, 2015, p. 2PP, XP055319437, retrieved from the internet: URL: https://ahdc.vet.cornell.edu/docs/H3N2_FAQ_041415.pdf [retrieved on Nov. 15, 2016] (ISR D7).
Anonymous: "Update on H3N2 Canine influenza (Dog Flu) Virus: News (Flu): CDC", Apr. 28, 2015, p. 1, XP055319460, retrieved from the Internet: URL: https://www.cdc.gov/flu/news/canine-influenza-sequencing.htm [retrieved on Nov. 15, 2016] (ISR D8).
Young Kang et al. "H3N2 canine influenza virus causes severe morbidity in dogs with induction of genes related to inflammation and apoptosis", Veterinary Research, vol. 4, No. 1, 92, Jan. 1, 2013, pp. 1-12 (ISR D10).
Database UniProt; Jun. 30, 2015; accession No. KT002538; XP-002764218 (ISR D11).
David K Cureton: "An Inactivated H3N2 Canine Influenza Virus (CIV) Vaccine Aids in the Prevention of Clinical Disease and Virus Shedding in Dogs Challenged with Virulent H3N2 C", Intern J Appl Res Vet Med, vol. 14, No. 2, Jan. 2016, pp. 128-134. (ISR D12).
Merck Animal Health: "Merck Animal Health Pioneers H3N2 Canine Influenza Vaccine", Nov. 20, 2015 pp. 5PP (ISR D13).

\* cited by examiner

Figure 1A

| SEQ ID NO: | Type | Gene Description |
|---|---|---|
| 1 | DNA | DNA encoding HA protein from #4 isolate (in eggs) of H3N2 CIV |
| 2 | Protein | HA protein from #4 isolate (in eggs) of H3N2 CIV |
| 3 | DNA | DNA encoding HA protein from #4 isolate (in MDCK cells) of H3N2 CIV |
| 4 | Protein | HA protein from #4 isolate (in MDCK cells) of H3N2 CIV |
| 5 | DNA | DNA encoding HA protein from #8 isolate (in eggs) of H3N2 CIV |
| 6 | Protein | HA protein from #8 isolate (in eggs) of H3N2 CIV |
| 7 | DNA | DNA encoding NA protein from #4 isolate (in eggs) of H3N2 CIV |
| 8 | Protein | NA protein from #4 isolate (in eggs) of H3N2 CIV |
| 9 | DNA | DNA encoding NA protein from #4 isolate (in MDCK cells) of H3N2 CIV |
| 10 | Protein | NA protein from #4 isolate (in MDCK cells) of H3N2 CIV |
| 11 | DNA | DNA encoding NA protein from #8 isolate (in eggs) of H3N2 CIV |
| 12 | Protein | NA protein from #8 isolate (in eggs) of H3N2 CIV |
| 13 | oligo | H3N2 NA FWD: 5'-GGG ACC ACG CTG AAC AAT AA-3' |
| 14 | oligo | H3N2 NA REV: 5'-TGA AAC GGA ACA CCC AAC TC -3' |
| 15 | oligo | H3N8 NA FWD: 5'-GTT CGC CCT CAG AAT GTA GAA-3' |
| 16 | oligo | H3N8 NA REV: 5'-CCT ATA CGG ACT TCG ATC CTT TAT T-3' |
| 17 | oligo | Ca.H3N2.HA.390R |
| 18 | oligo | Ca.H3N2.HA.259F |
| 19 | oligo | Ca.H3N2.HA.743F |
| 20 | oligo | Ca.H3N2.HA.1276F |
| 21 | oligo | Ca.H3N2.HA.1569F |
| 22 | oligo | Ca.H3N2.HA.871R |
| 23 | oligo | Ca.H3N2.HA.1408R |
| 24 | oligo | Ca.H3N2.NA.429F |
| 25 | oligo | Ca.H3N2.NA.484R |
| 26 | oligo | Ca.H3N2.NA.975F |
| 27 | oligo | Ca.H3N2.NA.1023R |
| 28 | oligo | Ca.H3N2.1229F |
| 29 | oligo | Ca.H3N2.1279R |

Figure 1B

| SEQ ID NO: | type | Gene Description |
|---|---|---|
| 30 | DNA | DNA encoding HA protein of H3N8 CIV strain A/Ca/CT/85863/11 (GenBank KM359807.1) |
| 31 | protein | HA protein of H3N8 CIV strain A/Ca/CT/85863/11 (GenBank AIN25426.1) |
| 32 | DNA | DNA encoding NA protein of H3N8 CIV strain A/Ca/CT/85863/11 |
| 33 | protein | NA protein of H3N8 CIV strain A/Ca/CT/85863/11 |
| 34 | DNA | DNA encoding HA protein of H3N8 CIV strain A/canine/NY/120106.2/2011 (GenBank KM359803.1) |
| 35 | protein | HA protein of H3N8 CIV strain A/canine/NY/120106.2/2011 (GenBank AIN25422.1) |
| 36 | DNA | DNA encoding NA protein of H3N8 CIV strain A/canine/NY/120106.2/2011 (GenBank KM359831.1) |
| 37 | protein | NA protein of H3N8 CIV strain A/canine/NY/120106.2/2011 (GenBank AIN25464.1) |
| 38 | DNA | DNA encoding HA protein of H3N8 CIV strain WY/86033/07 |
| 39 | protein | HA protein of H3N8 CIV strain WY/86033/07 |
| 40 | DNA | DNA encoding NA protein of H3N8 CIV strain WY/86033/07 |
| 41 | protein | NA protein of H3N8 CIV strain WY/86033/07 |
| 42 | DNA | DNA encoding NA protein (SEQ ID NO:37) of H3N8 CIV strain A/canine/NY/120106 |

Real-time RT-PCR genotyping of CIVs

Sensitivity of the subtyping assay

Detection limit = 0.047 $EID_{50}$ units

Efficiency of the subtyping assay

Amplification factor = 1.99
Efficiency = 98.81

Figure 5A
Protein sequence alignment of HA protein of H3N2 and sequence identity

```
                    1                                                  50
SEQ ID NO:2   (1)   MKTIIALSYIFCLAFGQNLLGNENNAATLCLGHHAVPNGTMVKTITDDQI
SEQ ID NO:4   (1)   MKTIIALSYIFCLAFGQNLLGNENNAATLCLGHHAVPNGTMVKTITDDQI
SEQ ID NO:6   (1)   MKTIIALSYIFCLAFGQNLLGNENNAATLCLGHHAVPNGTMVKTITDDQI
                    51                                                 100
SEQ ID NO:2   (51)  EVTNATELVQNSTGKICNNPHKILDGRDCTLIDALLGDPHCDVFQNETW
SEQ ID NO:4   (51)  EVTNATELVQNSTGKICNNPHKILDGRDCTLIDALLGDPHCDVFQNETW
SEQ ID NO:6   (51)  EVTNATELVQNPSTGKICNNPHKILDGRDCTLIDALLGDPHCDVFQNETW
                    101                                                150
SEQ ID NO:2  (101)  DLFVERSNAFSNCYPYDVPDYASLRSIVASSGTLEFITEGFTWAGVTQNG
SEQ ID NO:4  (101)  DLFVERSNAFSNCYPYDVPDYASLRSIVASSGTLEFITEGFTWAGVTQNG
SEQ ID NO:6  (101)  DLFVERSNAFSNCYPYDVPDYASLRSIVASSGTLEFITEGFTWAGVTQNG
                    151                                                200
SEQ ID NO:2  (151)  GSGACKRGPANSFFSRLNWLTKSGNTYPVLNVTMPNNNNFDKLYIWGVHH
SEQ ID NO:4  (151)  GSGACKRGPANSFFSRLNWLTKSGNTYPVLNVTMPNNNNFDKLYIWGVHH
SEQ ID NO:6  (151)  GSGACKRGPANSFFSRLNWLTKSGNTYPVLNVTMPNNNNFDKLYIWGVHH
                    201                                                250
SEQ ID NO:2  (201)  PSTNQEQTSLYIQASGRVTVSTRRSQQTIIPNIGSRPLVRGQSGRISVY
SEQ ID NO:4  (201)  PSTNQEQTSLYIQASGRVKVSTRRSQQTIIPNIGSRPLVRGQSGRISVY
SEQ ID NO:6  (201)  PSTNQEQTSLYIQASGRVTVSTRRSQQTIIPNIGSRPLVRGQSGRISVY
                    251                                                300
SEQ ID NO:2  (251)  TIVKPGDILVINSNGNLIAPRGYFKMRTGKSSIMRSDAPIDTCISECITP
SEQ ID NO:4  (251)  TIVKPGDILVINSNGNLIAPRGYFKMRTGKSSIMRSDAPIDTCISECITP
SEQ ID NO:6  (251)  TIVKPGDILVINSNGNLIAPRGYFKMRTGKSSIMRSDAPIDTCISECITP
                    301                                                350
SEQ ID NO:2  (301)  NGSIPNEKPFQNVNKITYGACPKYVKQNTLKLATGMRNVPEKQTRGLFGA
SEQ ID NO:4  (301)  NGSIPNEKPFQNVNKITYGACPKYVKQNTLKLATGMRNVPEKQTRGLFGA
SEQ ID NO:6  (301)  NGSIPNEKPFQNVNKITYGACPKYVKQNTLKLATGMRNVPEKQTRGLFGA
                    351                                                400
SEQ ID NO:2  (351)  IAGFIENGWEGMVDGWYGFRHQNSEGTGQAADLKSTQAAIDQINGKLNRV
SEQ ID NO:4  (351)  IAGFIENGWEGMVDGWYGFRHQNSEGTGQAADLKSTQAAIDQINGKLNRV
SEQ ID NO:6  (351)  IAGFIENGWEGMVDGWYGFRHQNSEGTGQAADLKSTQAAIDQINGKLNRV
                    401                                                450
SEQ ID NO:2  (401)  IEKTNEKFHQIEKEFSEVEGRIQDLEKYVEDTKVDLWSYNAELLVALENQ
SEQ ID NO:4  (401)  IEKTNEKFHQIEKEFSEVEGRIQDLEKYVEDTKVDLWSYNAELLVALENQ
SEQ ID NO:6  (401)  IEKTNEKFHQIEKEFSEVEGRIQDLEKYVEDTKVDLWSYNAELLVALENQ
                    451                                                500
SEQ ID NO:2  (451)  NTIDLTDSEMNKLFEKTRRQLRENAEDMGNGCFKIYHKCDNACIESIRNG
SEQ ID NO:4  (451)  NTIDLTDSEMNKLFEKTRRQLRENAEDMGNGCFKIYHKCDNACIESIRNG
SEQ ID NO:6  (451)  NTIDLTDSEMNKLFEKTRRQLRENAEDMGNGCFKIYHKCDNACIESIRNG
                    501                                                550
SEQ ID NO:2  (501)  TYDHNIYRDEAVNNRFQIKGVELKSGYKDWILWISFAISCFLLCVVLLGF
SEQ ID NO:4  (501)  TYDHNIYRDEAVNNRFQIKGVELKSGYKDWILWISFAISCFLLCVVLLGF
SEQ ID NO:6  (501)  TYDHNIYRDEAVNNRFQIKGVELKSGYKDWILWISFAISCFLLCVVLLGF
                    551         566
SEQ ID NO:2  (551)  IMWACQRGNIRCNICI
SEQ ID NO:4  (551)  IMWACQRGNIRCNICI
SEQ ID NO:6  (551)  IMWACQRGNIRCNICI

Sequence identity:
SEQ ID NO:2 v. SEQ ID NO:4:    99.6%
SEQ ID NO:2 v. SEQ ID NO:6:    99.6%
SEQ ID NO:4 v. SEQ ID NO:6:    99.6%
```

Figure 5B
DNA sequence alignment of polynucleotide encoding HA protein of H3N2 and sequence identity

```
                            1                                                  50
SEQ ID NO:1    (1)    ATGAAAACTGTTATTGCTTTAAGCTATATTTTCTGCCTGGCTTTTGGTCA
SEQ ID NO:3    (1)    ATGAAAACTGTTATTGCTTTAAGCTATATTTTCTGCCTGGCTTTTGGTCA
SEQ ID NO:5    (1)    ATGAAAACTGTTATTGCTTTAAGCTATATTTTCTGCCTGGCTTTTGGTCA
                            51                                                 100
SEQ ID NO:1    (51)   GAATCTTCTAGGAAATGAAAATAATGCTGCAACACTATGGCTGGGACATC
SEQ ID NO:3    (51)   GAATCTTCTAGGAAATGAAAATAATGCTGCAACACTATGGCTGGGACATC
SEQ ID NO:5    (51)   GAATCTTCTAGGAAATGAAAATAATGCTGCAACACTATGGCTGGGACATC
                            101                                                150
SEQ ID NO:1    (101)  ATGCAGTGCCCGAACGGGACAATGGTGAAAACTATCACAGACGATCAAAT
SEQ ID NO:3    (101)  ATGCAGTGCCCGAACGGGACAATGGTGAAAACTATCACAGACGATCAAAT
SEQ ID NO:5    (101)  ATGCAGTGCCCGAACGGGACAATGGTGAAAACTATCACAGACGATCAAAT
                            151                                                200
SEQ ID NO:1    (151)  GAGGTGACCAACGGCACCGAGCTAGTCCAAAACCCCTCAACAGGGAAAAT
SEQ ID NO:3    (151)  GAGGTGACCAACGGCACCGAGCTAGTCCAAAACCCCTCAACAGGGAAAAT
SEQ ID NO:5    (151)  GAGGTGACCAACGGCACCGAGCTAGTCCAAAACCCCTCAACAGGGAAAAT
                            201                                                250
SEQ ID NO:1    (201)  ATGCAACAATCCCACAAGATTCTTGATGGGAGGGACTGCACACTAATAG
SEQ ID NO:3    (201)  ATGCAACAATCCCACAAGATTCTTGATGGGAGGGACTGCACACTAATAG
SEQ ID NO:5    (201)  ATGCAACAATCCCACAAGATTCTTGATGGGAGGGACTGCACACTAATAG
                            251                                                300
SEQ ID NO:1    (251)  ATGCCCTACTAGGGGACCCACACTGTGACGTCTTCCAAAATGAGACATGG
SEQ ID NO:3    (251)  ATGCCCTACTAGGGGACCCACACTGTGACGTCTTCCAAAATGAGACATGG
SEQ ID NO:5    (251)  ATGCCCTACTAGGGGACCCACACTGTGACGTCTTCCAAAATGAGACATGG
                            301                                                350
SEQ ID NO:1    (301)  GACCTTTTTGTGGAACGAAGCAATGCTTTTAGCAATTGTTACCCTTATGA
SEQ ID NO:3    (301)  GACCTTTTTGTGGAACGAAGCAATGCTTTTAGCAATTGTTACCCTTATGA
SEQ ID NO:5    (301)  GACCTTTTTGTGGAACGAAGCAATGCTTTTAGCAATTGTTACCCTTATGA
                            351                                                400
SEQ ID NO:1    (351)  TGTACCAGACTATGCATCCCTCCGATCCATAGTTGCATCATCAGGCACAT
SEQ ID NO:3    (351)  TGTACCAGACTATGCATCCCTCCGATCCATAGTTGCATCATCAGGCACAT
SEQ ID NO:5    (351)  TGTACCAGACTATGCATCCCTCCGATCCATAGTTGCATCATCAGGCACAT
                            401                                                450
SEQ ID NO:1    (401)  TGGAGTTCATCACTGAAGGTTTCACTTGGGCAGGAGTAACTCAAAATGGA
SEQ ID NO:3    (401)  TGGAGTTCATCACTGAAGGTTTCACTTGGGCAGGAGTAACTCAAAATGGA
SEQ ID NO:5    (401)  TGGAGTTCATCACTGAAGGTTTCACTTGGGCAGGAGTAACTCAAAATGGA
                            451                                                500
SEQ ID NO:1    (451)  GGAAGCGGTGCTTGTAAAAGGGGACCTGCTAATAGTTCTTCAGTAGAATT
SEQ ID NO:3    (451)  GGAAGCGGTGCTTGTAAAAGGGGACCTGCTAATAGTTCTTCAGTAGAATT
SEQ ID NO:5    (451)  GGAAGCGGTGCTTGTAAAAGGGGACCTGCTAATAGTTCTTCAGTAGAATT
                            501                                                550
SEQ ID NO:1    (501)  AAATTGGTTAACTAAATCAGGAAATACATATCCAGTGCTGAATGTGACTA
SEQ ID NO:3    (501)  AAATTGGTTAACTAAATCAGGAAATACATATCCAGTGCTGAATGTGACTA
SEQ ID NO:5    (501)  AAATTGGTTAACTAAATCAGGAAATACATATCCAGTGCTGAATGTGACTA
                            551                                                600
SEQ ID NO:1    (551)  TGCCAAACAACAACAATTTCGACAAATTATACATTTGGGGAGTTCATCAC
SEQ ID NO:3    (551)  TGCCAAACAACAACAATTTCGACAAATTATACATTTGGGGAGTTCATCAC
SEQ ID NO:5    (551)  TGCCAAACAACAACAATTTCGACAAATTATACATTTGGGGAGTTCATCAC
                            601                                                650
SEQ ID NO:1    (601)  CCAAGCACTAATCAAGAACAAACCAGCCTGTATATTCAGGCCTCAGGAAG
SEQ ID NO:3    (601)  CCAAGCACTAATCAAGAACAAACCAGCCTGTATATTCAGGCCTCAGGAAG
SEQ ID NO:5    (601)  CCAAGCACTAATCAAGAACAAACCAGCCTGTATATTCAGGCCTCAGGAAG
```

Figure 5C

```
                 651                                                  700
SEQ ID NO:1  (651) AGTCA_AGTCTCTACCAGGAGAAGCCAACAGACCATAATCCCAAACATTG
SEQ ID NO:3  (651) AGTCAAAGTCTCTACCAGGAGAAGCCAACAGACCATAATCCCAAACATTG
SEQ ID NO:5  (651) AGTCA_AGTCTCTACCAGGAGAAGCCAACAGACCATAATCCCAAACATTG
                 701                                                  750
SEQ ID NO:1  (701) GATCTAGACCCTTGGTAAGGGGCAATCTGGCAGAATAAGCGTACATTGG
SEQ ID NO:3  (701) GATCTAGACCCTTGGTAAGGGGCCAATCTGGCAGAATAAGCGTA_ATTGG
SEQ ID NO:5  (701) GATCTAGACCCTTGGTAAGGGGCCAATCTGGCAGAATAAGCGTA_ATTGG
                 751                                                  800
SEQ ID NO:1  (751) ACAATAGTCAAACCTGGAGACATACTGGTAATAAACAGTAATGGAAACCT
SEQ ID NO:3  (751) ACAATAGTCAAACCTGGAGACATACTGGTAATAAACAGTAATGGAAACCT
SEQ ID NO:5  (751) ACAATAGTCAAACCTGGAGACATACTGGTAATAAACAGTAATGGAAACCT
                 801                                                  850
SEQ ID NO:1  (801) AATGCTCCTCGAGGATACTTCAAAATGCACATTGGGAAAAGCTCAATAA
SEQ ID NO:3  (801) AATGCTCCTCGAGGATACTTCAAAATGCACATTGGGAAAAGCTCAATAA
SEQ ID NO:5  (801) AATGCTCCTCGAGGATACTTCAAAATGCACATTGGGAAAAGCTCAATAA
                 851                                                  900
SEQ ID NO:1  (851) TGAGATCAGATGCACCTATTGACACCTGCATTTCCGAATGTATCACCCCG
SEQ ID NO:3  (851) TGAGATCAGATGCACCTATTGACACCTGCATTTCCGAATGTATCACCCCG
SEQ ID NO:5  (851) TGAGATCAGATGCACCTATTGACACCTGCATTTCCGAATGTATCACCCCG
                 901                                                  950
SEQ ID NO:1  (901) AACGGGAGCATCCCCAATGAAAAGCCCTTCCAAAATGTAAACAAGATCAC
SEQ ID NO:3  (901) AACGGGAGCATCCCCAATGAAAAGCCCTTCCAAAATGTAAACAAGATCAC
SEQ ID NO:5  (901) AACGGGAGCATCCCCAATGAAAAGCCCTTCCAAAATGTAAACAAGATCAC
                 951                                                 1000
SEQ ID NO:1  (951) ATACGGAGCATGTCCCAAATATGTTAAGCAAAACACCTTGAAACTGGCAA
SEQ ID NO:3  (951) ATACGGAGCATGTCCCAAATATGTTAAGCAAAACACCTTGAAACTGGCAA
SEQ ID NO:5  (951) ATACGGAGCATGTCCCAAATATGTTAAGCAAAACACCTTGAAACTGGCAA
                1001                                                 1050
SEQ ID NO:1 (1001) CAGGAATGCCGAATGTCCCTGAGAGGCAAACCAGAGGCCTGTTCGGCCCA
SEQ ID NO:3 (1001) CAGGAATGCCGAATGTCCCTGAGAGGCAAACCAGAGGCCTGTTCGGCCCA
SEQ ID NO:5 (1001) CAGGAATGCCGAATGTCCCTGAGAGGCAAACCAGAGGCCTGTTCGGCCCA
                1051                                                 1100
SEQ ID NO:1 (1051) ATACCAGGCTTCATAGAAAATGGATGGAAGGGATGGTAGACGGTTGGTA
SEQ ID NO:3 (1051) ATACCAGGCTTCATAGAAAATGGATGGAAGGGATGGTAGACGGTTGGTA
SEQ ID NO:5 (1051) ATACCAGGCTTCATAGAAAATGGATGGAAGGGATGGTAGACGGTTGGTA
                1101                                                 1150
SEQ ID NO:1 (1101) TGGCTTCAGGCACCAAAATTCCGAAGGTACAGGACAAGCAGCAGACCTTA
SEQ ID NO:3 (1101) TGGCTTCAGGCACCAAAATTCCGAAGGTACAGGACAAGCAGCAGACCTTA
SEQ ID NO:5 (1101) TGGCTTCAGGCACCAAAATTCCGAAGGTACAGGACAAGCAGCAGACCTTA
                1151                                                 1200
SEQ ID NO:1 (1151) AAAGCACTCAGGCAGCCATTGACCAGATTAATGGGAAATTGAACAGAGTG
SEQ ID NO:3 (1151) AAAGCACTCAGGCAGCCATTGACCAGATTAATGGGAAATTGAACAGAGTG
SEQ ID NO:5 (1151) AAAGCACTCAGGCAGCCATTGACCAGATTAATGGGAAATTGAACAGAGTG
                1201                                                 1250
SEQ ID NO:1 (1201) ATTGAAAAAACGAATGAGAAGTTCCATCAAATTGAAAAGGAGTTTTCCGA
SEQ ID NO:3 (1201) ATTGAAAAAACGAATGAGAAGTTCCATCAAATTGAAAAGGAGTTTTCCGA
SEQ ID NO:5 (1201) ATTGAAAAAACGAATGAGAAGTTCCATCAAATTGAAAAGGAGTTTTCCGA
                1251                                                 1300
SEQ ID NO:1 (1251) AGTAGAAGGGAGGATTCAAGACCTTGAGAGATACGTTGAAGACACAAAAG
SEQ ID NO:3 (1251) AGTAGAAGGGAGGATTCAAGACCTTGAGAGATACGTTGAAGACACAAAAG
SEQ ID NO:5 (1251) AGTAGAAGGGAGGATTCAAGACCTTGAGAGATACGTTGAAGACACAAAAG
```

Figure 5D

```
               1301                                              1350
SEQ ID NO:1 (1301) TAGATCTTTGGTCTTACAATGCCGAGCTTCTTGTTGCCTTAGAAAACCAG
SEQ ID NO:3 (1301) TAGATCTTTGGTCTTACAATGCCGAGCTTCTTGTTGCCTTAGAAAACCAG
SEQ ID NO:5 (1301) TAGATCTTTGGTCTTACAATGCCGAGCTTCTTGTTGCCTTAGAAAACCAG
               1351                                              1400
SEQ ID NO:1 (1351) AACACAATTGATTTAACTGATTCAGAAATGAACAAATTGTTTGAAAAGAC
SEQ ID NO:3 (1351) AACACAATTGATTTAACTGATTCAGAAATGAACAAATTGTTTGAAAAGAC
SEQ ID NO:5 (1351) AACACAATTGATTTAACTGATTCAGAAATGAACAAATTGTTTGAAAAGAC
               1401                                              1450
SEQ ID NO:1 (1401) TAGGAGGCAATTGAGGGAAAATGCTGAAGACATGGGCAATGGCTGCTTCA
SEQ ID NO:3 (1401) TAGGAGGCAATTGAGGGAAAATGCTGAAGACATGGGCAATGGCTGCTTCA
SEQ ID NO:5 (1401) TAGGAGGCAATTGAGGGAAAATGCTGAAGACATGGGCAATGGCTGCTTCA
               1451                                              1500
SEQ ID NO:1 (1451) AGATATACCACAAGTGTGACAATGCTTGCATAGAATCGATTAGAAACGGA
SEQ ID NO:3 (1451) AGATATACCACAAGTGTGACAATGCTTGCATAGAATCGATTAGAAACGGA
SEQ ID NO:5 (1451) AGATATACCACAAGTGTGACAATGCTTGCATAGAATCGATTAGAAACGGA
               1501                                              1550
SEQ ID NO:1 (1501) ACTTATGACCATAACATATATAGAGATGAGGCAGTGAACAATCGGTTCCA
SEQ ID NO:3 (1501) ACTTATGACCATAACATATATAGAGATGAGGCAGTGAACAATCGGTTCCA
SEQ ID NO:5 (1501) ACTTATGACCATAACATATATAGAGATGAGGCAGTGAACAATCGGTTCCA
               1551                                              1600
SEQ ID NO:1 (1551) GATCAAAGTTGTTGAGCTAAAGTCTGGATACAAAGACTGGATCTTTGGA
SEQ ID NO:3 (1551) GATCAAAGTTGTTGAGCTAAAGTCTGGATACAAAGACTGGATCTTTGGA
SEQ ID NO:5 (1551) GATCAAAGTTGTTGAGCTAAAGTCTGGATACAAAGACTGGATCTTGTGGA
               1601                                              1650
SEQ ID NO:1 (1601) TTTCCTTTGCATATCATGCTTTTTGCTTTGTGTTGTCTTGCTGGGTTTC
SEQ ID NO:3 (1601) TTTCCTTTGCATATCATGCTTTTTGCTTTGTGTTGTCTTGCTGGGTTTC
SEQ ID NO:5 (1601) TTTCCTTTGCATATCATGCTTTTTGCTTTGTGTTGTCTTGCTGGGTTTC
               1651                                              1700
SEQ ID NO:1 (1651) ATTATGTGGCCTGCCAGAGAGGCAACATTAGGTGCAACATTTGCATTTG
SEQ ID NO:3 (1651) ATTATGTGGCCTGCCAGAGAGGCAACATTAGGTGCAACATTTGCATTTG
SEQ ID NO:5 (1651) ATTATGTGGCCTGCCAGAGAGGCAACATTAGGTGCAACATTTGCATTTG
               1701
SEQ ID NO:1 (1701) A
SEQ ID NO:3 (1701) A
SEQ ID NO:5 (1701) A

Sequence identity:
SEQ ID NO:1 v. SEQ ID NO:3:  99.9%
SEQ ID NO:1 v. SEQ ID NO:5:  99.9%
SEQ ID NO:3 v. SEQ ID NO:5:  99.8%
```

Figure 5E
Protein sequence alignment of HA protein of H3N8 and sequence identity

[Sequence alignment of SEQ ID NO:31, SEQ ID NO:35, and SEQ ID NO:39 from positions 1 to 565, shown in blocks of 50 residues]

Sequence identity
SEQ ID NO:31 v. SEQ ID NO:35:   98.9%
SEQ ID NO:31 v. SEQ ID NO:39:   97.9%
SEQ ID NO:35 v. SEQ ID NO:39:   97.7%

Figure 5F
DNA sequence alignment of polynucleotide encoding HA protein of H3N8 and sequence identity

```
                         1                                                  50
SEQ ID NO:30    (1)      ATGAAGACAACCATTATTTTAATACTACTGACCCATTGGGCCACAGTCA
SEQ ID NO:34    (1)      ATGAAGACAACCATTATTTTAATACTACTGACCCATTGGGCCACAGTCA
SEQ ID NO:38    (1)      ATGAAGACAACCATTATTTTAATACTACTGACCCATTGGGCCCACAGTCA
                         51                                                 100
SEQ ID NO:30    (51)     AAACCCAATCAGTGGCAATAACACAGCCACACTGTGTCTGGGACACCATG
SEQ ID NO:34    (51)     AAACCCAATCAGTGGCAATAACACAGCCACACTGTGTCTGGGACACCATG
SEQ ID NO:38    (51)     AAACCCAATCAGTGGCAATAACACAGCCACACTGTGTCTGGGACACCATG
                         101                                                150
SEQ ID NO:30    (101)    CAGTAGCAAATGGAACATTAGTAAAAACAATGACTGATCATCAAATTGAG
SEQ ID NO:34    (101)    CAGTAGCAAATGGAACATTAGTAAAAACAATGACTGATCATCAAATTGAG
SEQ ID NO:38    (101)    CAGTAGCAAATGGAACATTAGTAAAAACAATGACTGATCATCAAATTGAG
                         151                                                200
SEQ ID NO:30    (151)    GTGACAAATGTTACAGAATTAGTTCAGAGCATTTCAATGGGGAAAATATG
SEQ ID NO:34    (151)    GTGACAAATGTTACAGAATTAGTTCAGAGCATTTCAATGGGGAAAATATG
SEQ ID NO:38    (151)    GTGACAAATGTTACAGAATTAGTTCAGAGCATTTCAATGGGGAAAATATG
                         201                                                250
SEQ ID NO:30    (201)    CAACAAATCATATAGAATTCTAGATGGAAGAAATTGCACATTAATAGATG
SEQ ID NO:34    (201)    CAACAAATCATATAGAATTCTAGATGGAAGAAATTGCACATTAATAGATG
SEQ ID NO:38    (201)    CAACAAATCATATAGAATTCTAGATGGAAGAAATTGCACATTAATAGATG
                         251                                                300
SEQ ID NO:30    (251)    CAATGCTAGGAGACCCCCAGTGTGACGCCTTTCAGTATGAGAGTTGGGAC
SEQ ID NO:34    (251)    CAATGCTAGGAGACCCCCAGTGTGACGCCTTTCAGTATGAGAGTTGGGAC
SEQ ID NO:38    (251)    CAATGCTAGGAGACCCCCACTGTGACGCCTTTCAGTATGAGAGTTGGGAC
                         301                                                350
SEQ ID NO:30    (301)    CTCTTTATAGAAAGAAGCAATGCTTTCAGCAATTGCTACCCATATGACAT
SEQ ID NO:34    (301)    CTCTTTATAGAAAGAAGCAAGGCTTTCAGCAATTGCTACCCATATGACAT
SEQ ID NO:38    (301)    CTCTTTATAGAAAGAAGCAAAGCTTTCAGCAATTGCTACCCATATGACAT
                         351                                                400
SEQ ID NO:30    (351)    CCCTGACTATGCATCGCTCCGATCCATTGTAGCATCCTCAGGAACAGTGA
SEQ ID NO:34    (351)    CCCTGACTATGCATCGCTCCGATCCATTGTAGCATCCTCAGGAACAGTGA
SEQ ID NO:38    (351)    CCCTGACTATGCATCGCTCCGATCCATTGTAGCATCCTCAGGAACAGTGA
                         401                                                450
SEQ ID NO:30    (401)    AATTCACAGTAGAGGGATTCACATGGACAGGTGTCACTCAAAACGGAAGA
SEQ ID NO:34    (401)    AATTCACAGGAGAGGGATTCACATGGACAGGTGTCACTCAAAACGGAAGA
SEQ ID NO:38    (401)    AATTCACAGGAGAGGGATTCACATGGACAGGTGTCACTCAAAACGGAAGA
                         451                                                500
SEQ ID NO:30    (451)    AGTGGAGCCTGCAAAAGGGGATCAGCCGATAGTTTCTTTAGCCGACTGAA
SEQ ID NO:34    (451)    AGTGGAGCCTGCAAAAGGGGATCAGCCGATAGTTTCTTTAGCCGACTGAA
SEQ ID NO:38    (451)    AGTGGAGCCTGCAAAAGGGGATCAGCCGATAGTTTCTTTAGCCGACTGAA
                         501                                                550
SEQ ID NO:30    (501)    TTGGCTAACAAAAATCTGGAAGCTCTTACCCCACATTGAATGTAACAATGC
SEQ ID NO:34    (501)    TTGGCTAACAAAAATCTGGAAGCTCTTACCCCACATTGAATGTAACAATGC
SEQ ID NO:38    (501)    TTGGCTAACAAAAATCTGGAAGCTCTTACCCCACATTGAATGTAACAATGC
                         551                                                600
SEQ ID NO:30    (551)    CTAACAATGAAAAATTTGACAAGCTATACATCTGGGGATTCATCACCCA
SEQ ID NO:34    (551)    CTAACAATGAAAAATTTGACAAGCTATACATCTGGGGATTCATCACCCA
SEQ ID NO:38    (551)    CTAACAATGAAAAATTTGACAAGCTATACATCTGGGGGATTCATCACCCA
                         601                                                650
SEQ ID NO:30    (601)    AGCTCAAATCAAGAGCAGACAAAATTGTACATCAAGAATCAGGACGAGT
SEQ ID NO:34    (601)    AGCTCAAATCAAGAGCAGACAAAATTGTACATTAAGAATCAGGACGAGT
SEQ ID NO:38    (601)    AGCTCAAATCAAGAGCAGACAAAATTGTACATCAAGAATCAGGACGAGT
```

Figure 5G

|                |        | 651                                                  700 |
|----------------|--------|---------------------------------------------------------|
| SEQ ID NO:30   | (651)  | AACAGTCTCAACAAAAAGAAGTCAACAAACAATAATNCCTNACATCGGAT      |
| SEQ ID NO:34   | (651)  | AACAGTCTCAACAAAAAGAAGTCAACAAACAATAATTCCTNACATCGGAT      |
| SEQ ID NO:38   | (651)  | AACAGTCTCAACAAAAAGAAGTCAACAAACAATAATNCTAACATCGGAT       |
|                |        | 701                                                  750 |
| SEQ ID NO:30   | (701)  | CTAGACGTTNNTCAGAGTTCAATCAGGCAGGATAAGCATATACTGGACC       |
| SEQ ID NO:34   | (701)  | CTAGACGTTNNTCAGAGTTCAATCAGGCAGGATAAGCATATACTGGACC       |
| SEQ ID NO:38   | (701)  | CTAGACGTTGGTCAGAGTTCAATCAGGCAGGATAAGCATATACTGGACC       |
|                |        | 751                                                  800 |
| SEQ ID NO:30   | (751)  | ATTGTAAAACCTGGAGATATCCTAATGATAAACAGTAATGGCAACTTAGN      |
| SEQ ID NO:34   | (751)  | ATTGTAAAACCTGGAGATATCCTAATGATAAACAGTAATGGCAACTTAGN      |
| SEQ ID NO:38   | (751)  | ATTGTAAAACCTGGAGATATCCTAATGATAAACAGTAATGGCAACTTAGN      |
|                |        | 801                                                  850 |
| SEQ ID NO:30   | (801)  | TGCACGGCGGGATATTNAAANTGAACNCAGGNAAAAGCTCTGTAATNN        |
| SEQ ID NO:34   | (801)  | TGCACGGCGGGATATTNAAANTGAACNCAGGNAAAAGCTCTGTAATTA        |
| SEQ ID NO:38   | (801)  | TGCACGGCGGGATATTTAAACTGAACACAGGGAAAAGCTCTGTAATNN        |
|                |        | 851                                                  900 |
| SEQ ID NO:30   | (851)  | GATCGATGTACCATAGACATTTGTGTGTCTGAATGTATTACACCAAAT        |
| SEQ ID NO:34   | (851)  | GATCGATGTACCATAGACATTTGTGTGTCTGAATGTATTACACCAAAT        |
| SEQ ID NO:38   | (851)  | GATCGATGTACCATAGACATTTGTGTGTCTGAATGTATTACACCAAAT        |
|                |        | 901                                                  950 |
| SEQ ID NO:30   | (901)  | GGAAGCATCTCCAACGACAAGCCATTCCAAAATGTGAACAAAGTTACATA      |
| SEQ ID NO:34   | (901)  | GGAAGCATCTCCAACGACAAGCCATTCCAAAATGTGAACAAAGTTACATA      |
| SEQ ID NO:38   | (901)  | GGAAGCATCTCCAACGACAAGCCATTCCAAAATGTGAACAAAGTTACANN      |
|                |        | 951                                                 1000 |
| SEQ ID NO:30   | (951)  | TGGAAAATGCCCCAAGTATATCAGGCAAAACACTTTAAAGNTGGCCACTG      |
| SEQ ID NO:34   | (951)  | TGGAAAATGCCCCAAGTATATCAGGCAAAACACTTTAAAGNTGGCCACTG      |
| SEQ ID NO:38   | (951)  | TGGAAAATGCCCCAAGTATATCAGGCAAAACACTTTAAAGCTGGCCACTG      |
|                |        | 1001                                                1050 |
| SEQ ID NO:30   | (1001) | GGATGAGGAATGTNCCAGAAAAGCAAACCAGAGGAATCTTTGGNNGNATA      |
| SEQ ID NO:34   | (1001) | GGATGAGGAATGTNCCAGAAAAGCAAACCAGAGGAATCTTTGGNNGNATA      |
| SEQ ID NO:38   | (1001) | GGATGAGGAATGTACCAGAAAAGCAAACCAGAGGAATCTTTGAGCAATA       |
|                |        | 1051                                                1100 |
| SEQ ID NO:30   | (1051) | GCGGGATTCATCGAAAACGGCTGGAAGGAATGGTTGATGGTGGTATGG        |
| SEQ ID NO:34   | (1051) | GCGGGATTCATCGAAAACGGCTGGAAGGAATGGTTGATGGTGGTATGG        |
| SEQ ID NO:38   | (1051) | GCGGGATTCATCGAAAACGGCTGGAAGGAATGGTTGATGGTGGTATGG        |
|                |        | 1101                                                1150 |
| SEQ ID NO:30   | (1101) | GTTCCGATATCAAAACTCGAAGGAACAGGGCAAGCTGCAGATCTAAAGA       |
| SEQ ID NO:34   | (1101) | GTTCCGATATCAAAACTCGAAGGAACAGGGCAAGCTGCAGATCTAAAGA       |
| SEQ ID NO:38   | (1101) | GTTCCGATATCAAAACTCGAAGGAACAGGGCAAGCTGCAGATCTAAAGA       |
|                |        | 1151                                                1200 |
| SEQ ID NO:30   | (1151) | GCACTGAAGCAGCCATCGACCAGATTAATGGAAAGTTAAACAGNGTGATT      |
| SEQ ID NO:34   | (1151) | GCACTGAAGCAGCCATCGACCAGATTAATGGAAAGTTAAACAGNGTGATT      |
| SEQ ID NO:38   | (1151) | GCACTGAAGCAGCCATCGACCAGATTAATGGAAAGTTAAACAGAGTGATT      |
|                |        | 1201                                                1250 |
| SEQ ID NO:30   | (1201) | GAAAGAACCAATGAGAAATTCCATCAAATAGAGAAGGAATTCTCAGAAGT      |
| SEQ ID NO:34   | (1201) | GAAAGAACCAATGAGAAATTCCATCAAATAGAGAAGGAATTCTCAGAAGT      |
| SEQ ID NO:38   | (1201) | GAAAGAACCAATGAGAAATTCCATCAAATAGAGAAGGAATTCTCAGAAGT      |
|                |        | 1251                                                1300 |
| SEQ ID NO:30   | (1251) | AGAAGAAAGAATTCAGGACTTGGAGAAATATGTAGAAGACACCAAAATAG      |
| SEQ ID NO:34   | (1251) | AGAANGAAGAATTCAGGACTTGGAGAAATATGTAGAAGACACCAAAATAG      |
| SEQ ID NO:38   | (1251) | AGAANGAAGAATTCAGGACTTGGAGAAATATGTAGAAGACACCAAAATAG      |

Figure 5H

```
              1301                                                    1350
SEQ ID NO:30  (1301) ACCTATGGTCCTACAATGCAGAA  CTGGTGGCTCTAGAAAATCAACAT
SEQ ID NO:34  (1301) ACCTATGGTCCTACAATGCAGAA TACTGGTGGCTCTAGAAAATCAACAT
SEQ ID NO:38  (1301) ACCTATGGTCCTACAATGCAGAATT CTGGTGGCTCTAGAAAATCAACAT
              1351                                                    1400
SEQ ID NO:30  (1351) ACAATTGACTTAACAGATGCA AAAATGAATAAATTATTTGAGAAGACTAG
SEQ ID NO:34  (1351) ACAATTGACTTAACAGATGCA AAAATGAATAAATTATTTGAGAAGACTAG
SEQ ID NO:38  (1351) ACAATTGACTTAACAGATGCAAAAATGAATAAATTATTTGAGAAGACTAG
              1401                                                    1450
SEQ ID NO:30  (1401) ACG CAGTT AGAGAAAA  CAGAAGACATGGA  TGGATGTTTCAAGA
SEQ ID NO:34  (1401) ACGCCAGTT AGAGAAAA G CAGAAGACATGGAA TGGATGTTTCAAGA
SEQ ID NO:38  (1401) ACGCCAGTTGAGAGAAAACG CAGAAGACATGGAA GTGGATGTTTCAAGA
              1451                                                    1500
SEQ ID NO:30  (1451) TTTA CACAA TGTCATAATGCATGCATTGA CAATAAGAACTGGAACA
SEQ ID NO:34  (1451) TTTA CACAA TGTCATAATGCATGCATTGAGTCAATAAGAACTGGAACA
SEQ ID NO:38  (1451) TTTATCACAAATTGTCATAATGCATGCATTGA TCAATAAGAACTGGAACA
              1501                                                    1550
SEQ ID NO:30  (1501) TATGACCATTACATATACAGAGATGAAGCA AAACAACCGATTTCAGAT
SEQ ID NO:34  (1501) TATGACCATTACATATACAGAGATGAAGC A AAACAACCGATTTCAGAT
SEQ ID NO:38  (1501) TATGACCATTACATATACAGAGATGAAGCATTAAACAACCGATTTCAGAT
              1551                                                    1600
SEQ ID NO:30  (1551) CAAAGGTGTAGAG TTGAAATCAGGCTACAAAGATGGATACTGTGGATT
SEQ ID NO:34  (1551) CAAAGGTGTAGAG TTGAAATCAGGCTACAAAGATGGATACTGTGGATT
SEQ ID NO:38  (1551) CAAAGGTGTAGAGTTTAAATCAGGCTACAAAGATGGATACTGTGGATT
              1601                                                    1650
SEQ ID NO:30  (1601) CATTCGCCATATCATGCTTCTTAATTTGGCTTGTTCTATTGGGTTCATT
SEQ ID NO:34  (1601) CATTCGCCATATCATGCTTCTTAATTTGGTTGTTCTATTGGGTTCATT
SEQ ID NO:38  (1601) CATTCGCCATATCATGCTTCTTAATTTGGTTGTTCTATTGGGTTTCATT
              1651                                            1695
SEQ ID NO:30  (1651) ATGTGGGCTTGCCAAAAAGGCAACATCAGATGCAACATTTGCAT
SEQ ID NO:34  (1651) ATGTGGGCTTGCCAAAAAGGCAACATCAGATGCAACATTTGCAT
SEQ ID NO:38  (1651) ATGTGGGCTTGCCAAAAAGGCAACATCAGATGCAACATTTGCATT

Sequence identity:
SEQ ID NO:30 v. SEQ ID NO:34:  99.3%
SEQ ID NO:30 v. SEQ ID NO:38:  98.1%
SEQ ID NO:34 v. SEQ ID NO:38:  97.8%
```

Sequence identity between HA proteins of H3N2 and H3N8

| SEQ ID NO: | 2 | 4 | 6 | 31 | 35 | 39 |
|---|---|---|---|---|---|---|
| 2 | | 99.6% | 99.6% | 84.4% | 84.8% | 85.4% |
| 4 | | | 99.6% | 84.8% | 84.8% | 85.3% |
| 6 | | | | 85.0% | 85.0% | 85.5% |
| 31 | | | | | 98.9% | 97.9% |
| 35 | | | | | | 97.7% |
| 39 | | | | | | |

Figure 5I
Protein sequence alignment of NA protein of H3N2 and sequence identity

```
                    1                                                  50
SEQ ID NO:8    (1)  MNPNQKIIAIGSVSLTIATVCFLLQIAILATTVTLYFKQHECNIPSNSQV
SEQ ID NO:10   (1)  MNPNQKIIAIGSVSLTIATVCFLLQIAILATTVTLYFKQHECNIPSNSQV
SEQ ID NO:12   (1)  MNPNQKIIAIGSVSLTIATVCFLLQIAILATTVTLYFKQHECNIPSNSQV
                    51                                                100
SEQ ID NO:8    (51) VPCKPIIERNITEVVYLNNTTIEKEICSVVLEYRNWSKPQCQITGFAPF
SEQ ID NO:10   (51) VPCKPIIERNITEVVYLNNTTIEKEICSVVLEYRNWSKPQCQITGFAPF
SEQ ID NO:12   (51) VPCKPIIERNITEVVYLNNTTIEKEICSVVLEYRNWSKPQCQITGFAPF
                    101                                               150
SEQ ID NO:8    (101) SKDNSIRLSAGGDIWVTREPYVSCDHSKCYQFALGQGTTLNNKHSNSTIH
SEQ ID NO:10   (101) SKDNSIRLSAGGDIWVTREPYVSCDHSKCYQFALGQGTTLNNKHSNSTIH
SEQ ID NO:12   (101) SKDNSIRLSAGGDIWVTREPYVSCDHSKCYQFALGQGTTLNNKHSNSTIH
                    151                                               200
SEQ ID NO:8    (151) DRTSHRTLLMNELGVPFHLGTKQVCIAWSSSSCHDGKAWLHVCVTGDDRN
SEQ ID NO:10   (151) DRTSHRTLLMNELGVPFHLGTKQVCIAWSSSSCHDGKAWLHVCVTGDDRN
SEQ ID NO:12   (151) DRTSHRTLLMNELGVPFHLGTKQVCIAWSSSSCHDGKAWLHVCVTGDDRN
                    201                                               250
SEQ ID NO:8    (201) ATASFVYNGMLVDSIGSWSRNILRTQESECVCINGTCTVVMTDGSASGRA
SEQ ID NO:10   (201) ATASFVYNGMLVDSIGSWSRNILRTQESECVCINGTCTVVMTDGSASGRA
SEQ ID NO:12   (201) ATASFVYNGMLVDSIGSWSRNILRTQESECVCINGTCTVVMTDGSASGRA
                    251                                               300
SEQ ID NO:8    (251) DTRILFIEEGKIIHISPLSGSAQHIEECSCYPRYPNVRCVCRDNWKGSNR
SEQ ID NO:10   (251) DTRILFIEEGKIIHISPLSGSAQHIEECSCYPRYPNVRCVCRDNWKGSNR
SEQ ID NO:12   (251) DTRILFIEEGKIIHISPLSGSAQHIEECSCYPRYPNVRCVCRDNWKGSNR
                    301                                               350
SEQ ID NO:8    (301) PVIDINMADYNINSSYVCSGLVGDTPRNDDSSSSNCRDPNNERGNPGVK
SEQ ID NO:10   (301) PVIDINMADYNINSSYVCSGLVGDTPRNDDSSSSNCRDPNNERGNPGVK
SEQ ID NO:12   (301) PVIDINMADYNINSSYVCSGLVGDTPRNDDSSSSNCRDPNNERGNPGVK
                    351                                               400
SEQ ID NO:8    (351) GWAFDNDNDVWMGRTISKDLRSGYETFKVIGGWTTANSKSQVNRQVIVDN
SEQ ID NO:10   (351) GWAFDNDNDVWMGRTISKDLRSGYETFKVIGGWTTANSKSQVNRQVIVDN
SEQ ID NO:12   (351) GWAFDNDNDVWMGRTISKDLRSGYETFKVIGGWTTANSKSQVNRQVIVDN
                    401                                               450
SEQ ID NO:8    (401) NNWSGYSGIFSVEGKSCVNRCFYVELIRGRPQETRVWWTSNSIVVFCGTS
SEQ ID NO:10   (401) NNWSGYSGIFSVEGKSCVNRCFYVELIRGRPQETRVWWTSNSIVVFCGTS
SEQ ID NO:12   (401) NNWSGYSGIFSVEGKSCVNRCFYVELIRGRPQETRVWWTSNSIVVFCGTS
                    451            469
SEQ ID NO:8    (451) GTYGTGSWPDGANINFMPI
SEQ ID NO:10   (451) GTYGTGSWPDGANINFMPI
SEQ ID NO:12   (451) GTYGTGSWPDGANINFMPI

Sequence identity
SEQ ID NO:8  v. SEQ ID NO:10:  100.0%
SEQ ID NO:8  v. SEQ ID NO:12:  100.0%
SEQ ID NO:10 v. SEQ ID NO:12:  100.0%
```

Figure 5J
DNA sequence alignment of polynucleotide encoding NA protein of H3N2 and sequence identity

Figure 5K

```
                     651                                                  700
SEQ ID NO:7   (651)  ATGGTCTCGAAATATCCTCAGAACTCAAGAGTCAGAATGTGTTTGCATCA
SEQ ID NO:9   (651)  ATGGTCTCGAAATATCCTCAGAACTCAAGAGTCAGAATGTGTTTGCATCA
SEQ ID NO:11  (651)  ATGGTCTCGAAATATCCTCAGAACTCAAGAGTCAGAATGTGTTTGCATCA
                     701                                                  750
SEQ ID NO:7   (701)  ATGGGACTTGTACAGTAGTAATGACTGATGGAAGTGCATCAGGAAGGGCT
SEQ ID NO:9   (701)  ATGGGACTTGTACAGTAGTAATGACTGATGGAAGTGCATCAGGAAGGGCT
SEQ ID NO:11  (701)  ATGGGACTTGTACAGTAGTAATGACTGATGGAAGTGCATCAGGAAGGGCT
                     751                                                  800
SEQ ID NO:7   (751)  GATACTAGAATACTATTCATCAGAGAGGGGAAAATTATCCATATTAGCCC
SEQ ID NO:9   (751)  GATACTAGAATACTATTCATCAGAGAGGGGAAAATTATCCATATTAGCCC
SEQ ID NO:11  (751)  GATACTAGAATACTATTCATCAGAGAGGGGAAAATTATCCATATTAGCCC
                     801                                                  850
SEQ ID NO:7   (801)  ATTGTCAGGGAGTGCTCAACACATAGAGGAATGTTCCTGTTATCCCGGAT
SEQ ID NO:9   (801)  ATTGTCAGGGAGTGCTCAACACATAGAGGAATGTTCCTGTTATCCCGGAT
SEQ ID NO:11  (801)  ATTGTCAGGGAGTGCTCAACACATAGAGGAATGTTCCTGTTATCCCGGAT
                     851                                                  900
SEQ ID NO:7   (851)  ATCCAAATGTTAGATGTGTTTGCAGAGACAATTGGAAGGGCTCCAATAGG
SEQ ID NO:9   (851)  ATCCAAATGTTAGATGTGTTTGCAGAGACAATTGGAAGGGCTCCAATAGG
SEQ ID NO:11  (851)  ATCCAAATGTTAGATGTGTTTGCAGAGACAATTGGAAGGGCTCCAATAGG
                     901                                                  950
SEQ ID NO:7   (901)  CCCGTTATAGATATAAATATGGCAGATTATAACATCAATTCCAGTTATGT
SEQ ID NO:9   (901)  CCCGTTATAGATATAAATATGGCAGATTATAACATCAATTCCAGTTATGT
SEQ ID NO:11  (901)  CCCGTTATAGATATAAATATGGCAGATTATAACATCAATTCCAGTTATGT
                     951                                                 1000
SEQ ID NO:7   (951)  CTGTTCAGGACTTGTTGGCGATACACCAAGGAATGATGATAGCTCTAGCA
SEQ ID NO:9   (951)  CTGTTCAGGACTTGTTGGCGATACACCAAGGAATGATGATAGCTCTAGCA
SEQ ID NO:11  (951)  CTGTTCAGGACTTGTTGGCGATACACCAAGGAATGATGATAGCTCTAGCA
                     1001                                                1050
SEQ ID NO:7   (1001) GCAGTAACTGCAAGGATCCTAATAATGAGAGAGGGAATCCAGGAGTGAAG
SEQ ID NO:9   (1001) GCAGTAACTGCAAGGATCCTAATAATGAGAGAGGGAATCCAGGAGTGAAG
SEQ ID NO:11  (1001) GCAGTAACTGCAAGGATCCTAATAATGAGAGAGGGAATCCAGGAGTGAAG
                     1051                                                1100
SEQ ID NO:7   (1051) GGTGGGCTTTCATAATGATAATGACGTTTGGATGGGAGGACAATCAG
SEQ ID NO:9   (1051) GGTGGGCTTTCATAATGATAATGACGTTTGGATGGGAGGACAATCAG
SEQ ID NO:11  (1051) GGTGGGCTTTCATAATGATAATGACGTTTGGATGGGAGGACAATCAG
                     1101                                                1150
SEQ ID NO:7   (1101) CAAAGATTTACGTTCAGGTTATGAGACTTTCAAGGTCATTGGTGGTGGA
SEQ ID NO:9   (1101) CAAAGATTTACGTTCAGGTTATGAGACTTTCAAGGTCATTGGTGGTGGA
SEQ ID NO:11  (1101) CAAAGATTTACGTTCAGGTTATGAGACTTTCAAGGTCATTGGTGGTGGA
                     1151                                                1200
SEQ ID NO:7   (1151) CCACTGCTAATTCCAAGTCACAGGTCAATAGACAAGTCATAGTTGACAAT
SEQ ID NO:9   (1151) CCACTGCTAATTCCAAGTCACAGGTCAATAGACAAGTCATAGTTGACAAT
SEQ ID NO:11  (1151) CCACTGCTAATTCCAAGTCACAGGTCAATAGACAAGTCATAGTTGACAAT
                     1201                                                1250
SEQ ID NO:7   (1201) AATAACTGGTCTGGTTATTCTGGTATTTTCTCGGTTGAAGGCAAAAGCTG
SEQ ID NO:9   (1201) AATAACTGGTCTGGTTATTCTGGTATTTTCTCGGTTGAAGGCAAAAGCTG
SEQ ID NO:11  (1201) AATAACTGGTCTGGTTATTCTGGTATTTTCTCGGTTGAAGGCAAAAGCTG
                     1251                                                1300
SEQ ID NO:7   (1251) TATTAATAGGTGTTTTTATGGGAGTTGATAAGAGAGGGCCACAAGGACA
SEQ ID NO:9   (1251) TATTAATAGGTGTTTTTATGGGAGTTGATAAGAGAGGGCCACAAGGACA
SEQ ID NO:11  (1251) TATTAATAGGTGTTTTTATGGGAGTTGATAAGGGCGAGGGCCACAAGGACA
```

Figure 5L

```
                     1301                                              1350
SEQ ID NO:7   (1301) CTAGAGTATGGTGGACTTCAAATAGCAATTGTCGTATTTGTGGTACTTCT
SEQ ID NO:9   (1301) CTAGAGTATGGTGGACTTCAAATAGCAATTGTCGTATTTGTGGTACTTCT
SEQ ID NO:11  (1301) CTAGAGTATGGTGGACTTCAAATAGCAATTGTCGTATTTGTGGTACTTCT
                     1351                                              1400
SEQ ID NO:7   (1351) GGTACTATGGAACAGGCTCATGGCCTGATGGAGCGAATATTAACTTCAT
SEQ ID NO:9   (1351) GGTACTATGGAACAGGCTCATGGCCTGATGGAGCGAATATTAACTTCAT
SEQ ID NO:11  (1351) GGTACTATGGAACAGGCTCATGGCCTGATGGAGCGAATATTAACTTCAT
                     1401
SEQ ID NO:7   (1401) GCCTATATAA
SEQ ID NO:9   (1401) GCCTATATAA
SEQ ID NO:11  (1401) GCCTATATAA
```

Sequence identity
SEQ ID NO:7 v. SEQ ID NO:9:     100.0%
SEQ ID NO:7 v. SEQ ID NO:11:    99.9%
SEQ ID NO:9 v. SEQ ID NO:11:    99.9%

DNA sequence alignment of polynucleotide encoding NA protein of H3N8 and sequence identity

```
                     1                                                 50
SEQ ID NO:32  (1)    ATGAACCCAAATCAAAAGATAATAACCAATTGGATTGCATCATTGGGAT
SEQ ID NO:36  (1)    ATGAACCCAAATCAAAAGATAATAACCAATTGGATTGCATCATTGGGAT
SEQ ID NO:40  (1)    ATGAACCCAAATCAAAAGATAATAACCAATTGGATTGCATCATTGGGAT
SEQ ID NO:42  (1)    ATGAACCCAAATCAAAAGATAATAACCAATTGGATTGCATCATTGGGAT
                     51                                                100
SEQ ID NO:32  (51)   ATTAATCATTAATGTCATTCTCCATGTAGTCAGCATTATAGTAACAGTAC
SEQ ID NO:36  (51)   ATTAATCATTAATGTCATTCTCCATGTAGTCAGCATTATAGTAACAGTAC
SEQ ID NO:40  (51)   ATTAATCATTAATGTCATTCTCCATGTAGTCAGCATTATAGTAACAGTAC
SEQ ID NO:42  (51)   ATTAATCATTAATGTCATTCTCCATGTAGTCAGCATTATAGTAACAGTAC
                     101                                               150
SEQ ID NO:32  (101)  TGGTCCTCAATAACAATAGAACAGATCTGAACTACAAAGGGACGATCATA
SEQ ID NO:36  (101)  TGGTCCTCAATAACAATAGAACAGATCTGAACTACAAAGGGACGATCATA
SEQ ID NO:40  (101)  TGGTCCTCAATAACAATAGAACAGATCTGAACTACAAAGGGACGATCATA
SEQ ID NO:42  (101)  TGGTCCTCAATAACAATAGAACAGATCTGAACTACAAAGGGACGATCATA
                     151                                               200
SEQ ID NO:32  (151)  AGAGAATACAATGAAACAGTAAGAGTAGAAAAACTTACTCAATGGTACAA
SEQ ID NO:36  (151)  AGAGAATACAATGAAACAGTAAGAGTAGAAAAACTTACTCAATGGTACAA
SEQ ID NO:40  (151)  AGAGAATACAATGAAACAGTAAGAGTAGAAAAACTTACTCAATGGTACAA
SEQ ID NO:42  (151)  AGAGAATACAATGAAACAGTAAGAGTAGAAAAACTTACTCAATGGTACAA
                     201                                               250
SEQ ID NO:32  (201)  CACCAGTACAACCAAGTACATAGAGAGACCTTCAAATGAATATACATGA
SEQ ID NO:36  (201)  CACCAGTACAACCAAGTACATAGAGAGACCTTCAAATGAATATACATGA
SEQ ID NO:40  (201)  CACCAGTACAACCAAGTACATAGAGAGACCTTCAAATGAATACTACATGA
SEQ ID NO:42  (201)  CACCAGTACAACCAAGTACATAGAGAGACCTTCAAATGAATATACATGA
                     251                                               300
SEQ ID NO:32  (251)  AAACACTGAACCACTTTGTGAGGCCAAGGCTTTGCACCATTTTCCAAA
SEQ ID NO:36  (251)  AAACACTGAACCACTTTGTGAGGCCAAGGCTTTGCACCATTTTCCAAA
SEQ ID NO:40  (251)  ATAACACTGAACCACTTTGTGAGGCCAAGGCTTTGCACCATTTTCCAAA
SEQ ID NO:42  (251)  AAACACTGAACCACTTTGTGAGGCCAAGGCTTTGCACCATTTTCCAAA
```

Figure 5M

```
                        301                                                350
SEQ ID NO:32    (301)   GATAATGGAATACGAATTGGGTCGACAGGCCATGTTTTTGTGATAAGAGA
SEQ ID NO:36    (301)   GATAATGGAATACGAATTGGGTCGACAGGCCATGTTTTTGTGATAAGAGA
SEQ ID NO:40    (301)   GATAATGGAATACGAATTGGGTCGACAGGCCATGTTTTTGTGATAAGAGA
SEQ ID NO:42    (301)   GATAATGGAATACGAATTGGGTCGACAGGCCATGTTTTTGTGATAAGAGA
                        351                                                400
SEQ ID NO:32    (351)   ACCTTTGTATCATGTTTCCCTCAGAATGTAGAACCTTTTTCCTCACAC
SEQ ID NO:36    (351)   ACCTTTGTATCATGTTTCCCTCAGAATGTAGAACCTTTTTCCTCACAC
SEQ ID NO:40    (351)   ACCTTTGTATCATGTTGCCCTCAGAATGTAGAACCTTTTTCCTCACAC
SEQ ID NO:42    (351)   ACCTTTGTATCATGTTTCCCTCAGAATGTAGAACCTTTTTCCTCACAC
                        401                                                450
SEQ ID NO:32    (401)   AGGGCTCATTACTCAATGACAAACATTCTAACGGCACAATAAAGGATCGA
SEQ ID NO:36    (401)   AGGGCTCATTACTCAATGACAAACATTCTAACGGCACAATAAAGGATCGA
SEQ ID NO:40    (401)   AGGGCTCATTACTCAATGACAAACATTCTAACGGCACAATAAAGGATCGA
SEQ ID NO:42    (401)   AGGGCTCATTACTCAATGACAAACATTCTAACGGCACAATAAAGGATCGA
                        451                                                500
SEQ ID NO:32    (451)   AGTCCGTATAGGACTTTGATGAGTGTCAAAATAGGGCAATCACCTAATGT
SEQ ID NO:36    (451)   AGTCCGTATAGGACTTTGATGAGTGTCAAAATAGGGCAATCACCTAATGT
SEQ ID NO:40    (451)   AGTCCGTATAGGACTTTGATGAGTGTCAAAATAGGGCAATCACCTAATGT
SEQ ID NO:42    (451)   AGTCCGTATAGGACTTTGATGAGTGTCAAAATAGGGCAATCACCTAATGT
                        501                                                550
SEQ ID NO:32    (501)   ATATCAAGCTAGATTTGAATCGGTGGCATGGTCAGCAACAGCATGCCATG
SEQ ID NO:36    (501)   ATATCAAGCTAGATTTGAATCGGTGGCATGGTCAGCAACAGCATGCCATG
SEQ ID NO:40    (501)   ATATCAAGCTAGATTTGAATCGGTGGCATGGTCAGCAACAGCATGCCATG
SEQ ID NO:42    (501)   ATATCAAGCTAGATTTGAATCGGTGGCATGGTCAGCAACAGCATGCCATG
                        551                                                600
SEQ ID NO:32    (551)   ATGGAAAAAATGGATGACAGTTGGAGTCACAGGCCCGACAATCAAGCA
SEQ ID NO:36    (551)   ATGGAAAAAATGGATGACAGTTGGAGTCACAGGCCCGACAATCAAGCA
SEQ ID NO:40    (551)   ATGGAAAAAATGGATGACAGTTGGAGTCACAGGCCCGACAATCAAGCA
SEQ ID NO:42    (551)   ATGGAAAAAATGGATGACAGTTGGAGTCACAGGCCCGACAATCAAGCA
                        601                                                650
SEQ ID NO:32    (601)   ATTGCAGTAGTGAACTATGGAGGTGTTCCGGTTGATATTATTAATTCATG
SEQ ID NO:36    (601)   ATTGCAGTAGTGAACTATGGAGGTGTTCCGGTTGATATTATTAATTCATG
SEQ ID NO:40    (601)   ATTGCAGTAGTGAACTATGGAGGTGTTCCGGTTGATATTATTAATTCATG
SEQ ID NO:42    (601)   ATTGCAGTAGTGAACTATGGAGGTGTTCCGGTTGATATTATTAATTCATG
                        651                                                700
SEQ ID NO:32    (651)   GGCAGGGATATTTTAAGAACCCAAGAGTCATCATGCACCTGCATTAAAG
SEQ ID NO:36    (651)   GGCAGGGATATTTTAAGAACCCAAGAGTCATCATGCACCTGCATTAAAG
SEQ ID NO:40    (651)   GGCAGGGATATTTTAAGAACCCAAGAGTCATCATGCACCTGCATTAAAG
SEQ ID NO:42    (651)   GGCAGGGATATTTTAAGAACCCAAGAGTCATCATGCACCTGCATTAAAG
                        701                                                750
SEQ ID NO:32    (701)   GAGACTGTTATTGGGTAATGACTGATGGACCGGCAAATAGGCAAGCTGAA
SEQ ID NO:36    (701)   GAGACTGTTATTGGGTAATGACTGATGGACCGGCAAATAGGCAAGCTGAA
SEQ ID NO:40    (701)   GAGACTGTTATTGGGTAATGACTGATGGACCGGCAAATAGGCAAGCTGAA
SEQ ID NO:42    (701)   GAGACTGTTATTGGGTAATGACTGATGGACCGGCAAATAGGCAAGCTGAA
                        751                                                800
SEQ ID NO:32    (751)   TATAGGATATTCAAAGCAAAAGATGGAAGAGTAATTGGGCAAACTGATAT
SEQ ID NO:36    (751)   TATAGGATATTCAAAGCAAAAGATGGAAGAGTAATTGGGCAAACTGATAT
SEQ ID NO:40    (751)   TATAGGATATTCAAAGCAAAAGATGGAAGAGTAATTGGGCAAACTGATAT
SEQ ID NO:42    (751)   TATAGGATATTCAAAGCAAAAGATGGAAGAGTAATTGGGCAAACTGATAT
```

Figure 5N

```
                         801                                                850
SEQ ID NO:32    (801)    AAGTTTCAATGGGGGACACATAGAGGAGTGTTCTTGTTACCCCAATGAAG
SEQ ID NO:36    (801)    AAGTTTCAATGGGGGACACATAGAGGAGTGTTCTTGTTACCCCAATGAAG
SEQ ID NO:40    (801)    AAGTTTCAATGGGGGACACATAGAGGAGTGTTCTTGTTACCCCAATGAAG
SEQ ID NO:42    (801)    AAGTTTCAATGGGGGACACATAGAGGAGTGTTCTTGTTACCCCAATGAAG
                         851                                                900
SEQ ID NO:32    (851)    GGAAGGTGGAATGCATATGCAGGGACAATTGGACTGGAACAAAGAGACCA
SEQ ID NO:36    (851)    GGAAGGTGGAATGCATATGCAGGGACAATTGGACTGGAACAAAGAGACCA
SEQ ID NO:40    (851)    GGAAGGTGGAATGCATATGCCAGGGACAATTGGACTGGAACAAATAGACCA
SEQ ID NO:42    (851)    GGAAGGTGGAATGCATATGCAGGGACAATTGGACTGGAACAAAGAGACCA
                         901                                                950
SEQ ID NO:32    (901)    ATTCTGGTAATATCTTCTGATCTATGGTACACAGTTGGATATTTGTGTGC
SEQ ID NO:36    (901)    ATTCTGGTAATATCTTCTGATCTATGGTACACAGTTGGATATTTGTGTGC
SEQ ID NO:40    (901)    ATTCTGGTAATATCTTCTGATCTATGGTACACAGTTGGATATTTGTGTGC
SEQ ID NO:42    (901)    ATTCTGGTAATATCTTCTGATCTATGGTACACAGTTGGATATTTGTGTGC
                         951                                                1000
SEQ ID NO:32    (951)    TGGCATTCCCACTGACACGCCTAGGGGAGAGGATAGTCAATTCACAGGCT
SEQ ID NO:36    (951)    TGGCATTCCCACTGACACGCCTAGGGGAGAGGATAGTCAATTCACAGGCT
SEQ ID NO:40    (951)    TGGCATTCCCACTGACACTCCTAGGGGAGAGGATAGTCAATTCACAGGCT
SEQ ID NO:42    (951)    TGGCATTCCCACTGACACGCCTAGGGGAGAGGATAGTCAATTCACAGGCT
                         1001                                               1050
SEQ ID NO:32    (1001)   CATGTACAAGTCCTTTGGGAAATAAGGGATACGGTGTAAAAGGCTTCGGG
SEQ ID NO:36    (1001)   CATGTACAAGTCCTTTGGGAAATAAGGGATACGGTGTAAAAGGCTTCGGG
SEQ ID NO:40    (1001)   CATGTACAAGTCCTTTGGGAAATAAGGGATACGGTGTAAAAGGCTTCGGG
SEQ ID NO:42    (1001)   CATGTACAAGTCCTTTGGGAAATAAGGGATACGGTGTAAAAGGCTTCGGG
                         1051                                               1100
SEQ ID NO:32    (1051)   TTTCGACAAGGAACTGACGTATGGGCCGGAAGGACAATTAGTAGAACTTC
SEQ ID NO:36    (1051)   TTTCGACAAGGAACTGACGTATGGGCCGGAAGGACAATTAGTAGAACTTC
SEQ ID NO:40    (1051)   TTTCGACAAGGAACTGACGTATGGGCCGGAAGGACAATTAGTAGAACTTC
SEQ ID NO:42    (1051)   TTTCGACAAGGAACTGACGTATGGGCCGGAAGGACAATTAGTAGAACTTC
                         1101                                               1150
SEQ ID NO:32    (1101)   AAGATCAGGATTCGAAATAATAAAAATCAGGAATGGCTGGACACAGAATA
SEQ ID NO:36    (1101)   AAGATCAGGATTCGAAATAATAAAAATCAGGAATGGTTGGACACAGAAAA
SEQ ID NO:40    (1101)   AAGATCAGGATTCGAAATAATAAAAATCAGGAATGGTTGGACACAGAACA
SEQ ID NO:42    (1101)   AAGATCAGGATTCGAAATAATAAAAATCAGGAATGGTTGGACACAGAAAA
                         1151                                               1200
SEQ ID NO:32    (1151)   GTAAGGACCAAATCAGGAGGCAAGTGATTATCGATGACCTAAATTGGTCA
SEQ ID NO:36    (1151)   GTAAGGACCAAATCAGGAGGCAAGTGATTATCGATGACCGAAATTGGTCA
SEQ ID NO:40    (1151)   GTAAGGACCAAATCAGGAGGCAAGTGATTATCGATGACCGAAATTGGTCA
SEQ ID NO:42    (1151)   GTAAGGACCAAATCAGGAGGCAAGTGATTATCGATGACCGAAATTGGTCA
                         1201                                               1250
SEQ ID NO:32    (1201)   GGATATAGCGGTTCTTTCACATTGCCGGTTGAATTGACAAAAAAGGGATG
SEQ ID NO:36    (1201)   GGATATAGCGGTTCTTTCACATTGCCGGTTGAATTGACAAAAAAGGGATG
SEQ ID NO:40    (1201)   GGATATAGCGGTTCTTTCACATTGCCGGTTGAACTGACAAAAAAGGGATG
SEQ ID NO:42    (1201)   GGATATAGCGGTTCTTTCACATTGCCGGTTGAATTGACAAAAAAGGGATG
                         1251                                               1300
SEQ ID NO:32    (1251)   TTTGGTCCCCGTGTTCTGGGTTGAAATGATTAGAGGTAAACCTGAAGAAA
SEQ ID NO:36    (1251)   TTTGGTCCCCGTGTTCTGGGTTGAAATGATTAGAGGTAAACCTGAAGAAA
SEQ ID NO:40    (1251)   TTTGGTCCCCGTGTTCTGGGTTGAAATGATTAGAGGTAAACCTGAAGAAA
SEQ ID NO:42    (1251)   TTTGGTCCCCGTGTTCTGGGTTGAAATGATTAGAGGTAAACCTGAAGAAA
```

Figure 5O

```
                      1301                                              1350
SEQ ID NO:32  (1301)  CAACAATATGGACCTCTAGCAGCTCCATTGTGATGTGTGGAGTAGATCAT
SEQ ID NO:36  (1301)  CAACAATATGGACCTCTAGCAGCTCCATTGTGATGTGTGGAGTAGATCAT
SEQ ID NO:40  (1301)  CAACAATATGGACCTCTAGCAGCTCCATTGTGATGTGTGGAGTAGATCAT
SEQ ID NO:42  (1301)  CAACAATATGGACCTCTAGCAGCTCCATTGTGATGTGTGGAGTAGATCAT
                      1351                                              1400
SEQ ID NO:32  (1351)  AAAATTGCCAGTTGGTCATGGCACGATGGAGCXATTCTTCCCTTTGACAT
SEQ ID NO:36  (1351)  AAAATTGCCAGTTGGTCATGGCACGATGGAGCXATTCTTCCCTTTGACAT
SEQ ID NO:40  (1351)  AAAATTGCCAGTTGGTCATGGCACGATGGAGCTATTCTTCCCTTTGACAT
SEQ ID NO:42  (1351)  AAAATTGCCAGTTGGTCATGGCACGATGGAGCXATTCTTCCCTTTGACAT

1401
SEQ ID NO:32  (1401)  CGATAAGATG
SEQ ID NO:36  (1401)  CGATAAGATG
SEQ ID NO:40  (1401)  CGATAAGATG
SEQ ID NO:42  (1401)  CGATAAGATG
```

Sequence identity
SEQ ID NO:32 v. SEQ ID NO:36:    99.5%
SEQ ID NO:32 v. SEQ ID NO:40:    97.6%
SEQ ID NO:32 v. SEQ ID NO:42:    99.6%
SEQ ID NO:36 v. SEQ ID NO:40:    98.1%
SEQ ID NO:36 v. SEQ ID NO:42:    99.9%
SEQ ID NO:40 v. SEQ ID NO:42:    98.0%

Protein sequence alignment of NA protein of H3N8 and sequence identity

```
                     1                                                  50
SEQ ID NO:33   (1)   MNPNQKIIAIGSASLGILIINXILRVVSIVTVLVLNSNRTDLNXKGTII
SEQ ID NO:37   (1)   MNPNQKIIAIGSASLGILIINXILRVVSIVTVLVLNSNRPTDLNXKGTII
SEQ ID NO:41   (1)   MNPNQKIIAIGFASLGILIINXILRVVSIVTVLVLNSNRTDLNYKGTII
                     51                                                 100
SEQ ID NO:33  (51)   REYNETVRVEKLTQWYNXSTTKYIERPSNEYYMNNTEPLCEAQGFAPFSK
SEQ ID NO:37  (51)   REYNETVRVEKLTQWYNXSTXKYIERPSNEYYMNNTEPLCEAQGFAPFSK
SEQ ID NO:41  (51)   REYNETVRVEKLTQWYNTSXKYIERPSNEYYMNNTEPLCEAQGFAPFSK
                     101                                                150
SEQ ID NO:33 (101)   DNGIRIGSRGHVFVIREPFVSCSPSECRTFFLTQGSLLNDKHSNGTIKDR
SEQ ID NO:37 (101)   DNGIRIGSRGHVFVIREPFVSCSPSECRTFFLTQGSLLNDKHSNGTIKDR
SEQ ID NO:41 (101)   DNGIRIGSRGHVFVIREPFVSCSPSECRTFFLTQGSLLNDKHSNGTIKDR
                     151                                                200
SEQ ID NO:33 (151)   SPYRTLMSVKIGQSPNVYQAXFESVAWSATACHDGKKWMTVGVTGPDNQA
SEQ ID NO:37 (151)   SPYRTLMSVKIGQSPNVYQAXFESVAWSATACHDGKKWMTVGVTGPDNQA
SEQ ID NO:41 (151)   SPYRTLMSVKIGQSPNVYQAXFESVAWSATACHDGKKWMTVGVTGPDNQA
                     201                                                250
SEQ ID NO:33 (201)   IAVVNYGGVPVDIINSWAGDILRTQESSCTCIKGDCYWVMTDGPANKQAX
SEQ ID NO:37 (201)   IAVVNYGGVPVDIINSWAGDILRTQESSCTCIKGDCYWVMTDGPANKQAX
SEQ ID NO:41 (201)   IAVVNYGGVPVDIINSWAGDILRTQESSCTCIKGDCYWVMTDGPANKQAE
```

Figure 5P

```
                      251                                             300
SEQ ID NO:33   (251)  [sequence]
SEQ ID NO:37   (251)  [sequence]
SEQ ID NO:41   (251)  [sequence]
                      301                                             350
SEQ ID NO:33   (301)  [sequence]
SEQ ID NO:37   (301)  [sequence]
SEQ ID NO:41   (301)  [sequence]
                      351                                             400
SEQ ID NO:33   (351)  [sequence]
SEQ ID NO:37   (351)  [sequence]
SEQ ID NO:41   (351)  [sequence]
                      401                                             450
SEQ ID NO:33   (401)  [sequence]
SEQ ID NO:37   (401)  [sequence]
SEQ ID NO:41   (401)  [sequence]
                      451            470
SEQ ID NO:33   (451)  [sequence]
SEQ ID NO:37   (451)  [sequence]
SEQ ID NO:41   (451)  [sequence]
```

Sequence identity
SEQ ID NO:33 v. SEQ ID NO:37:   99.6%
SEQ ID NO:33 v. SEQ ID NO:41:   98.3%
SEQ ID NO:37 v. SEQ ID NO:41:   98.7%

Sequence identity between NA proteins of H3N2 and H3N8

| SEQ ID NO: | 8 | 10 | 12 | 33 | 37 | 41 |
|---|---|---|---|---|---|---|
| 8 | | 100% | 100% | 43.5% | 43.8% | 43.7% |
| 10 | | | 100% | 43.5% | 43.8% | 43.7% |
| 12 | | | | 44.1% | 44.4% | 44.3% |
| 33 | | | | | 99.6% | 98.3% |
| 37 | | | | | | 98.7% |
| 41 | | | | | | |

INACTIVATED CANINE INFLUENZA VACCINES AND METHODS OF MAKING AND USES THEREOF

CROSS-REFERENCE TO RELATED APPLICATIONS

This application claims priority to U.S. provisional application 62/185,266 filed on Jun. 26, 2015 and U.S. provisional application 62/298,285 filed on Feb. 22, 2016.

FIELD OF THE INVENTION

The present invention relates to new canine influenza virus strains, and vaccines and compositions. The present invention also relates to reagents and methods allowing their detection, methods of vaccination as well as methods of producing these reagents and vaccines.

BACKGROUND OF THE INVENTION

Influenza virus is a member of Orthomyxoviridae family (Murphy and Webster, Orthomyxoviruses, Fields Virology, Third Edition, vol. 1, pp. 1397-1445, 1996). There are three types of influenza viruses designated A, B, and C. The influenza virion contains a segmented negative-sense RNA genome. The influenza virion includes the following proteins: hemagglutinin (HA), neuraminidase (NA), matrix (M1), proton ion-channel protein (M2), nucleoprotein (NP), polymerase basic protein 1 (PB1), polymerase basic protein 2 (PB2), polymerase acidic protein (PA), and nonstructural protein 2 (NS2) proteins. The NP and the matrix protein M1 are used to classify the influenza virus into group A, B or C.

The HA and NA proteins are envelope glycoproteins. The HA protein is responsible for virus attachment and penetration of the viral particles into the cell and contains the major immunodominant epitopes for virus neutralization and protective immunity. Both HA and NA proteins are considered the most important components for prophylactic influenza vaccines. To date, eighteen different HA subtypes and eleven different NA subtypes have been identified (Tong et al., 2013, PLoS Pathogens, Vol. 9 (10), New World Bats harbor diverse influenza A viruses).

Globally, influenza is the most economically significant respiratory disease in humans, pigs, horses and poultry. Influenza virus is known for its continuous genetic and antigenic changes, which impede effective control of the virus. Of particular concern for prevention of epidemics and pandemics is the emergence of a new subtype of the virus by genetic re-assortment or inter-species transmission.

Recently, influenza outbreaks have occurred in species, e.g., feline and canine, which historically do not carry influenza virus. During 2004 and 2005, outbreaks of respiratory disease in racing greyhounds caused by infection with influenza virus occurred in Florida, eastern and western Iowa, and Texas. Molecular and antigenic analyses of three influenza viruses isolated from outbreaks of severe respiratory disease in racing greyhounds revealed that they are closely related to H3N8 equine influenza virus (Crawford et al., Science, 2005, 310 (5747):482-485; PLOS Pathogens, 2014, 10 (10), e1004455).

U.S. Pat. No. 8,246,962 and Song et al. (2008 Emerg. Infect. Dis., 2008, 14, pp. 741-746) reported an infection of an H3N2 subtype influenza virus in a pet dog in the Republic of Korea. The case was caused by a H3N2 avian-origin canine influenza virus (CIV), which infected dogs successfully through nasal inoculation or contact (respiratory fluid exchange) under experimental conditions.

Li et. al. (Infection, Genetics and Evolution, 2010, 10 (8): 1286-1288) reported four sporadic cases of H3N2 canine influenza in Southern China, which were identified from sick dogs from May 2006 to October 2007. The evolutionary analysis showed that all eight segments of these four viruses are avian-origin and phylogenetically closely related to the H3N2 canine influenza viruses reported earlier in South Korea.

H3N2 canine influenza can be transmitted to cats and cause severe respiratory disease in cats (Song et al., J. Gen. Virol. 2011, 92:23050-2355).

On Mar. 26, 2015, the Chicago Tribune reported an outbreak of canine influenza caused by a new strain of virus identified as H3N2. As of today, the virus has now been detected in dogs in 30 states, including Illinois, Ohio, Wisconsin, Indiana, Iowa, Minnesota, Michigan, California, Massachusetts, Texas, New Jersey, South Dakota, and Georgia.

There were no vaccines available in the U.S. for H3N2 CIV as of June 2015. The H3N8 CIV vaccines currently marketed in the U.S. are unlikely to protect dogs against H3N2 CIV due to the genetic divergence in the HA proteins encoded by the two virus subtypes. Although both viruses encode H3 subtype HAs, the proteins only share about 77% sequence identity at the amino acid level.

Accordingly, there is an urgent need for an effective vaccine against H3N2 influenza infection in canines and felines.

SUMMARY OF THE INVENTION

The present invention relates to an inactivated/killed canine influenza virus (CIV) composition or vaccine. In particular, the invention provides the canine influenza virus strains under the ATCC deposit Nos. PTA-122265 and PTA-122266, or any descendant or progeny of the strains. The canine influenza viruses are H3N2 strains isolated in the US.

In a particular embodiment, the inactivated vaccines comprise an adjuvant. The adjuvant may be any substance which increases and/or augments the elicited immune response, as compared to inactivated vaccine alone.

The invention also provides a polyvalent composition or vaccine that is effective to protect animals against a variety of CIV infections. In particular, the invention provides a polyvalent composition or vaccine comprising an inactivated H3N2 CIV and inactivated H3N8 CIV.

Methods for protection in animals against CIV infections and for reducing viral shedding in CIV infected animals are provided.

The invention also offers the possibility of diagnosing the presence of the canine influenza virus according to the invention in dogs. Its subject is therefore diagnostic tests and methods relating thereto using reagents which will be described below.

Kits comprising the inactivated canine Influenza strains and instructions for use are also provided.

These and other embodiments are disclosed or are obvious from and encompassed by, the following Detailed Description.

BRIEF DESCRIPTION OF THE DRAWINGS

The following detailed description, given by way of example, and which is not intended to limit the invention to specific embodiments described, may be understood in conjunction with the accompanying figures, incorporated herein by reference, in which:

FIGS. 1A-B are tables showing the SEQ ID NO assigned to each DNA and protein sequence.

Figure 2:
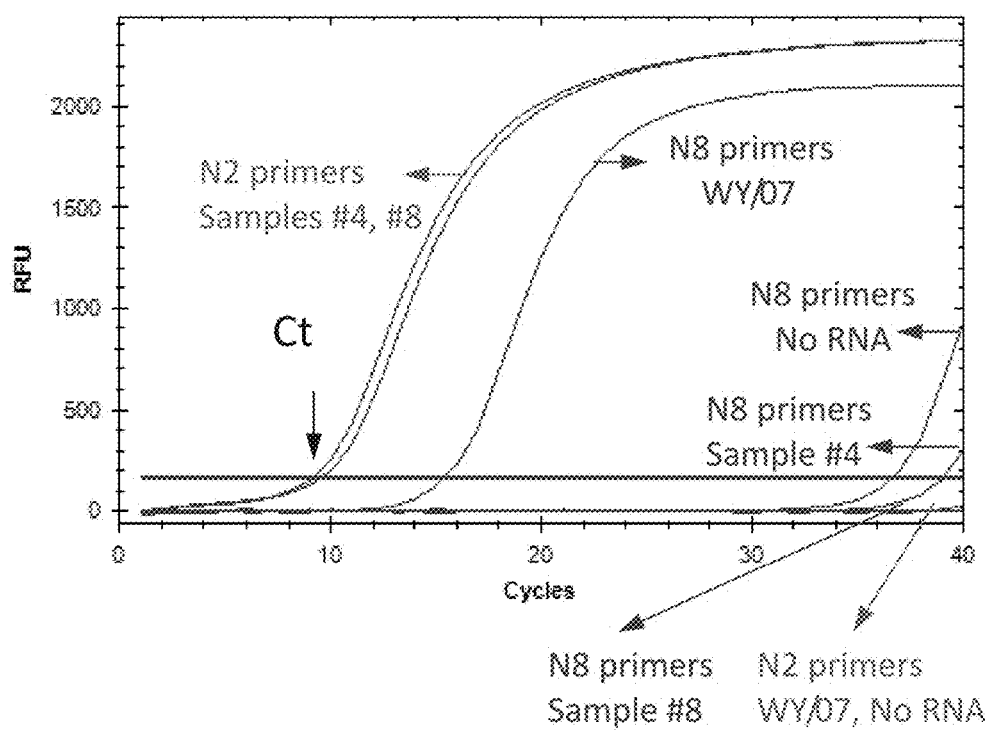
FIG. 2 depicts real-time RT-PCR genotyping of CIVs.

FIG. 5A-5P provide the sequence alignments of DNA and proteins.

DETAILED DESCRIPTION

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle, buffalos), swine (e.g., pig), ovine (e.g., sheep), caprine (e.g., goats), camelids (e.g., lamas), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages.

The terms "polypeptide" and "protein" are used interchangeably herein to refer to a polymer of consecutive amino acid residues.

The term "nucleic acid", "nucleotide", and "polynucleotide" are used interchangeably and refer to RNA, DNA, cDNA, or cRNA and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA" or "genome" is used interchangeably and refers to the heritable genetic information of a host organism. The genomic DNA comprises the DNA of the nucleus (also referred to as chromosomal DNA) but also the DNA of the plastids (e.g., chloroplasts) and other cellular organelles (e.g., mitochondria). The genomic DNA or genome contemplated in the present invention also refers to the RNA of a virus. The RNA may be a positive strand or a negative strand RNA. The term "genomic DNA" contemplated in the present invention includes the genomic DNA containing sequences complementary to those described herein. The term "genomic DNA" also refers to messenger RNA (mRNA), complementary DNA (cDNA), and complementary RNA (cRNA).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; transcription terminators (in general the terminator is located within approximately 50 nucleotides downstream of the stop codon of the coding sequence or gene). Gene or polynucleotide also refers to a nucleic acid fragment that expresses mRNA or functional RNA, or encodes a specific protein, and which includes regulatory sequences.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an antigen, an epitope, a hapten, or any combination thereof. Alternately, the immunogen or antigen may comprise a toxin or antitoxin.

The term "immunogenic protein or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. For example, linear epitopes may be determined by e.g., concurrently synthesizing large numbers of peptides on solid supports, the peptides corresponding to portions of the protein molecule, and reacting the peptides with antibodies while the peptides are still attached to the supports. Similarly, conformational epitopes are readily identified by determining spatial conformation of amino acids such as by, e.g., x-ray crystallography and 2-dimensional nuclear magnetic resonance.

The term "immunogenic protein or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or lowered pathogen loads in the infected host.

As used herein, the term "inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with thimerosal, formalin, BPL (beta-propiolactone) or BEI (binary ethylenimine), sonication, radiation, heat or any other conventional means sufficient to prevent replication or growth of the organism while maintaining its immunogenicity.

The terms "polyvalent vaccine or composition", "combination or combo vaccine or composition" and "multivalent vaccine or composition" are used interchangeably to refer to a composition or vaccine containing more than one composition or vaccines. The polyvalent vaccine or composition may contain two, three, four or more compositions or vaccines. The polyvalent vaccine or composition may comprise recombinant viral vectors, active or attenuated or inactivated/killed wild-type viruses, or a mixture of recombinant viral vectors and wild-type viruses in active or attenuated or killed forms.

In one embodiment, the present invention encompasses a novel inactivated/killed CIV composition or vaccine. The CIV strains are the H3N2 subtype newly identified in the USA. The inactivation may be the chemical inactivation that produces enumerable structural changes, including for example, formation of new chemical bonds via chemical crosslinking, irreversible chemical alteration of the nucleic acid and protein coat.

In another embodiment, the present invention provides a bivalent composition or vaccine comprising an inactivated H3N2 CIV and inactivated H3N8 CIV.

One embodiment of the invention provides the genomic DNA and gene sequences, and encoded protein sequences of CIV H3N2 and H3N8 strains.

In another embodiment, the invention provides the sequences for HA proteins or antigens. In one aspect of the embodiment, the HA proteins have the polypeptide sequence as set forth in SEQ ID NO:2, 4, 6, 31, 35, and 39. In another aspect, the HA proteins have at least 70%, 75%, 80%, 85%, 90%, 95%, 96%, 97%, 98%, 99%, 99.1%. 99.2%, 99.3%, 99.4%, 99.5%, 99.6%, 99.7%, 99.8% or 99.9% sequence identity to a polypeptide having the sequence as set forth in SEQ ID NO:2, 4, 6, 31, 35, and 39. In yet another aspect, the HA proteins are encoded by the polynucleotides having at least 70%, 75%, 80%, 85%, 90%, 95%, 96%, 97%, 98%, 99%, 99.1%. 99.2%, 99.3%, 99.4%, 99.5%, 99.6%, 99.7%, 99.8% or 99.9% sequence identity to a polynucleotide having the sequence as set forth in SEQ ID NO:1, 3, 5, 30, 34 and 38.

In another embodiment, the invention provides the sequences for NA proteins or antigens. In one aspect of the embodiment, the NA proteins have the polypeptide sequence as set forth in SEQ ID NO:8, 10, 12, 33, 37 and 41. In another aspect, the NA proteins have at least 70%, 75%, 80%, 85%, 90%, 95%, 96%, 97%, 98%, 99%, 99.1%. 99.2%, 99.3%, 99.4%, 99.5%, 99.6%, 99.7%, 99.8% or 99.9% sequence identity to a polypeptide having the sequence as set forth in SEQ ID NO:8, 10, 12, 33, 37 and 41. In yet another aspect, the NA proteins are encoded by the polynucleotides having at least 70%, 75%, 80%, 85%, 90%, 95%, 96%, 97%, 98%, 99%, 99.1%. 99.2%, 99.3%, 99.4%, 99.5%, 99.6%, 99.7%, 99.8% or 99.9% sequence identity to a polynucleotide having the sequence as set forth in SEQ ID NO:7, 9, 11, 32, 36, 40 and 42.

In one embodiment, the CIV stains may comprise an HA gene encoding an HA protein aforementioned. In another embodiment, the CIV strains may comprise an NA gene encoding an NA protein aforementioned.

In one embodiment, the invention provides CIV strains under the ATCC deposit numbers PTA-122265 and PTA-122266, or any parent, descendant or progeny of the deposited strains.

In one embodiment, the composition or vaccine of the invention includes a live CIV H3N2 strain. The CIV H3N2 strains were initially isolated from 1-14 year old dogs with symptoms of severe respiratory disorder in Illinois, USA. The strains were deposited at ATCC (American Type Culture Collection; 10801 University Boulevard, Manassas, VA 20110) on Jun. 25, 2015 and were accorded Accession Nos. PTA-122265 and PTA-122266.

In another embodiment, the present invention contemplates preparation and isolation of a progeny or descendant of a CIV H3N2 virus that has been deposited on Jun. 25, 2015 at ATCC under the Accession Numbers PTA-122265 and PTA-122266. The invention therefore extends to CIV H3N2 virus strains which are derived from the deposited strains through propagation or multiplication in an identical or divergent form, in particular descendants which possess the essential characteristics of the deposited strains. Upon continued propagation, the strains may acquire mutations most of which will not alter the properties of these strains significantly. The progeny or descendant may comprise a polynucleotide encoding an HA protein having at least 99.6% sequence identity to the sequence as set forth in SEQ ID NO:2, 4, or 6, or a polynucleotide encoding an NA protein having the sequence as set forth in SEQ ID NO:8, 10 or 12. The progeny or descendant may comprise a polynucleotide encoding an HA protein having at least 99.0% or 99.6% sequence identity to the sequence as set forth in SEQ ID NO:2, 4, or 6 and the HA protein may differ at amino acid position 62, 219 or 249 of a full-length HA0 protein (i.e. uncleaved and containing the signal peptide). The amino acid at position 62, 219, or 249 of a full-length HA0 protein may be any amino acid denoted in Table 1 below.

TABLE 1

Amino Acid

| Abbreviation | Amino Acid | Abbreviation | Amino Acid |
|---|---|---|---|
| A (Ala) | Alanine | L (Leu) | Leucine |
| R (Arg) | Arginine | K (Lys) | Lysine |
| D (Asp) | Aspartic acid | M (Met) | Methionine |
| N (Asn) | Asparagine | F (Phe) | Phenylalanine |
| C (Cys) | Cysteine | P (Pro) | Proline |
| Q (Gln) | Glutamine | S (Ser) | Serine |
| E (Glu) | Glutamic acid | T (Thr) | Threonine |
| G (Gly) | Glycine | W (Trp) | Tryptophan |
| H (His) | Histidine | Y (Tyr) | Tyrosine |
| I (Ile) | Isoleucine | V (Val) | Valine |

The inactivated pathogen or organism can be concentrated by conventional concentration techniques, in particular by ultrafiltration, and/or purified by conventional purification means, in particular using chromatography techniques including, but not limited to, gel-filtration or by ultrafiltration. As used herein, the term "immunogenicity" means capable of producing an immune response in a host animal against an antigen or antigens. This immune response forms the basis of the protective immunity elicited by a vaccine against a specific infectious organism.

Further, methods which are well known to those skilled in the art can be used to determine protein purity or homogeneity, such as polyacrylamide gel electrophoresis of a sample, followed by visualizing a single polypeptide band on a staining gel. Higher resolution may be determined using HPLC or other similar methods well known in the art.

In one embodiment, the invention provides for the administration of a therapeutically effective amount of a vaccine or composition for the delivery and expression of a CIV H3N2 antigen in a target cell. In another embodiment, the invention provides for the administration of a therapeutically effective amount of a vaccine or composition for the delivery and expression of CIV H3N2 and CIV H3N8 antigens in a target cell. Determination of the therapeutically effective amount is routine experimentation for one of ordinary skill in the art. In one embodiment, the vaccine or composition comprises an inactivated/killed CIV H3N2 strains, and a pharmaceutically or veterinarily acceptable carrier, adjuvant, vehicle or excipient. In another embodiment, the vaccine or composition comprises an inactivated/killed H3N2 CIV and inactivated/killed H3N8 CIV strains, and a pharmaceutically or veterinarily acceptable carrier, adjuvant, vehicle or excipient. In an embodiment, the pharmaceutically or veterinarily acceptable carrier, vehicle, adjuvant, or excipient facilitates transfection and/or improves preservation of the virus or protein.

The pharmaceutically or veterinarily acceptable carriers, adjuvants, vehicles, or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier, adjuvant, vehicle, or excipients that can be used for methods of this invention include, but are not limited to, poly-(L-glutamate) or polyvinylpyrrolidone. The pharmaceutically or veterinarily acceptable carrier, adjuvant, vehicle, or excipients may be any compound or combination of compounds facilitating the administration of the vector (or protein expressed from an inventive vector in vitro); the carrier, vehicle, adjuvant, or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

$$R_1-O-CH_2-CH-CH_2-\overset{+}{\underset{\underset{CH_3}{|}}{\overset{\overset{CH_3}{|}}{N}}}-R_2-X$$
$$\phantom{R_1-O-CH_2-}\underset{OR_1}{|}$$

in which $R_1$ is a saturated or unsaturated straight-chain aliphatic radical having 12 to 18 carbon atoms, $R_2$ is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr J. P., 1994, Bioconjugate Chemistry, 5, 382-389), to form DMRIE-DOPE.

The composition or vaccine mixture with the adjuvant is formed extemporaneously and contemporaneously with administration of the preparation or shortly before administration of the preparation; for instance, shortly before or prior to administration, the composition or vaccine-adjuvant mixture is formed, so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95:about 5 to about 5:about 95, more advantageously about 1:about 1, e.g., 1:1.

The immunogenic compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one ore more non-methylated CpG units (Klinman D. M. et al., Proc. Natl. Acad. Sci., USA, 1996, 93, 2879-2883; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, (5) cytokines, (6) aluminum hydroxide or aluminum phosphate or (7) saponin, (8) Dimethyldioctadecyl ammonium bromide (Vaccine Design p. 157), (9) Aridine (Vaccine Design p. 148) other adjuvants discussed in any document cited and incorporated by reference into the instant application, or (8) any combinations or mixtures thereof.

The oil in water emulsion (3), can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121. Some of the emulsions, such as TS6, TS7, TS8 and TS9 emulsions, are described in U.S. Pat. Nos. 7,608,279 and 7,371,395.

The polymers of acrylic or methacrylic acid (1) are preferably crosslinked, in particular with polyalkenyl ethers of sugars or polyalcohols. These compounds are known under the term carbomer (Pharmeuropa vol. 8, No. 2, June 1996). Persons skilled in the art can also refer to U.S. Pat. No. 2,909,462 describing such acrylic polymers crosslinked with a polyhydroxylated compound having at least 3 hydroxyl groups, preferably not more than 8, the hydrogen atoms of at least three hydroxyls being replaced with unsaturated aliphatic radicals having at least 2 carbon atoms. The preferred radicals are those containing 2 to 4 carbon atoms, e.g. vinyls, allyls and other ethylenically unsaturated groups. The unsaturated radicals may themselves contain other substituents, such as methyl. The products sold under the name CARBOPOL™ (BF Goodrich, Ohio, USA) are particularly appropriate. They are crosslinked with an allyl sucrose or with allylpentaerythritol. Among them, there may be mentioned CARBOPOL™ 974P, 934P and 971 P.

Among the copolymers of maleic anhydride and of alkenyl derivative, the EMA™ copolymers (Monsanto) which are copolymers of maleic anhydride and of ethylene, which are linear or crosslinked, for example crosslinked with divinyl ether, are preferred.

The proportions of adjuvant which are useful are well known and readily available to the one skilled in the art. By way of example, the concentration of polymers of acrylic or methacrylic acid or of anhydride maleic and alkenyl copolymers in the final vaccine composition will be from 0.01% to 1.5% W/V, more particularly from 0.05 to 1% W/V, preferably from 0.1 to 0.4% W/V.

In one embodiment, the adjuvant may include TS6 (U.S. Pat. No. 7,371,395), LR2, LR3 and LR4 (U.S. Pat. No. 7,691,368), TSAP (US20110129494), TRIGEN™ (Newport Labs), synthetic dsRNAs (e.g. poly-IC, poly-ICLC [HILTONOL®]), and MONTANIDE™ adjuvants (W/O, W/O/W, O/W, IMS and Gel; all produced by SEPPIC).

In yet another embodiment, the adjuvant may include interleukin-2 (IL-2), IL-12, interferon α (IFNα), polyinosinic and polycytidylic acid, and cytidine-phosphate-guanosine oligodeoxynucleotides (CpG ODN), which are known to significantly enhance CMI response to CIV vaccines (Vet. Immuno. and Immunopath. Vol. 129, Issues 1-2, 15 May 2009, Pages 1-13).

Optionally the vaccine used according to the method of the invention may contain a cytokine. The cytokine may be present as a protein or as a gene encoding this cytokine inserted into a recombinant viral vector. The cytokines may be selected among the pig cytokines.

In a specific embodiment, the pharmaceutical composition is directly administered in vivo. Advantageously, the pharmaceutical and/or therapeutic compositions and/or formulations according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

The composition or vaccine may contain a dose from about $10^2$ to about $10^{20}$, about $10^3$ to about $10^{18}$, about $10^4$ to about $10^{16}$, about $10^5$ to about $10^{12}$ VLPs (virus like particles) produced in vitro or in vivo from a viral vector, a plasmid, or baculovirus. The viral vector may be titrated based on any virus titration methods including, but not limited to, FFA (Focus Forming Assay) or FFU (Focus Forming Unit), $TCID_{50}$ (50% Tissue Culture Infective Dose), PFU (Plaque Forming Units), and $FAID_{50}$ (50% Fluorescent Antibody Infectious Dose), and the VLPs produced in vitro can be titrated by hemagglutination assay, ELISA, and electron microscopy. Other methods may also be applicable depending on the type of VLP.

The composition or vaccine may contain from about $10^{2.0}$ to about $10^{10.0}$ $TCID_{50}$/dose, from about $10^{4.5}$ to about $10^{8.0}$ $TCID_{50}$/dose and from about $10^{5.5}$ to about $10^{6.5}$ $TCID_{50}$/dose. The composition or vaccine may contain equivalent $TCID_{50}$ in the case of inactivated/killed composition or vaccine.

The dose volumes can be between about 0.1 and about 10 ml, between about 0.2 and about 5 ml.

When the antigen relates to hemagglutinin, such as inactivated influenza vaccines, the dosage is measured in hemagglutination units (HAUs). In an embodiment, the dosage may be from about 655 to about 65,500 HAU/dose.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Biojector or Vitaj et apparatus (Bioject, Oreg., USA)).

The composition or vaccine is administered to a dog or a cat (about six to eight-week old). A booster administration can be done if necessary around 2 to 8 weeks after the first administration.

Liquid jet needle-free injectors are devices performing injections of a certain amount of liquid under high pressure through a minute orifice. In an embodiment, the needle-free injection is a DERMA-VAC NF transdermal vaccinator system.

The volume of dose injected may be from about 0.1 ml to about 4.0 ml, about 0.1 ml to about 2 ml, about 0.1 ml to about 1 ml, from about 0.2 ml to about 0.8 ml, about 0.2 ml to about 0.5 ml. By definition, the volume of one dose means the total volume of vaccine administered at once to one animal.

Optionally, the administration can be repeated, as booster administration, at suitable intervals if necessary or desirable, e.g. from about 2 to about 8 weeks after the first administration, and preferably from about 2 to about 4 weeks after the first administration. A booster administration can also be repeated every 6 months or every year.

Another object of the invention is the use of an efficient amount of the composition or vaccine as described above and of an acceptable vehicle or diluent, for the preparation of a vaccine designed to be administered to an animal using a liquid jet needle-free injector as described above, and resulting in eliciting a safe and protective immune response against influenza infection.

In one embodiment of the invention, a prime-boost regimen can be employed, which is comprised of at least one primary administration and at least one booster administration using at least one common polypeptide, antigen, epitope or immunogen. Typically the same composition or vaccine is used as the primary administration and the boost. This administration protocol is called "prime-boost". However, different compositions or vaccines may be used as the prime administration and the boost.

Another object is a vaccination kit or set, comprising at least one vaccine vial containing the vaccine of the present invention, and operatively assembled to perform the administration of the vaccine to an animal of the canine family. Such vaccination kit or set is able to elicit a safe and protective immune response against influenza infection.

The invention also offers the possibility of diagnosing the presence of the CIV H3N2 or H3N8 strains according to the invention in dogs and cats. Its subject is therefore diagnostic tests and methods relating thereto using reagents which are described below.

A first reagent relates to the DNA sequences disclosed here and their fragments, which may be used as probes or primers in well-known hybridization or PCR (Polymerase Chain Reaction) techniques.

A second reagent relates to the polypeptides encoded by these sequences from the virus, or synthesized by the chemical route according to conventional techniques for peptide synthesis.

A third and fourth reagent relate to polyclonal and monoclonal antibodies which may be produced according to the customary techniques from the virus, the polypeptides or fragments, extracted or encoded by the DNA sequences.

These second, third and fourth reagents may be used in a diagnostic method, a subject of the invention, in which a test is carried out, on a sample of physiological fluid (blood, plasma, serum and the like) or a sample of tissue (ganglia, liver, lungs, kidneys and the like) obtained from a dog or a cat to be tested, for the presence of an antigen specific for a CIV H3N2 or H3N8 according to the invention, by seeking to detect either the antigen itself, or antibodies directed against this antigen.

The antigens and antibodies according to the invention may be used in any known laboratory diagnostic technique. However, it will be preferable to use them in techniques which can be used directly in the field by the veterinary doctor, the breeder or the owner of the animal. Persons skilled in the art have available a range of laboratory and field techniques and are therefore in the perfect position to adapt the use of this antigen and/or antibodies as diagnostic reagent(s).

The diagnostic techniques which will be used within the framework of the present invention are PCR and RT-PCR.

The subject of the invention is also a diagnostic kit comprising the reagents and/or polyclonal or monoclonal antibodies specific for H3N2 or H3N8 CIV antigen. The diagnostic kit may comprise primers designed based on the DNA sequences disclosed herein and reagents for PCR assay.

The method of diagnosing the presence of a CIV H3N2 or H3N8 strain using PCR comprises the steps of: a) generating a cDNA of the influenza virus genome isolated from an animal; b) exposing the cDNA to a primer pair comprising a forward primer and a reverse primer in a real-time polymerase chain reaction (PCR) to yield an amplicon, wherein the primer pair is specific to the H3N2 or H3N8 CIV genome; c) performing sequencing on the amplicon; and d) analyzing and comparing the sequence of the amplicon with known H3N2 or H3N8 CIV sequences.

The method of diagnosing the presence of an H3N2 or H3N8 CIV strain using real-time RT-PCR comprises the steps of: a) extracting genomic RNA from the influenza virus isolated from an animal; b) exposing the RNA to a primer pair comprising a forward and a reverse primer in a real-time reverse transcription-polymerase chain reaction (RT-PCR), wherein the primer pair is specific to the H3N2 or H3N8 CIV genome; c) analyzing and comparing the RT-PCR curve thereby characterizing the CIV strain.

The forward primer and reverse primer may be designed based on the HA and NA polynucleotide sequences disclosed herein. The primers may be the primers having the sequence as defined in SEQ ID NO:13-29 (FIG. 1 and Table 3).

The diagnostic techniques which will be used within the framework of the present invention include Western blotting, immunofluoroescence, ELISA and immunochromatography.

Accordingly, it is preferably sought to detect specific antibodies in the sample by an indirect test, by competition or by displacement. To do this, the antigen itself is used as diagnostic reagent, or a fragment of this antigen, conserving recognition of the antibodies. The labelling may be advantageously a labelling with peroxidase or a special labelling, preferably with colloidal gold.

It may also be desired to detect the antigen itself in the sample with the aid of a labelled antibody specific for this antigen. The labelling is advantageously as described above.

By antibody specific for the antigen which can be used in particular in competition or displacement or for the detection of the antigen itself, there is understood monoclonal or polyclonal antibodies specific for the antigen, fragments of these antibodies.

Another feature of the invention is the production of polyclonal or monoclonal antibodies specific for the antigen in accordance with the invention, it being possible for these antibodies to then be used in particular as diagnostic reagent for the detection of the antigen in a sample of physiological fluid or in a tissue sample, or even for the detection of antibodies present in such a sample or specimen. The invention also includes the immunologically functional fragments of these antibodies.

Antibodies can be prepared by the customary techniques. Reference may be made in particular to Antibodies, A Laboratory Manual, 2014, Cold Spring Harbor Laboratory, USA.

The subject of the invention is also a preparation, pure or partially pure, or even crude, of monoclonal or polyclonal antibodies specific for the antigen, especially mouse or rabbit antibodies.

The invention will now be further described by way of the following non-limiting examples.

EXAMPLES

Construction of DNA inserts, plasmids and recombinant viral vectors was carried out using the standard molecular biology techniques described by J. Sambrook et al. (Molecular Cloning: A Laboratory Manual, 4th edition, Cold Spring Harbor Laboratory, Cold Spring Harbor, N.Y., 2014).

Example 1 Culture, Isolation and Genotyping of Canine Influenza H3N2 Strains

Virus Isolation

Nasal swabs were obtained from pet dogs that exhibited symptoms of acute respiratory disease at veterinary clinics in Chicago, Ill. Swabs were transferred to vials containing transport Minimal essential medium (MEM) supplemented with 2% fetal bovine serum (HyClone) and 1× Antibiotic-Antimycotic (Gibco). Vials were placed at 4° C. and shipped cold by overnight courier within 4 days.

Infectious virus was isolated from clinical samples as follows. Samples were vortexed, and swabs were pressed against the vial walls to remove absorbed medium. The medium in each vial was filtered through a 0.4 µM filter, and 100 µL of filtered medium was inoculated into Madin-Darby Canine Kidney (MDCK) cells (ATCC) or 10 day old specific pathogen free (SPF) embryonated chicken eggs (Merial, Inc., Gainesville). Cell cultures were incubated at 37° C., and cell supernatants were harvested when a majority of cells exhibited virus-induced cytopathic effect (CPE). Inoculated eggs were incubated at 37° C. for 72 hours and subsequently chilled at 4° C. for at least 6 hours. To identify eggs that contained influenza virus, allantoic fluid from each inoculated egg was subjected to hemagglutination (HA) assay using 0.5% chicken red blood cells (RBCs) (Merial, Inc., Gainesville). Eggs containing >2 HA units per 50 µL of allantoic fluid were considered HA-positive, and the full volume of allantoic fluid in such eggs was removed, aliquoted, and frozen at −70° C. Five of twenty-four samples inoculated into eggs showed positive HA titers with values ranging from 32-256 HA units/50 µL. Two of the five samples (virus isolates ID #'s 4 and 8) were chosen for further vaccine development purposes and deposited at ATCC on Jun. 25, 2015 under accession number PTA-122265 (virus ID #4) and PTA-122266 (virus ID #8).

Viral RNA detection and virus subtyping

A real-time RT-PCR assay was developed to test for the presence and subtype of influenza virus in egg allantoic fluid. Primers pairs that specifically anneal to the N2 or N8 neuraminidase (NA) segment genomic RNA encoded by H3N2 and H3N8 subtype canine influenza viruses (CIV) were designed based on sequence alignments of NA gene sequences from CIVs available in GenBank. Forward primer SEQ ID NO:13 and reverse primer SEQ ID NO:14 were specific for the N2 NA gene of H3N2 CIV. Forward primer SEQ ID NO:15 and reverse primer SEQ ID NO:16 were specific for the N8 NA gene of H3N8 CIV.

RNA extracted from 140 µL of egg allantoic fluid (QIAamp Viral RNA Mini Kit; Qiagen) was tested for the presence of N2 and N8 genomic RNA using a QuantiTect SYBR Green RT-PCR Kit (Qiagen). Assay results (see FIG. 2 and Table 2) showed that the N2-specific primers produced amplification products with cycle threshold ($C_t$) values of 9.1-35, while the N8 specific primer pairs produced products with $C_t$ values >39 (the limit of detection). Conversely, RNA from eggs inoculated with a H3N8 subtype CIV (A/canine/Wyoming/86033/2007) yielded a product with a $C_t$ value of 15.4 when tested with N8-specific primers, but N2-specific primers did not yield detectable products. Thus, the virus isolated from the nasal swabs contained N2 but not N8 NA genomic RNA, suggesting that the isolated virus was H3N2 CIV.

TABLE 2

RT-PCR genotyping of CIVs

| RNA source | Virus subtype | Primer target | $C_t$ |
|---|---|---|---|
| None | N/A | N2 NA | ND |
| None | N/A | N8 NA | ND |
| A/Ca/WY/86033/07 | H3N8 | N2 NA | ND |
| A/Ca/WY/86033/07 | H3N8 | N8 NA | 15.4 |
| #4 | H3N2 | N2 NA | 9.1 |
| #4 | H3N2 | N8 NA | 39.1 |
| #8 | H3N2 | N2 NA | 9.5 |
| #8 | H3N2 | N8 NA | ND |

*ND—not detected.

Figure 3:
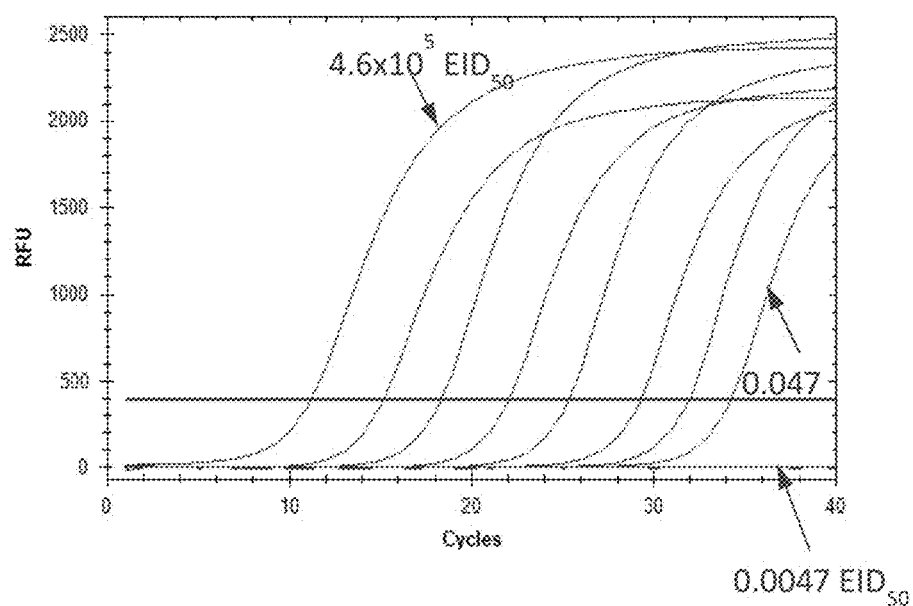
FIG. 3 depicts the sensitivity of the subtyping assay.
Figure 4:
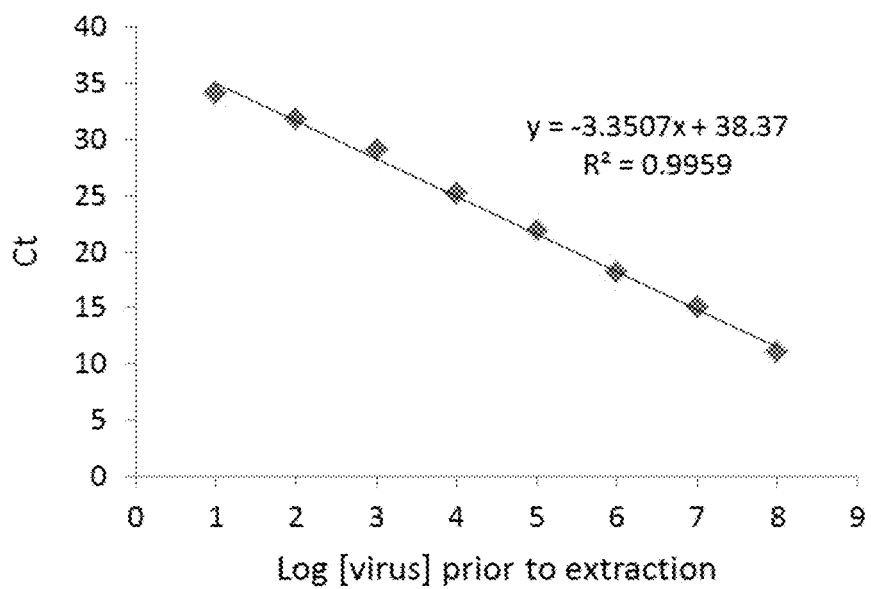
FIG. 4 depicts the efficiency of the subtyping assay.

FIGS. 3 and 4 show the sensitivity and efficiency of the subtyping assay. The assay is highly sensitive for H3N2 CIV as it is capable of detecting <0.01 EID50 units of virus (i.e. it can detect less than one infectious unit of virus). The assay is also highly efficient. FIG. 4 shows that the assay is 98.81% efficient on a scale from 1-100%. The amplification factor of the assay is 1.99, close to the perfect score of 2.0 (amplification factors are calculated in such a way that a value of 2.0 is considered perfect).

Example 2 Virus Propagation and Genomic RNA

Virus propagation in eggs

The 50% egg infectious dose ($EID_{50}$) assay was used to determine the titer of infectious virus present in the virus isolates. Virus samples were diluted in 10-fold increments from $10^{-1}$ to $10^{-9}$, and five eggs per dilution were inoculated with 100 µL per egg of the $10^{-4}$ to $10^{-9}$ dilutions. Eggs were sealed and incubated for 72 hours at 37° C. Eggs were then chilled at 4° C. for at least 6 hours, and allantoic fluid from each egg was tested for the presence of virus by HA assay. The HA titers ranged from 64-256 per 50 µL of allantoic fluid for viruses #4 and #8, and the $EID_{50}$/mL titer was 8.3 (#4) and 8.1 (#8) as calculated using the Spearman-Karber formula.

Large-scale virus stocks were prepared by inoculating each of sixty eggs with 100 µL of a $10^{-5}$ virus dilution. Eggs were incubated at 37° C. for 72 hours and chilled as before. Allantoic fluid was collected from each egg and pooled. Virus HA and $EID_{50}$ titers in the pooled fluids were 16 and 7.5 (#4) or 8 and 7.3 (#8). Virus stocks were aliquoted and stored in liquid nitrogen.

Virus Propagation in Madin-Darby Canine Kidney (MDCK) Cells

MDCK cells (ATCC) approved for vaccine derivation purposes by the USDA were seeded such that cell monolayers were ~90% confluent at the time of infection. Prior to infection, cells were washed twice with MEM lacking serum and inoculated with virus using a multiplicity of infection (M.O.I.) of 0.001 in a low inoculum volume. Samples were incubated at 37° C. for 1 hour with intermittent rocking, and media containing 1 ug/mL of TPCK-treated trypsin (Sigma-Aldrich) was added. Cultures were incubated at 37° C. and monitored for the appearance of virus-induced cytopathic effect (CPE). Under these conditions, the virus caused visible cell rounding and dissociation of cells from the substrate after 24-hours. Cell supernatants were harvested when approximately 90% of the cells had dissociated from the substrate. Supernatants were clarified by centrifugation at 1,000×g, and virus titers in the clarified supernatants were measured by HA and 50% tissue culture infectious dose (TCID$_{50}$) assays. After a single passage in MDCK cells, virus #4 achieved titers of 64 HA units/50 µL and 7.8 TCID$_{50}$ units/mL, and virus #8 replicated to titers of 64-128 HA units/50 µL and 8.6 TCID$_{50}$ units/mL. These cell stocks were subsequently used to produce pre-master seed stock material (virus #4, 64-128 HA units/50 µL and 8.4 TCID$_{50}$ units/mL) and purified antigen for raising virus-specific antisera in rabbits (virus #8, 128 HA units/50 µL and 8.7 TCID$_{50}$ units/mL).

Viral genomic RNA sequencing

Genomic RNA was extracted from virus propagated in eggs and MDCK cells. The full-length HA and NA genes were reverse transcribed and amplified by PCR using a One-Step RT-PCR Kit (Qiagen) and universal primers that anneal to the termini of each gene segment (Hoffman et al., 2001 Arch Virol Universal primer set for the full-length amplification of all influenza A viruses). The resulting RT-PCR products were separated by electrophoresis in a 0.8% agarose gel and purified using a QIAquick Gel Extraction Kit (Qiagen). Purified cDNAs were sequenced by conventional Sanger sequencing methods using HA and NA gene specific primers as shown in Table 3 below. Contiguous sequence assemblies with 2-fold or greater coverage were generated by aligning overlapping individual sequences using Sequencher 5.1 software (Gene Codes Corporation). Consensus sequences for each gene were generated from the assemblies in Sequencher 5.1 and designated SEQ ID NOs: 1, 3, 5, 7, 9 and 11 as shown in FIGS. 1 and 5. The corresponding HA and NA protein sequences are designated SEQ ID NOs:2, 4, 6, 8, 10 and 12 as shown in FIGS. 1 and 5.

TABLE 3 primers for sequencing HA and NA genes

| SEQ ID NO: | | |
|---|---|---|
| HA sequencing primers | | |
| 17 | Ca.H3N2.HA.390R | GAACTCCAATGTGCCTGATG |
| 18 | Ca.H3N2.HA.259F | CTGCACACTAATAGATGCCCTA |
| 19 | Ca.H3N2.HA.743F | CCAATCTGGCAGAATAAGCG |
| 20 | Ca.H3N2.HA.1276F | GAAGGGAGGATTCAAGACCTT |
| 21 | Ca.H3N2.HA.1569F | GGTTCCAGATCAAAGGTGTT |
| 22 | Ca.H3N2.HA.871R | CATTCGGAAATGCAGGTGTCA |
| 23 | Ca.H3N2.HA.1408R | TCAGCATTTTCCCTCAATTGC |
| NA gene sequencing primers | | |
| 24 | Ca.H3N2.NA.429F | GGG ACC ACG CTG AAC AAT AA |
| 25 | Ca.H3N2.NA.484R | TGA AAC GGA ACA CCC AAC TC |
| 26 | Ca.H3N2.NA.975F | TCA GGA CTT GTT GGC GAT AC |
| 27 | Ca.H3N2.NA.1023R | TCC TGG ATT CCC TCT CTC ATT A |
| 28 | Ca.H3N2.1229F | ACT GGT CTG GTT ATT CTG GTA TTT |
| 29 | Ca.H3N2.1279R | TCT TGT GGC CCT CCT CTT AT |

Analysis of the Sequences

The three HA protein sequences obtained from the CIV H3N2 strains isolated in the US share 99.6% sequence identity (FIG. 5). These HA proteins vary in the amino acid composition at positions 62, 219 and 249 of the immature (full-length) HA0 protein.

The three NA protein sequences obtained from the CIV H3N2 strains isolated in the US are identical, though the polynucleotides encoding the NA proteins differ slightly with 99.9% sequence identity (FIG. 5). The database search didn't detect any CIV H3N2 NA proteins having greater than 98% sequence identity to the NA protein sequences generated from the CIV H3N2 strains isolated in the US.

Example 3 Production of Virus-Specific Antibodies

Virus purification

MDCK cells in 225 $cm^2$ flasks were washed twice with 20 mL MEM per flask and inoculated with cell passage 1 of virus #8 at an MOI of 0.001 in a low inoculum volume. Cultures were incubated at 37° C. for 1 hour with intermittent rocking. Medium containing 1 ug/mL of TPCK-treated trypsin was added to each flask, and the flasks were incubated at 37° C. for 48 hours. Cell supernatants were harvested, and 540 mL of virus culture was clarified by centrifugation at 5,000×g for 10 min. using a Beckman JA-10 rotor. To pellet the virus, the clarified supernatant was centrifuged at 90,000×g for 2 hours at 4° C. using a SW32 Ti rotor. The pellet supernatant was aspirated, and 0.5 mL PBS was added to each virus pellet. Following overnight incubation on ice, the pellets were resuspended by gentle pipetting and pooled. The resuspended pellet material was loaded onto a sucrose step gradient containing equal volumes of 20%, 30%, 40%, and 55% w/v sucrose in PBS, and the gradient was centrifuged overnight at 100,000×g in a SW32Ti rotor at 4° C. The virus band was removed from the gradient and diluted in 5 volumes of PBS. Virus in the suspension was pelleted by centrifugation at 100,000×g in a SW32Ti rotor for 2 hours at 4° C. The pellet supernatant was aspirated, and the virus pellet was incubated in 1 mL of PBS at 4° C. for 48 hours. The pellet was then resuspended by gentle pipetting and titered. HA assays showed that approximately 80% of the HA units present in the clarified cell supernatant were recovered as purified material following the procedure described above.

Virus Inactivation

Five hundred thousand HA units of virus was diluted to a final volume of 20 mL in PBS. A chemical reaction using formaldehyde was done to inactivate the viruses. Formaldehyde (2% v/v in PBS, Thermo Scientific) was added to a final concentration of 0.02%, and the solution was incubated at 22° C. for 13 hours while rotating at 90 rpm. Residual formaldehyde was neutralized by addition of sodium bisulfite at a 1:1 molar ratio of sulfite ion to formaldehyde. Virus inactivation was confirmed by sequential passage of the undiluted virus suspension on MDCK cells. HA assays performed on the virus suspension before and after inactivation showed that the inactivation process did not reduce the quantity of HA units when compared to that of the starting material.

Other inactivation methods involving chemical reactions, such as BPL (betapropiolactone) and BEI (binary ethylenimine) are used to inactivate the viruses.

These chemical inactivation methods produce enumerable structural changes, including for example, formation of new chemical bonds via chemical crosslinking, irreversible chemical alteration of the nucleic acid and protein coat (Uittenbogaard, 2011, Journal of Biological Chemistry, 286 (42): pp36198-36214; Gard, Bull. Wld Hlth Org., 1957, 17, 979-989).

Production of antibodies

Purified, inactivated H3N2 CIV #8 was mixed at a 1:1 ratio with TiterMax Gold adjuvant (Sigma-Aldrich). Ten female specific pathogen free New Zealand White rabbits 10-16 weeks of age (Harlan) were injected subcutaneously in the hind quarter with 3 or 4 doses of 1,500 HA units of virus per dose. One week after the last vaccine dose, animals were anesthetized, and blood was collected. Serum samples were tested for serum neutralizing antibody titers against H3N2 CIV.

Example 4 Viral Antigenic Analysis

Viral antigenic analysis

Antibodies that bind to the HA protein on the surface of influenza virus particles can inhibit particle-induced red blood cell (RBC) agglutination in the context of an HA assay if the antibodies are present in sufficient quantities. Thus, the hemagglutination inhibition (HAI) assay is routinely used to (i) measure the quantity or dilution of an antibody required to inhibit RBC agglutination by a given virus strain (i.e. HAI titer), and (ii) to evaluate the antigenic relatedness of HA proteins present in virus particles from two or more different virus strains. Tests of antigenic relatedness are performed with antisera raised against one virus strain (i.e. the homologous strain) and test the capacity of that antisera to inhibit RBC agglutination by heterologous virus strains. A heterologous virus is typically considered antigenically distinct from the homologous virus if the HAI titer for the heterologous virus is >8-fold less than the HAI titer for the homologous virus.

An HAI assay employing serum from dogs vaccinated with a canarypox vector expressing the HA protein from A/equine/Ohio/1/2003 H3N8 virus was used to test the antigenic relatedness of H3N8 and H3N2 CIV. This serum was previously determined to have an HAI titer of 512 when tested against A/canine/Colorado/8880/2006, a H3N8 canine influenza virus. The H3N2 CIV isolate #4 (egg passage 2) and A/canine/Colorado/8880/2006 were diluted to 8 HA units/25 μL in PBS and incubated with 2-fold dilutions of serum (25 μL per dilution) for 1 hour at 22° C. An equal volume (50 μL) of 0.5% chicken RBCs was added to each sample, and the solutions were incubated for an additional hour at 22° C. Antibodies in the serum failed to inhibit RBC agglutination by H3N2 CIV at all dilutions tested (1:8-1:2048, HAI titer <8). In contrast, the serum inhibited RBC agglutination by A/canine/Colorado/8880/2006 at a maximal dilution of 1:512 (HAI titer 512). Thus, antibodies in this serum that recognize the HA protein of a H3N8 CIV do not bind to the HA protein of H3N2 CIV with high affinity, suggesting that the viruses are antigenically distinct.

Example 5 Production of Vaccine Active Ingredient and Preparation of Vaccines

To produce CIV H3N2 active ingredient (AI) for the preparation of inactivated CIV H3N2 vaccine, MDCK cells are used to amplify the CIV H3N2 virus in roller bottles for multiple passages according to standard virus production procedures.

The vaccine is prepared by mixing the CIV H3N2 active ingredient with an adjuvant. The adjuvant is aluminum hydroxide (or aluminum phosphate) or LR4 emulsion (U.S. Pat. No. 7,691,368) which contains 12.5% of "incomplete LR emulsion" and 87.5% of aqueous phase (containing the active ingredient).

Example 6 Evaluation of H3N2 Monovalent Vaccine Safety and Immunogenicity in Animals Vaccines were formulated as monovalent, aqueous solutions containing a 1x (1000 HAU) or 2x (1920 HAU) dose of whole, inactivated H3N2 CIV (PTA-122265 (virus ID #4)) and aluminum hydroxide (adjuvant). The placebo vaccine lacked antigen but contained adjuvant at the same concentration as the test vaccines.

Injection site reactions and clinical signs

Thirty CIV seronegative six-week old, commercial source beagles were randomized to three vaccination groups, containing 10 dogs each. Dogs in Groups 1 and 2 received 2x and 1x doses of the H3N2 CIV vaccine, respectively (Table 4). Dogs in Group 3 received a placebo vaccine. Each dog was vaccinated twice, 21 days apart, with 1 mL of vaccine, subcutaneously over the scapula. The dogs were monitored for injection site reactions and temperature elevations for three days after each vaccination and on days 14 and 27 (day prior to challenge). Blood samples were collected on days 0 (prior to vaccination), 7, 14, 21 (prior to vaccination), 27, and 35.

TABLE 4

Study Groups

| Group | Vaccine | Vaccination Route | Vaccination Frequency | No. of dogs | Challenge |
|---|---|---|---|---|---|
| 1 | 2X CIV | Subcutaneous | Twice, 21 days apart | 10 | H3N2 CIV |
| 2 | 1X CIV | Subcutaneous | Twice, 21 days apart | 10 | H3N2 CIV |

TABLE 4-continued

Study Groups

| Group | Vaccine | Vaccination Route | Vaccination Frequency | No. of dogs | Challenge |
|---|---|---|---|---|---|
| 3 | Placebo | Subcutaneous | Twice, 21 days apart | 10 | H3N2 CIV |

Seven days after the second vaccination, the dogs were challenged with virulent H3N2 CIV (PTA-122266 (virus ID #8)) via aerosolization in a closed chamber using a commercial nebulizer. During challenge, dogs were randomized to challenge chambers using treatment group and litter as blocking factors such that each treatment group, litter, and sex (if possible) was represented in each challenge chamber run. After challenge, dogs were randomized to post-challenge (PC) pens such that each pen contained dogs from all three treatment groups and each chamber run from the challenge phase.

The dogs were observed for cough, fever, mucopurulent nasal discharge, and other clinical signs for seven days. Nasal swabs for virus isolation were collected on days 3, 4, and 5 PC. A dog was classified as having disease due to CIV if it developed cough in addition to either fever or mucopurulent nasal discharge. A dog was considered febrile when the rectal temperature was ≥39.7° C. and 0.5° C. above baseline (day 0 rectal temperature). The challenge was considered valid when at least 60% of the placebo vaccinated dogs developed disease due to CIV.

Following each vaccination of dogs with the H3N2 CIV vaccine at 1× and 2× doses, no systemic or injection site adverse reactions were observed. Prior to challenge, no dogs in any group showed clinical signs of disease. After challenge, the first clinical signs of disease (cough, mucopurulent nasal discharge, and fever) were observed two days post-challenge (DPC), similar to dogs with natural and experimental CIV infection (Table 5).

TABLE 5

Number of dogs expressing clinical signs of CIV disease post-challenge

| Vaccine Group | Cough | Fever | Mucopurulent Nasal Discharge |
|---|---|---|---|
| 2X CIV (n = 10) | 0 | 1 | 0 |
| 1X CIV (n = 10) | 0 | 0 | 0 |
| Placebo (n = 10) | 9 | 5 | 10 |

Cough and mucopurulent nasal discharge were the most predominant clinical signs of disease, with most dogs in the placebo group coughing for 2 days and showing mucopurulent discharge for 4 days (Tables 6 and 7). Ninety percent (90%) of the dogs in the placebo group were observed with cough, and 100% of the placebo group developed mucopurulent nasal discharge. No animals in the 2×CIV or 1×CIV vaccine groups developed cough or mucopurulent discharge. The days with highest frequency were 3 DPC for cough (8 dogs) and 4 DPC for mucopurulent nasal discharge (10 dogs). Two days post-challenge was the day with the highest frequency of fever with 6 febrile dogs—five in the placebo group and one in the 2×CIV vaccine group. Most dogs had one instance of fever, while one dog in the placebo group had two days of fever (Table 8). Rectal temperatures for dogs with fever ranged from 39.7° C. to 40.4° C.

TABLE 6

Total days with cough

| Vaccine Group | Number of days of cough | | | |
|---|---|---|---|---|
| | 2 | 3 | 4 | 5 |
| 2X CIV (n* = 0) | — | — | — | — |
| 1X CIV (n = 0) | — | — | — | — |
| Placebo (n = 9) | 6 | 1 | 1 | 1 | n*: number of dogs (out of 10 dogs) with symptom.

TABLE 7

Total days with mucopurulent nasal discharge

| Vaccine Group | Number of days of mucopurulent nasal discharge | | | | |
|---|---|---|---|---|---|
| | 2 | 3 | 4 | 5 | 6 |
| 2X CIV (n* = 0) | — | — | — | — | — |
| 1X CIV (n = 0) | — | — | — | — | — |
| Placebo (n = 10) | 2 | 2 | 3 | 1 | 2 | n*: number of dogs (out of 10 dogs) with symptoms.

TABLE 8

Total days with fever

| Vaccine Group | Number of days of fever | |
|---|---|---|
| | 1 | 2 |
| 2X CIV (n* = 1) | 1 | — |
| 1X CIV (n = 0) | — | — |
| Placebo (n = 5) | 4 | 1 | n*: number of dogs (out of 10 dogs) with symptoms.

Ninety percent (90%) of the dogs in the placebo group met the case definition for clinical disease, thereby validating the challenge. The incidence of disease in dogs administered the H3N2 CIV vaccines was significantly reduced compared to the placebo vaccinated dogs (p=0.0001) (Table 9). Clinical disease was prevented in 100% of the CIV vaccinates, underscoring the effectiveness of the vaccines at preventing clinical disease.

TABLE 9

2X dose and 1X dose H3N2 Vaccine Group Prevented Fractions for CIV disease

| Vaccine Group | Number of dogs with disease | P-value (Fisher's Exact Test) | Prevented Fraction (95% CI)* |
|---|---|---|---|
| 2X CIV (n = 10) | 0 | 0.0001 | 1.00 (0.67, 1.00) |
| Placebo (n = 10) | 9 | | |
| 1X CIV (n = 10) | 0 | 0.0001 | 1.00 (0.67, 1.00) |

95% CI*: 95% confidence interval

Nasal shedding and serology

Fluids expressed from nasal swabs were inoculated into the allantoic cavity of 3 embryonic chicken eggs. Eggs were incubated for 3 days at 37° C. and tested for the presence of virus by HA assay. Specimens were considered positive for virus if at least 1 of 3 eggs contained detectable virus. Specimens were considered negative for virus if at least 2 eggs were viable at the time of testing, and no eggs contained detectable virus. Positive samples and samples for which 2 or 3 eggs were inviable at the time of testing were tested by $TCID_{50}$ assay.

Heat-inactivated serum samples were incubated with 2.5% v/v washed cRBCs for 30 min at room temperature, and cRBCs were pelleted by centrifugation. The pellet supernatant was used to perform the HAI assay using a final concentration of 0.25% v/v cRBCs. The HAI titer of each sample was recorded as the reciprocal of the highest serum dilution that completely inhibited cRBC agglutination by 8 HA units of H3N2 CIV. A titer of <4 was considered negative for CIV serum antibody.

Nasal swabs were collected to gauge the capability of the test vaccines to prevent viral shedding after challenge. In this study, the collection days also corresponded with the days of highest frequency of cough and mucopurulent nasal discharge. All dogs in the placebo group exhibited nasal shedding of CIV, and shedding was significantly reduced in the 2× and 1× dose groups on each collection day (Table 10). The reduction in shedding in the test vaccine groups equated to an 80% preventable fraction (Table 11). Similarly, the CIV vaccines administered in this study reduced shedding to undetectable levels in 100% of the CIV vaccinated dogs at 5 DPC.

TABLE 10

Incidence of nasal CIV shedding

| Vaccine Group | Number of dogs with positive nasal shedding | | |
| --- | --- | --- | --- |
| | 3 DPC (Day 31) | 4 DPC (Day 32) | 5 DPC (Day 33) |
| 2X CIV (n = 10) | $0^{\S a}$ | $2^{\S b}$ | $0^{\S a}$ |
| 1X CIV (n = 10) | $1^{\S c}$ | $1^{\S c}$ | $0^{\S a}$ |
| Placebo (n = 10) | 10 | 10 | 10 |

§significant difference between test vaccine and placebo
$^a$p < 0.0001
$^b$p = 0.0007
$^c$p = 0.0001

TABLE 11

2X dose and 1X dose H3N2 Vaccine Group Prevented Fractions for nasal shedding

| Vaccine Group | Number of dogs with positive nasal shedding | P-value (Fisher's Exact Test) | Prevented Fraction (95% CI) |
| --- | --- | --- | --- |
| 2X CIV (n = 10) | 2 | 0.0007 | 0.80 (0.46, 0.96) |
| Placebo (n = 10) | 10 | | |
| 1X CIV (n = 10) | 2 | 0.0007 | 0.80 (0.46, 0.96) |

This study is consistent with the observation that dogs not showing clinical signs of disease may still shed virus. The study found that 90% of the placebo dogs exhibited clinical disease, while 100% of the placebo dogs shed infectious virus. This result emphasizes the importance of limiting virus shedding as part of strategies to control virus transmission.

All animals were seronegative prior to the initiation of the study, and all dogs in the placebo group were seronegative prior to challenge (Table 12). On day 21, the proportion of dogs that seroconverted in the 2×CIV group was significantly higher than in the placebo group (p=0.0031), and on day 27, all dogs in the 2× and 1×CIV groups had seroconverted. Hence, seroconversion correlated with protection of the vaccinated dogs from clinical disease.

TABLE 12

Dogs seropositive (≥4) for CIV antibodies

| Vaccine Group | Number of dogs seroconverted | | | | | |
| --- | --- | --- | --- | --- | --- | --- |
| | Day 0* | Day 7 | Day 14 | Day 21* | Day 27# | Day 35† |
| 2X CIV (n = 10) | 0 | 0 | 1 | $7^{\S a}$ | $10^{\S b}$ | 10 |
| 1X CIV (n = 10) | 0 | 0 | 0 | 2 | $10^{\S b}$ | 10 |
| Placebo (n = 10) | 0 | 0 | 0 | 0 | 0 | 6 |

*Vaccination days-sample collected prior to vaccination
One day prior to challenge
†Seven days post-challenge
§significant difference between test vaccine and placebo
$^a$p = 0.0031
$^b$p < 0.0001

This study demonstrates that vaccination of dogs with an inactivated H3N2 CIV vaccine was well tolerated, produced seroconversion, and successfully protected 100% of vaccinates from clinical disease caused by challenge with virulent virus. Notably, the vaccines also reduced nasal shedding of infectious challenge virus, substantiating their use as safe and effective measures to alleviate signs of disease caused by CIV and potentially control virus transmission.

Example 6 Virus Propagation and Genomic RNA of H3N8 CIV Strains

Viruses from H3N8 CIV strains CT/85863/11, NY/120106/11 and WY/86033/07 were isolated in specific pathogen free embryonic chicken eggs and subsequently propagated in eggs or MDCK cells at 37° C. for 72 hours (eggs) or 36-48 hours (cells). Viruses were titrated by HA or $TCID_{50}$ assay as described for H3N2 CIV. The nucleotide sequences of the viral HA and NA genes from each virus strain were determined as for H3N2 CIV using the gene specific primers in FIG. 1.

The HA and NA polynucleotide and protein sequences for H3N8 CIV strains CT/85863/11, NY/120106/11 and WY/86033/07 are designated SEQ ID NOs:30-35 and 37-42 as shown in FIGS. 1 and 5.

Example 7 Preparation of Bivalent H3N2 and H3N8 CIV Vaccines

Viruses used in vaccine preparation were produced by infection of confluent monolayers of MDCK cells in roller bottle cultures at MOIs ranging from 0.0001 to 0.00001 in 200 mL of MEM supplemented with 1-2 ug/mL of porcine-origin trypsin (Sigma-Aldrich) per roller bottle. Cultures were incubated at 37° C. and 0.5 rpm and harvested 24 hours (H3N2 CIV) or 36-42 hours (H3N8 CIV) after inoculation of the cells with virus. Cell debris was removed from the virus suspension by centrifugation at 1,000×g or filtration through membranes containing 5 μM diameter pores. To inactivate infectious virus in the suspensions, formaldehyde was added to a final (v/v) concentration of 0.04%, and the reactions were incubated for 24 hours at 37° C. Inactivated virus preparations were stored at 4° C. until further use. In some cases, inactivated viral antigens were concentrated by ultrafiltration using polysulfone membranes containing 10 kDa pores. Vaccine antigens were confirmed to be fully inactivated and sterile prior to vaccine formulation.

Bivalent vaccines were prepared by mixing the desired quantity of each inactivated vaccine antigen with an adjuvant overnight at 4° C. The adjuvant is aluminum hydroxide (or aluminum phosphate) or LR4 emulsion (U.S. Pat. No. 7,691,368) which contains 12.5% of "incomplete LR emulsion" and 87.5% of aqueous phase (containing the active ingredient). Prepared vaccines were aliquoted into glass vials, sealed, and stored at 4° C. until use.

Example 8 Evaluation of H3N2/H3N8 Bivalent Vaccine Safety and Immunogenicity in Animals

Example 8.1 Efficacy of a Canine Influenza Virus H3N2/H3N8 Combination Vaccine Against H3N8 Challenge in Dogs The goal of the study is to evaluate the serological response, adverse events (interference) and efficacy of an injectable canine influenza virus H3N2/H3N8 combination vaccine in a vaccination-challenge model in dogs.

Thirty CIV seronegative six-week (+/−6 days) old, commercial source beagles were randomized to four vaccination groups as shown in Table 14 in one study. Dogs in Groups A and B received 1× and 2× doses of the H3N2/H3N8 combo CIV vaccine, respectively (Tables 13 and 14). Dogs in group C received a dose of H3N2 CIV vaccine. Dogs in Group D received a placebo vaccine. In another study, thirty CIV seronegative six-week (+/−6 days) old, commercial source beagles were randomized to two vaccination groups as shown in Table 15. Dogs in Group A received one dose of the H3N2/H3N8 combo CIV vaccine. Dogs in Group B received a placebo vaccine. Each dog was vaccinated twice, 21 days apart, with 1 mL of vaccine, subcutaneously. The dogs were monitored for injection site reactions and temperature elevations for three days after each vaccination and on days 7, 14, 21 (prior to vaccination), 22-24, 28 (prior to challenge) and 38 (end of study). Blood samples were collected on days 0 (prior to vaccination), 7, 14, 21 (prior to vaccination), 28 (prior to challenge), and 38 (end of study).

TABLE 13

Vaccine formulation

|  | H3N2/H3N8 Low dose(1X H3N2 and 1X H3N8) | H3N2/H3N8 High dose (1X H3N2 and 2X H3N8) | CIV H3N2 | Control |
| --- | --- | --- | --- | --- |
| Vaccine formulation | Inactivated H3N2* and H3N8** adjuvanted with Al(OH)$_3$ | Inactivated H3N2 and H3N8 adjuvanted with Al(OH)$_3$ | Inactivated H3N2 adjuvanted with Al(OH)$_3$ | PBS adjuvanted with Al(OH)$_3$ |
| dose | 1000 HAU of H3N2 and 750 HAU of H3N8 per dose; 1 ml = dose | 1000 HAU of H3N2 and 1500 HAU of H3N8 per dose; 1 ml = dose | 1000 HAU of H3N2 per dose; 1 ml = dose | 1 ml = 1 dose |

H3N2*: H3N2 CIV strain PTA-122265 (virus ID #4)
H3N8**: H3N8 CIV strain A/Ca/CT/85863/11

TABLE 14

Study design

| Group | Vaccine | Dose Volume | Route of Administration | Frequency of Administration | Number of animals |
| --- | --- | --- | --- | --- | --- |
| A | Low dose H3N2/H3N8 | 1 ml | SC | Twice, 21 days apart | 10 |
| B | High dose H3N2/H3N8 | 1 ml | SC | Twice, 21 days apart | 5 |
| C | CIV H3N2 | 1 ml | SC | Twice, 21 days apart | 10 |
| D | Control | 1 ml | SC | Twice, 21 days apart | 5 |

TABLE 15

Study design

| Group | Vaccine | Dose Volume | Route of Administration | Frequency of Administration | Number of animals |
| --- | --- | --- | --- | --- | --- |
| A | H3N2/H3N8* | 1 ml | SC | Twice, 21 days apart | 15 |
| B | Control** | 1 ml | SC | Twice, 21 days apart | 15 |

H3N2/H3N8*: Inactivated H3N2 and H3N8 adjuvanted with Al(OH)$_3$; 1000 HAU of H3N2 and 750 HAU of H3N8 per dose; 1 ml = 1 dose
Control**: PBS adjuvanted with Al(OH)$_3$; 1 ml = 1 dose Seven days after the second vaccination (day 28), the dogs were challenged with virulent H3N8 CIV strains WY/86033/07 and NY/120106/11 via aerosolization in a closed chamber using a commercial nebulizer. During challenge, dogs were randomized to challenge chambers using treatment group and litter as blocking factors such that each treatment group, litter, and sex (if possible) was represented in each challenge chamber run. After challenge, dogs were randomized to post-challenge (PC) pens such that each pen contained dogs from all three treatment groups and each chamber run from the challenge phase.

The dogs were observed for cough, fever, mucopurulent nasal discharge, and other clinical signs for ten days. Nasal swabs for virus isolation were collected three to six times after PC. A dog was classified as having disease due to CIV if it developed cough in addition to either fever or mucopurulent nasal discharge. A dog was considered febrile when the rectal temperature was ≥39.7° C. and 0.5° C. above baseline (day 0 rectal temperature). The challenge was considered valid when at least 60% of the placebo vaccinated dogs developed disease due to CIV.

The results show that vaccination of dogs with an inactivated H3N2/H3N8 combination vaccine is well tolerated, produced seroconversion, and successfully protected vaccinates from clinical disease caused by challenge with virulent H3N8 virus. The H3N2/H3N8 combination vaccine also demonstrates the lack of interference between the inactivated H3N2 vaccine and the inactivated H3N8 vaccine when formulated together in a combination vaccine.

Example 8.2 Efficacy of a Canine Influenza Virus H3N2/H3N8 Combination Vaccine Against H3N2 Challenge in Dogs The goal of the study is to evaluate the efficacy of an injectable canine influenza virus H3N2/H3N8 combination vaccine against lung lesions induced by CIV H3N2 in a vaccination-challenge model.

Thirty CIV seronegative six-week (+/−6 days) old, commercial source beagles were randomized to two vaccination groups as shown in Table 16. Dogs in Group A received one dose of the H3N2/H3N8 combo CIV vaccine. Dogs in Group B received a placebo vaccine. Each dog was vaccinated twice, 21 days apart, with 1 mL of vaccine, subcutaneously. The dogs were monitored for injection site reactions and temperature elevations for three days after each vaccination and on days 7, 14, 21 (prior to vaccination), 22-24, 28 (prior to challenge), 29-35, and 36 (end of study). Blood samples were collected on days 0 (prior to vaccination), 7, 14, 21 (prior to vaccination), 28 (prior to challenge), and 38 (end of study).

TABLE 16

| | | | Study design | | |
|---|---|---|---|---|---|
| Group | Vaccine | Dose Volume | Route of Administration | Frequency of Administration | Number of animals |
| A | H3N2/H3N8* Low dose | 1 ml | SC | Twice, 21 days apart | 15 |
| B | Control** | 1 ml | SC | Twice, 21 days apart | 15 |

H3N2/H3N8*: Inactivated H3N2 and H3N8 adjuvanted with Al(OH)$_3$; 1000 HAU of H3N2 and 750 HAU of H3N8 per dose; 1 ml = 1 dose
Control**: PBS adjuvanted with Al(OH)$_3$; 1 ml = 1 dose One week after the second vaccination the dogs are challenged with CIV H3N2 (PTA-122266 (virus ID #8) via aerosolization as described in Example 8.1. The dogs are observed for cough, fever, mucopurulent nasal discharge, and other clinical signs for seven days. Nasal swabs for virus isolation are collected three to six times after PC. Data are analyzed based on the criteria set out in Example 8.1.

The results show that vaccination of dogs with an inactivated H3N2/H3N8 combination vaccine is well tolerated, produced seroconversion, and successfully protected vaccinates from clinical disease caused by challenge with virulent H3N2 virus. The H3N2/H3N8 combination vaccine also demonstrates the lack of interference between the inactivated H3N2 vaccine and the inactivated H3N8 vaccine when formulated together in a combination vaccine.

Having thus described in detail embodiments of the present disclosure, it is to be understood that the disclosure defined by the above examples is not to be limited to particular details set forth in the above description as many apparent variations thereof are possible without departing from the spirit or scope of the present disclosure.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What we claim is:

1. A composition comprising an H3N2 influenza virus derived from canine isolates (H3N2 CIV), wherein the H3N2 CIV comprises,
   a) a polynucleotide encoding an HA protein having at least 99.6% sequence identity to the sequence as set forth in SEQ ID NO:2, 4, or 6; and/or
   b) a polynucleotide encoding an NA protein having at least 99% sequence identity to the sequence as set forth in SEQ ID NO:8, 10 or 12; and/or
   c) an HA polynucleotide having at least 99.2% sequence identity to the sequence as set forth in SEQ ID NO:1; or having at least 99.6% sequence identity to the sequence as set forth in SEQ ID NO:3; or having at least 99.9% sequence identity to the sequence as set forth in SEQ ID NO:5; and/or
   d) an NA polynucleotide having at least 99.9% sequence identity to the sequence set forth in SEQ ID NO:7 or 9.

2. The composition of claim 1, wherein the H3N2 CIV is deposited at ATCC under the deposit number of PTA-122265 or PTA-122266 or is a progeny or descendant of PTA-122265 or PTA-122266 wherein the progeny or descendant comprises a polynucleotide encoding an HA protein having at least 99.6% sequence identity to the sequence as set forth in SEQ ID NO:2, 4, or 6.

3. The composition of claim 1, wherein the H3N2 CIV is deposited at ATCC under the deposit number of PTA-122265 or PTA-122266, or is a progeny or descendant of PTA-122265 or PTA-122266, wherein the progeny or descendant comprises a polynucleotide encoding an NA protein having at least 99% sequence identity to the sequence as set forth in SEQ ID NO:8, 10, or 12.

4. The composition of claim 1, wherein the H3N2 CIV is inactivated.

5. The composition of claim 1, wherein the composition further comprises an inactivated H3N8 CIV.

6. The composition of claim 5, wherein the H3N8 CIV comprises a polynucleotide encoding an HA protein having at least 98% sequence identity SEQ ID NO:31, 35, or 39.

7. The composition of claim 5, wherein the H3N8 CIV comprises polynucleotide encoding an NA protein having at least 98% sequence identity SEQ ID NO:33, 37, or 41.

8. The composition of claim 1, wherein the composition or vaccine further comprises one or more pharmaceutically or veterinarily acceptable carrier, adjuvant, vehicle, or excipient.

9. A method of vaccinating an animal, or for inducing an immunogenic or protective response against influenza virus infection in canines (CIV), or for reducing CIV viral shedding in an infected animal, comprising at least one administration of the composition of claim 1.

10. The method of claim 9, wherein the animal is a canine or feline.

11. A diagnostic method of the infection of H3N2 influenza virus in dogs or cats (H3N2 CIV), wherein a sample of physiological fluid or a dog or cat tissue sampling and a diagnostic reagent specific to H3N2 CIV are put together, and the potential presence of H3N2 CIV antigen, antibody or nucleic acid is revealed within this sample or sampling, wherein the diagnostic reagent specific to H3N2 CIV comprises
   a) a polynucleotide encoding an HA protein having at least 99.6% sequence identity to the sequence as set forth in SEQ ID NO:2, 4, or 6; and/or
   b) a polynucleotide encoding an NA protein having at least 99% sequence identity to the sequence as set forth in SEQ ID NO:8, 10 or 12; and/or
   c) an HA polynucleotide having at least 99.2% sequence identity to the sequence as set forth in SEQ ID NO:1; or having at least 99.6% sequence identity to the sequence as set forth in SEQ ID NO:3; or having at least 99.9% sequence identity to the sequence as set forth in SEQ ID NO:5; and/or
   d) an NA polynucleotide having at least 99.9% sequence identity to the sequence set forth in SEQ ID NO:7 or 9.

12. The diagnostic method of claim 11, wherein the diagnostic reagent comprises a specific H3N2 CIV antigen selected from the group consisting of HA and NA, and wherein the antigen allows the detection of antibodies within the sample or sampling as being H3N2 CIV.

13. The diagnostic method of claim 11, wherein the method is Western blotting, immunofluoroescence, ELISA or immunochromatography.

* * * * *

SEQUENCE LISTING

```
<160> NUMBER OF SEQ ID NOS: 42

<210> SEQ ID NO 1
<211> LENGTH: 1698
<212> TYPE: DNA
<213> ORGANISM: artificial sequence
<220> FEATURE:
<223> OTHER INFORMATION: DNA encoding HA protein from #4 (in eggs)

<400> SEQUENCE: 1
atgaaaactg ttattgcttt aagctatatt ttctgcctgg cttttggtca gaatcttcta      60
ggaaatgaaa ataatgctgc aacactatgc ctgggacatc atgcagtgcc gaacgggaca     120
atggtgaaaa ctatcacaga cgatcaaatt gaggtgacca acgccaccga gctagtccaa     180
aactcctcaa cagggaaaat atgcaacaat ccccacaaga ttcttgatgg gagggactgc     240
acactaatag atgccctact aggggaccca cactgtgacg tcttccaaaa tgagacatgg     300
gacctttttg tggaacgaag caatgctttt agcaattgtt acccttatga tgtaccagac     360
tatgcatccc tccgatccat agttgcatca tcaggcacat tggagttcat cactgaaggt     420
ttcacttggg caggagtaac tcaaaatgga ggaagcggtg cttgtaaaag gggacctgct     480
```

```
aatagtttct tcagtagatt aaattggtta actaaatcag gaaatacata tccagtgttg      540
aatgtgacta tgccaaacaa caacaatttc gacaaattat acatttgggg agttcatcac      600
ccaagcacta atcaagaaca aaccagcctg tatattcagg cctcaggaag agtcacagtc      660
tctaccagga gaagccaaca gaccataatc ccaaacattg gatctagacc cttggtaagg      720
ggccaatctg gcagaataag cgtacattgg acaatagtca aacctggaga catactggta      780
ataaacagta atggaaacct aatcgctcct cgaggatact tcaaaatgca cattgggaaa      840
agctcaataa tgagatcaga tgcacctatt gacacctgca tttccgaatg tatcaccccg      900
aacgggagca tccccaatga aaagcccttc caaaatgtaa acaagatcac atacggagca      960
tgtcccaaat atgttaagca aaacaccttg aaactggcaa caggaatgcg gaatgtccct     1020
gagaggcaaa ccagaggcct gttcggcgca atagcaggct tcatagaaaa tggatgggaa     1080
gggatggtag acggttggta tggcttcagg caccaaaatt ccgaaggtac aggacaagca     1140
gcagacctta aaagcactca ggcagccatt gaccagatta tgggaaaatt gaacagagtg     1200
attgaaaaaa cgaatgagaa gttccatcaa attgaaaagg agttttccga agtagaaggg     1260
aggattcaag accttgagag atacgttgaa gacacaaaag tagatctttg gtcttacaat     1320
gccgagcttc ttgttgcctt agaaaaccag aacacaattg atttaactga ttcagaaatg     1380
aacaaattgt ttgaaaagac taggaggcaa ttgagggaaa atgctgaaga catgggcaat     1440
ggctgcttca gatatacca caagtgtgac aatgcttgca tagaatcgat tagaaacgga     1500
acttatgacc ataacatata tagagatgag gcagtgaaca atcggttcca gatcaaaggt     1560
gttgagctaa agtctggata caaagactgg atcttatgga tttcctttgc catatcatgc     1620
ttttgctttt gtgttgtctt gctgggtttc attatgtggg cctgccagag aggcaacatt     1680
aggtgcaaca tttgcatt                                                   1698

<210> SEQ ID NO 2
<211> LENGTH: 566
<212> TYPE: PRT
<213> ORGANISM: artificial sequence
<220> FEATURE:
<223> OTHER INFORMATION: HA protein from #4 (in eggs)

<400> SEQUENCE: 2

Met Lys Thr Val Ile Ala Leu Ser Tyr Ile Phe Cys Leu Ala Phe Gly
1               5                   10                  15

Gln Asn Leu Leu Gly Asn Glu Asn Asn Ala Ala Thr Leu Cys Leu Gly
            20                  25                  30

His His Ala Val Pro As

-continued

```
Gly Val Thr Gln Asn Gly Ser Gly Ala Cys Lys Arg Gly Pro Ala
145                 150                 155                 160

Asn Ser Phe Phe Ser Arg Leu Asn Trp Leu Thr Lys Ser Gly Asn Thr
            165                 170                 175

Tyr Pro Val Leu Asn Val Thr Met Pro Asn Asn Asn Phe Asp Lys
            180                 185                 190

Leu Tyr Ile Trp Gly Val His His Pro Ser Thr Asn Gln Glu Gln Thr
        195                 200                 205

Ser Leu Tyr Ile Gln Ala Ser Gly Arg Val Thr Val Ser Thr Arg Arg
        210                 215                 220

Ser Gln Gln Thr Ile Ile Pro Asn Ile Gly Ser Arg Pro Leu Val Arg
225                 230                 235                 240

Gly Gln Ser Gly Arg Ile Ser Val His Trp Thr Ile Val Lys Pro Gly
                245                 250                 255

Asp Ile Leu Val Ile Asn Ser Asn Gly Asn Leu Ile Ala Pro Arg Gly
                260                 265                 270

Tyr Phe Lys Met His Ile Gly Lys Ser Ser Ile Met Arg Ser Asp Ala
            275                 280                 285

Pro Ile Asp Thr Cys Ile Ser Glu Cys Ile Thr Pro Asn Gly Ser Ile
290                 295                 300

Pro Asn Glu Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Arg Gln Thr Arg Gly Leu Phe Gly Ala Ile Ala
                340                 345                 350

Gly Phe Ile Glu Asn Gly Trp Glu Gly Met Val Asp Gly Trp Tyr Gly
            355                 360                 365

Phe Arg His Gln Asn Ser Glu Gly Thr Gly Gln Ala Ala Asp Leu Lys
        370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Arg Tyr Val Glu Asp Thr
                420                 425                 430

Lys Val Asp Leu Trp Ser Tyr Asn Ala Glu Leu Leu Val Ala Leu Glu
            435                 440                 445

Asn Gln Asn Thr Ile Asp Leu Thr Asp Ser Glu Met Asn Lys Leu Phe
        450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asn Ile Tyr Arg Asp Glu Ala Val
                500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
            530                 535                 540

Val Val Leu Leu Gly Phe Ile Met Trp Ala Cys Gln Arg Gly Asn Ile
545                 550                 555                 560

Arg Cys Asn Ile Cys Ile
```

<210> SEQ ID NO 3
<211> LENGTH: 1698
<212> TYPE: DNA
<213> ORGANISM: artificial sequence
<220> FEATURE:
<223> OTHER INFORMATION: DNA encoding HA protein from #4 (in MDCK cells)

<400> SEQUENCE: 3

```
atgaaaactg ttattgcttt aagctatatt ttctgcctgg cttttggtca gaatcttcta      60
ggaaatgaaa ataatgctgc aacactatgc ctgggacatc atgcagtgcc gaacgggaca     120
atggtgaaaa ctatcacaga cgatcaaatt gaggtgacca acgccaccga gctagtccaa     180
aactcctcaa cagggaaaat atgcaacaat ccccacaaga ttcttgatgg agggactgc      240
acactaatag atgccctact aggggaccca cactgtgacg tcttccaaaa tgagacatgg     300
gaccttttg tggaacgaag caatgctttt agcaattgtt acccttatga tgtaccagac     360
tatgcatccc tccgatccat agttgcatca tcaggcacat ggagttcat cactgaaggt      420
ttcacttggg caggagtaac tcaaaatgga ggaagcggtg cttgtaaaag gggacctgct     480
aatagtttct tcagtagatt aaattggtta actaaatcag gaaatacata tccagtgttg     540
aatgtgacta tgccaaacaa caacaatttc gacaaattat acatttgggg agttcatcac     600
ccaagcacta atcaagaaca aaccagcctg tatattcagg cctcaggaag agtcaaagtc     660
tctaccagga gaagccaaca gaccataatc ccaaacattg gatctagacc cttggtaagg     720
ggccaatctg gcagaataag cgtatattgg acaaatagtca aacctggaga catactggta     780
ataacagta atggaaacct aatcgctcct cgaggatact tcaaaatgca cattgggaaa      840
agctcaataa tgagatcaga tgcacctatt gacacctgca tttccgaatg tatcaccccg     900
aacgggagca tccccaatga aaagcccttc caaaatgtaa acaagatcac atacggagca     960
tgtcccaaat atgttaagca aaacaccttg aaactggcaa caggaatgcg aatgtccct    1020
gagaggcaaa ccagaggcct gttcggcgca atagcaggct tcatagaaaa tggatgggaa    1080
gggatggtag acggttggta tggcttcagg caccaaaatt ccgaaggtac aggacaagca    1140
gcagacctta aaagcactca ggcagccatt gaccagatta tgggaaatt gaacagagtg    1200
attgaaaaaa cgaatgagaa gttccatcaa attgaaaagg agttttccga agtagaaggg    1260
aggattcaag accttgagag atacgttgaa gacacaaaag tagatctttg gtcttacaat    1320
gccgagcttc ttgttgcctt agaaaaccag aacacaattg atttaactga ttcagaaatg    1380
aacaaattgt ttgaaaagac taggaggcaa ttgagggaaa atgctgaaga catgggcaat    1440
ggctgcttca agatatacca caagtgtgac aatgcttgca tagaatcgat tagaaacgga    1500
acttatgacc ataacatata tagagatgag gcagtgaaca tcggttcca gatcaaaggt    1560
gttgagctaa agtctggata caaagactgg atcttatgga tttcctttgc catatcatgc    1620
tttttgcttt gtgttgtctt gctgggtttc attatgtggg cctgccagag aggcaacatt    1680
aggtgcaaca tttgcatt                                                 1698
```

<210> SEQ ID NO 4
<211> LENGTH: 566
<212> TYPE: PRT
<213> ORGANISM: artificial sequence
<220> FEATURE:
<223> OTHER INFORMATION: HA protein from #4 (in MDCK cells)

<400> SEQUENCE: 4

```
Met Lys Thr Val Ile Ala Leu Ser Tyr Ile Phe Cys Leu Ala Phe Gly
1               5                   10                  15

Gln Asn Leu Leu Gly Asn Glu Asn Asn Ala Ala Thr Leu Cys Leu Gly
            20                  25                  30

His His Ala Val Pro Asn Gly Thr Met Val Lys Thr Ile Thr Asp Asp
                35                  40                  45

Gln Ile Glu Val Thr Asn Ala Thr Glu Leu Val Gln Asn Ser Ser Thr
50                      55                  60

Gly Lys Ile Cys Asn Asn Pro His Lys Ile Leu Asp Gly Arg Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Asn Ala Phe Ser Asn
                100                 105                 110

Cys Tyr Pro Tyr Asp Val Pro Asp Tyr Ala Ser Leu Arg Ser Ile Val
            115                 120                 125

Ala Ser Ser Gly Thr Leu Glu Phe Ile Thr Glu Gly Phe Thr Trp Ala
130                 135                 140

Gly Val Thr Gln Asn Gly Gly Ser Gly Ala Cys Lys Arg Gly Pro Ala
145                 150                 155                 160

Asn Ser Phe Phe Ser Arg Leu Asn Trp Leu Thr Lys Ser Gly Asn Thr
                165                 170                 175

Tyr Pro Val Leu Asn Val Thr Met Pro Asn Asn Asn Asn Phe Asp Lys
            180                 185                 190

Leu Tyr Ile Trp Gly Val His His Pro Ser Thr Asn Gln Glu Gln Thr
            195                 200                 205

Ser Leu Tyr Ile Gln Ala Ser Gly Arg Val Lys Val Ser Thr Arg Arg
210                 215                 220

Ser Gln Gln Thr Ile Ile Pro Asn Ile Gly Ser Arg Pro Leu Val Arg
225                 230                 235                 240

Gly Gln Ser Gly Arg Ile Ser Val Tyr Trp Thr Ile Val Lys Pro Gly
                245                 250                 255

Asp Ile Leu Val Ile Asn Ser Asn Gly Asn Leu Ile Ala Pro Arg Gly
                260                 265                 270

Tyr Phe Lys Met His Ile Gly Lys Ser Ser Ile Met Arg Ser Asp Ala
            275                 280                 285

Pro Ile Asp Thr Cys Ile Ser Glu Cys Ile Thr Pro Asn Gly Ser Ile
            290                 295                 300

Pro Asn Glu Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
            325                 330                 335

Arg Asn Val Pro Glu Arg Gln Thr Arg Gly Leu Phe Gly Ala Ile Ala
                340                 345                 350

Gly Phe Ile Glu Asn Gly Trp Glu Gly Met Val Asp Gly Trp Tyr Gly
            355                 360                 365

Phe Arg His Gln Asn Ser Glu Gly Thr Gly Gln Ala Ala Asp Leu Lys
            370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415
```

```
Glu Val Glu Gly Arg Ile Gln Asp Leu Glu Arg Tyr Val Glu Asp Thr
            420                 425                 430
Lys Val Asp Leu Trp Ser Tyr Asn Ala Glu Leu Leu Val Ala Leu Glu
        435                 440                 445
Asn Gln Asn Thr Ile Asp Leu Thr Asp Ser Glu Met Asn Lys Leu Phe
450                 455                 460
Glu Lys Thr Arg Arg Gln Leu Arg Glu Asn Ala Glu Asp Met Gly Asn
465                 470                 475                 480
Gly Cys Phe Lys Ile Tyr His Lys Cys Asp Asn Ala Cys Ile Glu Ser
                485                 490                 495
Ile Arg Asn Gly Thr Tyr Asp His Asn Ile Tyr Arg Asp Glu Ala Val
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
530                 535                 540
Val Val Leu Leu Gly Phe Ile Met Trp Ala Cys Gln Arg Gly Asn Ile
545                 550                 555                 560
Arg Cys Asn Ile Cys Ile
            565

<210> SEQ ID NO 5
<211> LENGTH: 1698
<212> TYPE: DNA
<213> ORGANISM: artificial sequence
<220> FEATURE:
<223> OTHER INFORMATION: DNA encoding HA protein from #8 (in eggs)

<400> SEQUENCE: 5
atgaaaactg ttattgcttt aagctatatt ttctgcctgg cttttggtca gaatcttcta      60
ggaaatgaaa ataatgctgc aacactatgc ctgggacatc atgcagtgcc gaacgggaca     120
atggtgaaaa ctatcacaga cgatcaaatt gaggtgacca acgccaccga gctagtccaa     180
aacccctcaa cagggaaaat atgcaacaat ccccacaaga ttcttgatgg gagggactgc     240
acactaatag atgccctact aggggaccca cactgtgacg tcttccaaaa tgagacatgg     300
gacctttttg tggaacgaag caatgctttt agcaattgtt acccttatga tgtaccagac     360
tatgcatccc tccgatccat agttgcatca tcaggcacat ggagttcat cactgaaggt     420 ttcacttggg caggagtaac tcaaaatgga ggaagcggtg cttgtaaaag gggacctgct     480
aatagtttct tcagtagatt aaattggtta actaaatcag gaaatacata tccagtgttg     540
aatgtgacta tgccaaacaa caacaatttc gacaaattat catttgggg agttcatcac     600 ccaagcacta tcaagaaaca accagcctg tatattcagg cctcaggaag agtcacagtc     660
tctaccagga agccaaca gaccataatc ccaaacattg gatctagacc cttggtaagg     720
ggccaatctg cagaataag cgtatattgg acaatagtca aacctggaga catactggta     780
ataaacagta atggaaacct aatcgctcct cgaggatact caaaatgca cattgggaaa     840 agctcaataa tgagatcaga tgcacctatt gacacctgca tttccgaatg tatcaccccg     900
aacgggagca tccccaatga aaagcccttc caaaatgtaa acaagatcac atacggagca     960
tgtcccaaat atgttaagca aaacaccttg aaactggcaa caggaatgcg gaatgtccct    1020
gagaggcaaa ccagaggcct gttcggcgca atagcaggct tcatagaaaa tggatgggaa    1080
gggatggtag acggttggta tggcttcagg caccaaaatt ccgaaggtac aggacaagca    1140
gcagacctta aaagcactca ggcagccatt gaccagatta tgggaaatt gaacagagtg    1200
```

```
attgaaaaaa cgaatgagaa gttccatcaa attgaaaagg agttttccga agtagaaggg    1260
aggattcaag accttgagag atacgttgaa gacacaaaag tagatctttg gtcttacaat    1320
gccgagcttc ttgttgcctt agaaaaccag aacacaattg atttaactga ttcagaaatg    1380
aacaaattgt ttgaaaagac taggaggcaa ttgagggaaa atgctgaaga catgggcaat    1440
ggctgcttca agatatacca caagtgtgac aatgcttgca tagaatcgat tagaaacgga    1500
acttatgacc ataacatata tagagatgag gcagtgaaca atcggttcca gatcaaaggt    1560
gttgagctaa agtctggata caaagactgg atcttgtgga tttcctttgc catatcatgc    1620
tttttgcttt gtgttgtctt gctgggtttc attatgtggg cctgccagag aggcaacatt    1680
aggtgcaaca tttgcatt                                                  1698
```

<210> SEQ ID NO 6
<211> LENGTH: 566
<212> TYPE: PRT
<213> ORGANISM: artificial sequence
<220> FEATURE:
<223> OTHER INFORMATION: NA protein from #8 (in eggs)

<400> SEQUENCE: 6

```
Met Lys Thr Val Ile Ala Leu Ser Tyr Ile Phe Cys Leu Ala Phe Gly
1               5                   10                  15

Gln Asn Leu Leu Gly Asn Glu Asn Asn Ala Ala Thr Leu Cys Leu Gly
            20                  25                  30

His His Ala Val Pro Asn Gly Thr Met Val Lys Thr Ile Thr Asp Asp
        35                  40                  45

Gln Ile Glu Val Thr Asn Ala Thr Glu Leu Val Gln Asn Pro Ser Thr
    50                  55                  60

Gly Lys Ile Cys Asn Asn Pro His Lys Ile Leu Asp Gly Arg Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Asn Ala Phe Ser Asn
            100                 105                 110

Cys Tyr Pro Tyr Asp Val Pro Asp Tyr Ala Ser Leu Arg Ser Ile Val
        115                 120                 125

Ala Ser Ser Gly Thr Leu Glu Phe Ile Thr Glu Gly Phe Thr Trp Ala
    130                 135                 140

Gly Val Thr Gln Asn Gly Gly Ser Gly Ala Cys Lys Arg Gly Pro Ala
145                 150                 155                 160

Asn Ser Phe Phe Ser Arg Leu Asn Trp Leu Thr Lys Ser Gly Asn Thr
                165                 170                 175

Tyr Pro Val Leu Asn Val Thr Met Pro Asn Asn Asn Phe Asp Lys
            180                 185                 190

Leu Tyr Ile Trp Gly Val His His Pro Ser Thr Asn Gln Glu Gln Thr
        195                 200                 205

Ser Leu Tyr Ile Gln Ala Ser Gly Arg Val Thr Val Ser Thr Arg Arg
    210                 215                 220

Ser Gln Gln Thr Ile Ile Pro Asn Ile Gly Ser Arg Pro Leu Val Arg
225                 230                 235                 240

Gly Gln Ser Gly Arg Ile Ser Val Tyr Trp Thr Ile Val Lys Pro Gly
                245                 250                 255

Asp Ile Leu Val Ile Asn Ser Asn Gly Asn Leu Ile Ala Pro Arg Gly
            260                 265                 270
```

```
Tyr Phe Lys Met His Ile Gly Lys Ser Ser Ile Met Arg Ser Asp Ala
            275                 280                 285
Pro Ile Asp Thr Cys Ile Ser Glu Cys Ile Thr Pro Asn Gly Ser Ile
        290                 295                 300
Pro Asn Glu Lys Pro Phe Gln Asn Val Asn Lys Ile Thr Tyr Gly Ala
305                 310                 315                 320
Cys Pro Lys Tyr Val Lys Gln Asn Thr Leu Lys Leu Ala Thr Gly Met
                325                 330                 335
Arg Asn Val Pro Glu Arg Gln Thr Arg Gly Leu Phe Gly Ala Ile Ala
            340                 345                 350
Gly Phe Ile Glu Asn Gly Trp Glu Gly Met Val Asp Gly Trp Tyr Gly
        355                 360                 365
Phe Arg His Gln Asn Ser Glu Gly Thr Gly Gln Ala Ala Asp Leu Lys
370                 375                 380
Ser Thr Gln Ala Ala Ile Asp Gln Ile Asn Gly Lys Leu Asn Arg Val
385                 390                 395                 400
Ile Glu Lys Thr Asn Glu Lys Phe His Gln Ile Glu Lys Glu Phe Ser
                405                 410                 415
Glu Val Glu Gly Arg Ile Gln Asp Leu Glu Arg Tyr Val Glu Asp Thr
            420                 425                 430
Lys Val Asp Leu Trp Ser Tyr Asn Ala Glu Leu Leu Val Ala Leu Glu
        435                 440                 445
Asn Gln Asn Thr Ile Asp Leu Thr Asp Ser Glu Met Asn Lys Leu Phe
450                 455                 460
Glu Lys Thr Arg Arg Gln Leu Arg Glu Asn Ala Glu Asp Met Gly Asn
465                 470                 475                 480
Gly Cys Phe Lys Ile Tyr His Lys Cys Asp Asn Ala Cys Ile Glu Ser
                485                 490                 495
Ile Arg Asn Gly Thr Tyr Asp His Asn Ile Tyr Arg Asp Glu Ala Val
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
530                 535                 540
Val Val Leu Leu Gly Phe Ile Met Trp Ala Cys Gln Arg Gly Asn Ile
545                 550                 555                 560
Arg Cys Asn Ile Cys Ile
                565

<210> SEQ ID NO 7
<211> LENGTH: 1407
<212> TYPE: DNA
<213> ORGANISM: artificial sequence
<220> FEATURE:
<223> OTHER INFORMATION: DNA encoding NA protein from #4 (in eggs)

<400> SEQUENCE: 7
atgaacccaa atcaaaagat aatagcaata gggtctgtct ctctaaccat tgcaacagta      60
tgtttcctct tacagattgc catcctagca acaactgtga cactgtactt caagcaaaat     120
gaatgcaaca tcccctcgaa cagtcaagta gtgccatgta aaccaatcat aatagaaagg     180
aacataacag aggtagtata tttgaataat actaccatag aaaagaaat tgctccgta      240 gtgctagaat acaggaactg gtcgaaaccg cagtgtcaaa ttacaggatt tgctcctttc     300
tccaaggaca actcaatccg actctccgct ggtgggaca tttgggtaac aagggaacct     360
```

```
tatgtgtcat gcgaccacag caaatgttat cagtttgcac ttgggcaggg gaccacgctg      420
aacaataaac actcaaacag cacaatacat gataggacct ctcatcgaac tcttttaatg      480
aatgagttgg gtgttccgtt tcatttggga accaaacaag tgtgcatagc atggtccagt      540
tcaagttgtc acgatgggaa agcatggtta catgtttgtg tcactggaga tgatagaaat      600
gcgactgcta gtttcgttta atggaatg cttgttgaca gtattggttc atggtctcga       660
aatatcctca gaactcaaga gtcagaatgt gtttgcatca atgggacttg tacagtagta      720
atgactgatg gaagtgcatc aggaagggct gatactagaa tactattcat cagagagggg      780
aaaattatcc atattagccc attgtcaggg agtgctcaac acatagagga atgttcctgt      840
tatccccgat atccaaatgt tagatgtgtt tgcagagaca attggaaggg ctccaatagg      900
cccgttatag atataaatat ggcagattat aacatcaatt ccagttatgt ctgttcagga      960
cttgttggcg atacaccaag gaatgatgat agctctagca gcagtaactg caaggatcct     1020
aataatgaga gagggaatcc aggagtgaag gggtgggcct ttgataatga taatgacgtt     1080
tggatgggga ggacaatcag caaagattta cgttcaggtt atgagacttt caaggtcatt     1140
ggtggctgga ccactgctaa ttccaagtca caggtcaata gacaagtcat agttgacaat     1200
aataactggt ctggttattc tggtattttc tccgttgaag gcaaaagctg tgttaatagg     1260 tgttttatg tggagttgat aagaggaggg ccacaagaga ctagagtatg gtggacttca     1320
aatagcattg tcgtattttg tggtacttct ggtacctatg aacaggctc atggcctgat      1380 ggggcgaata ttaacttcat gcctata                                         1407
```

<210> SEQ ID NO 8
<211> LENGTH: 469
<212> TYPE: PRT
<213> ORGANISM: artificial sequence
<220> FEATURE:
<223> OTHER INFORMATION: NA protein from #4 (in eggs)

<400> SEQUENCE: 8

```
Met Asn Pro Asn Gln Lys Ile Ile Ala Ile Gly Ser Val Ser Leu Thr
1               5                   10                  15

Ile Ala Thr Val Cys Phe Leu Leu Gln Ile Ala Ile Leu Ala Thr Thr
            20                  25                  30

Val Thr Leu Tyr Phe Lys Gln Asn Glu Cys Asn Ile Pro Ser Asn Ser
        35                  40                  45

Gln Val Val Pro Cys Lys Pro Ile Ile Ile Glu Arg Asn Ile Thr Glu
    50                  55                  60

Val Val Tyr Leu Asn Asn Thr Thr Ile Glu Lys Glu Ile Cys Ser Val
65                  70                  75                  80

Val Leu Glu Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp His Ser Lys
        115                 120                 125

Cys Tyr Gln Phe Ala Leu Gly Gln Gly Thr Thr Leu Asn Asn Lys His
    130                 135                 140

Ser Asn Ser Thr Ile His Asp Arg Thr Ser His Arg Thr Leu Leu Met
145                 150                 155                 160

Asn Glu Leu Gly Val Pro Phe His Leu Gly Thr Lys Gln Val Cys Ile
                165                 170                 175
```

Ala Trp Ser Ser Ser Cys His Asp Gly Lys Ala Trp Leu His Val
            180                 185                 190

Cys Val Thr Gly Asp Asp Arg Asn Ala Thr Ala Ser Phe Val Tyr Asn
            195                 200                 205

Gly Met Leu Val Asp Ser Ile Gly Ser Trp Ser Arg Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Arg Glu Gly Lys Ile Ile His Ile Ser Pro Leu Ser Gly Ser Ala
            260                 265                 270

Gln His Ile Glu Glu Cys Ser Cys Tyr Pro Arg Tyr Pro Asn Val Arg
            275                 280                 285

Cys Val Cys Arg Asp Asn Trp Lys Gly Ser Asn Arg Pro Val Ile Asp
            290                 295                 300

Ile Asn Met Ala Asp Tyr Asn Ile Asn Ser Ser Tyr Val Cys Ser Gly
305                 310                 315                 320

Leu Val Gly Asp Thr Pro Arg Asn Asp Asp Ser Ser Ser Ser Ser Asn
                325                 330                 335

Cys Lys Asp Pro Asn Asn Glu Arg Gly Asn Pro Gly Val Lys Gly Trp
            340                 345                 350

Ala Phe Asp Asn Asp Asn Asp Val Trp Met Gly Arg Thr Ile Ser Lys
            355                 360                 365

Asp Leu Arg Ser Gly Tyr Glu Thr Phe Lys Val Ile Gly Gly Trp Thr
    370                 375                 380

Thr Ala Asn Ser Lys Ser Gln Val Asn Arg Gln Val Ile Val Asp Asn
385                 390                 395                 400

Asn Asn Trp Ser Gly Tyr Ser Gly Ile Phe Ser Val Glu Gly Lys Ser
                405                 410                 415

Cys Val Asn Arg Cys Phe Tyr Val Glu Leu Ile Arg Gly Gly Pro Gln
            420                 425                 430

Glu Thr Arg Val Trp Trp Thr Ser Asn Ser Ile Val Val Phe Cys Gly
            435                 440                 445

Thr Ser Gly Thr Tyr Gly Thr Gly Ser Trp Pro Asp Gly Ala Asn Ile
    450                 455                 460

Asn Phe Met Pro Ile
465

<210> SEQ ID NO 9
<211> LENGTH: 1407
<212> TYPE: DNA
<213> ORGANISM: artificial sequence
<220> FEATURE:
<223> OTHER INFORMATION: DNA encoding NA protein from #4 (in MDCK cells)

<400> SEQUENCE: 9
atgaacccaa atcaaaagat aatagcaata gggtctgtct ctctaaccat tgcaacagta        60
tgtttcctct tacagattgc catcctagca acaactgtga cactgtactt caagcaaaat       120
gaatgcaaca tcccctcgaa cagtcaagta gtgccatgta accaatcat aatagaaagg        180 aacataacag aggtagtata tttgaataat actaccatag aaaagaaat tgctccgta         240 gtgctagaat acaggaactg gtcgaaaccg cagtgtcaaa ttacaggatt tgctcctttc       300
tccaaggaca actcaatccg actctccgct ggtgggggaca tttgggtaac aagggaacct     360

```
tatgtgtcat gcgaccacag caaatgttat cagtttgcac ttgggcaggg gaccacgctg      420
aacaataaac actcaaacag cacaatacat gataggacct ctcatcgaac tcttttaatg      480
aatgagttgg gtgttccgtt tcatttggga accaaacaag tgtgcatagc atggtccagt      540
tcaagttgtc acgatgggaa agcatggtta catgtttgtg tcactggaga tgatagaaat      600
gcgactgcta gtttcgttta atggaatgc cttgttgaca gtattggttc atggtctcga      660
aatatcctca gaactcaaga gtcagaatgt gtttgcatca atgggacttg tacagtagta      720
atgactgatg aagtgcatc aggaagggct gatactagaa tactattcat cagagagggg      780
aaaattatcc atattagccc attgtcaggg agtgctcaac acatagagga atgttcctgt      840
tatccccgat atccaaatgt tagatgtgtt tgcagagaca attggaaggg ctccaatagg      900
cccgttatag atataaatat ggcagattat aacatcaatt ccagttatgt ctgttcagga      960
cttgttggcg ataccaag gaatgatgat agctctagca gcagtaactg caaggatcct     1020
aataatgaga gagggaatcc aggagtgaag gggtgggcct ttgataatga taatgacgtt     1080
tggatgggga ggacaatcag caaagattta cgttcaggtt atgagacttt caaggtcatt     1140
ggtggctgga ccactgctaa ttccaagtca caggtcaata gacaagtcat agttgacaat     1200
aataactggt ctggttattc tggtattttc tccgttgaag gcaaaagctg tgttaatagg     1260
tgtttttatg tggagttgat aagaggaggg ccacaagaga ctagagtatg gtggacttca     1320
aatagcattg tcgtattttg tggtacttct ggtacctatg aacaggctc atggcctgat     1380 ggggcgaata ttaacttcat gcctata                                           1407
```

<210> SEQ ID NO 10
<211> LENGTH: 469
<212> TYPE: PRT
<213> ORGANISM: artificial sequence
<220> FEATURE:
<223> OTHER INFORMATION: NA protein from #4 (in MDCK cells)

<400> SEQUENCE: 10

```
Met Asn Pro Asn Gln Lys Ile Ile Ala Ile Gly Ser Val Ser Leu Thr
1               5                   10                  15

Ile Ala Thr Val Cys Phe Leu Leu Gln Ile Ala Ile Leu Ala Thr Thr
            20                  25                  30

Val Thr Leu Tyr Phe Lys Gln Asn Glu Cys Asn Ile Pro Ser Asn Ser
        35                  40                  45

Gln Val Val Pro Cys Lys Pro Ile Ile Ile Glu Arg Asn Ile Thr Glu
    50                  55                  60

Val Val Tyr Leu Asn Asn Thr Thr Ile Glu Lys Glu Ile Cys Ser Val
65                  70                  75                  80

Val Leu Glu Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp His Ser Lys
        115                 120                 125

Cys Tyr Gln Phe Ala Leu Gly Gln Gly Thr Thr Leu Asn Asn Lys His
    130                 135                 140

Ser Asn Ser Thr Ile His Asp Arg Thr Ser His Arg Thr Leu Leu Met
145                 150                 155                 160

Asn Glu Leu Gly Val Pro Phe His Leu Gly Thr Lys Gln Val Cys Ile
                165                 170                 175
```

-continued

```
Ala Trp Ser Ser Ser Ser Cys His Asp Gly Lys Ala Trp Leu His Val
            180                 185                 190
Cys Val Thr Gly Asp Asp Arg Asn Ala Thr Ala Ser Phe Val Tyr Asn
        195                 200                 205
Gly Met Leu Val Asp Ser Ile Gly Ser Trp Ser Arg Asn Ile Leu Arg
    210                 215                 220
Thr Gln Glu Ser Glu Cys Val Cys Ile Asn Gly Thr Cys Thr Val Val
225                 230                 235                 240
Met Thr Asp Gly Ser Ala Ser Gly Arg Ala Asp Thr Arg Ile Leu Phe
                245                 250                 255
Ile Arg Glu Gly Lys Ile Ile His Ile Ser Pro Leu Ser Gly Ser Ala
            260                 265                 270
Gln His Ile Glu Glu Cys Ser Cys Tyr Pro Arg Tyr Pro Asn Val Arg
        275                 280                 285
Cys Val Cys Arg Asp Asn Trp Lys Gly Ser Asn Arg Pro Val Ile Asp
    290                 295                 300
Ile Asn Met Ala Asp Tyr Asn Ile Asn Ser Ser Tyr Val Cys Ser Gly
305                 310                 315                 320
Leu Val Gly Asp Thr Pro Arg Asn Asp Asp Ser Ser Ser Ser Ser Asn
                325                 330                 335
Cys Lys Asp Pro Asn Asn Glu Arg Gly Asn Pro Gly Val Lys Gly Trp
            340                 345                 350
Ala Phe Asp Asn Asp Asn Asp Val Trp Met Gly Arg Thr Ile Ser Lys
        355                 360                 365
Asp Leu Arg Ser Gly Tyr Glu Thr Phe Lys Val Ile Gly Gly Trp Thr
    370                 375                 380
Thr Ala Asn Ser Lys Ser Gln Val Asn Arg Gln Val Ile Val Asp Asn
385                 390                 395                 400
Asn Asn Trp Ser Gly Tyr Ser Gly Ile Phe Ser Val Glu Gly Lys Ser
                405                 410                 415
Cys Val Asn Arg Cys Phe Tyr Val Glu Leu Ile Arg Gly Gly Pro Gln
            420                 425                 430
Glu Thr Arg Val Trp Trp Thr Ser Asn Ser Ile Val Val Phe Cys Gly
        435                 440                 445
Thr Ser Gly Thr Tyr Gly Thr Gly Ser Trp Pro Asp Gly Ala Asn Ile
    450                 455                 460
Asn Phe Met Pro Ile
465
```

<210> SEQ ID NO 11
<211> LENGTH: 1407
<212> TYPE: DNA
<213> ORGANISM: artificial sequence
<220> FEATURE:
<223> OTHER INFORMATION: DNA encoding NA protein from #8 (in eggs)

<400> SEQUENCE: 11

```
atgaacccaa atcaaaagat aatagcaata gggtctgtct ctctaaccat tgcaacagta      60
tgtttcctct tacagattgc catcctagca acaactgtga cactgtactt caagcaaaat     120
gaatgcaaca tcccctcgaa cagtcaagta gtgccatgta aaccaatcat aatagaaagg     180
aacataacag aggtagtata tttgaataat actaccatag aaaaagaaat ttgctccgta     240
gtgctagaat acaggaactg gtcgaaaccg cagtgtcaaa ttacaggatt tgctcctttc     300
tccaaggaca actcaatccg actctccgct ggtggggaca tttgggtaac aagggaacct     360
```

```
tatgtgtcat gcgaccacag caaatgttat cagtttgcac ttgggcaggg gaccacgctg      420
aacaataaac actcaaacag cacaatacat gataggacct ctcatcgaac tcttttaatg      480
aatgagttgg gtgttccgtt tcatttggga accaaacaag tgtgcatagc atggtccagt      540
tcaagttgtc acgatgggaa agcatggtta catgtttgtg tcactggaga tgatagaaat      600
gcgactgcta gtttcgttta atggaatg cttgttgaca gtattggttc atggtctcga       660
aatatcctca gaactcaaga gtcagaatgt gtttgcatca atgggacttg tacagtagta     720
atgactgatg gaagtgcatc aggaagggct gatactagaa tactattcat cagagagggg     780
aaaattatcc atattagccc attgtcaggg agtgctcaac acatagagga atgttcctgt     840
tatccccgat atccaaatgt tagatgtgtt tgcagagaca attggaaggg ctccaatagg     900
cccgttatag atataaatat ggcagattat aacatcaatt ccagttatgt ctgttcagga     960
cttgttggcg atacaccaag gaatgatgat agctctagca gcagtaactg caaggatcct    1020
aataatgaga gagggaatcc aggagtgaag gggtgggcct ttgataatga taatgacgtt    1080
tggatgggga ggacaatcag caaagattta cgttcaggtt atgagacttt caaggtcatt    1140
ggtggctgga ccactgctaa ttccaagtca caggtcaata gacaagtcat agttgacaat    1200
aataactggt ctggttattc tggtattttc tccgttgaag gcaaaagctg tgttaatagg    1260 tgttttatg tggagttgat aaggggaggg ccacaagaga ctagagtatg gtggacttca    1320
aatagcattg tcgtattttg tggtacttct ggtacctatg aacaggctc atggcctgat    1380 ggagcgaata ttaacttcat gcctata                                        1407
```

<210> SEQ ID NO 12
<211> LENGTH: 469
<212> TYPE: PRT
<213> ORGANISM: artificial sequence
<220> FEATURE:
<223> OTHER INFORMATION: NA protein from #8 (in eggs)

<400> SEQUENCE: 12

```
Met Asn Pro Asn Gln Lys Ile Ile Ala Ile Gly Ser Val Ser Leu Thr
1               5                   10                  15

Ile Ala Thr Val Cys Phe Leu Leu Gln Ile Ala Ile Leu Ala Thr Thr
            20                  25                  30

Val Thr Leu Tyr Phe Lys Gln Asn Glu Cys Asn Ile Pro Ser Asn Ser
        35                  40                  45

Gln Val Val Pro Cys Lys Pro Ile Ile Ile Glu Arg Asn Ile Thr Glu
    50                  55                  60

Val Val Tyr Leu Asn Asn Thr Thr Ile Glu Lys Glu Ile Cys Ser Val
65                  70                  75                  80

Val Leu Glu Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp His Ser Lys
        115                 120                 125

Cys Tyr Gln Phe Ala Leu Gly Gln Gly Thr Thr Leu Asn Asn Lys His
    130                 135                 140

Ser Asn Ser Thr Ile His Asp Arg Thr Ser His Arg Thr Leu Leu Met
145                 150                 155                 160

Asn Glu Leu Gly Val Pro Phe His Leu Gly Thr Lys Gln Val Cys Ile
                165                 170                 175
```

Ala Trp Ser Ser Ser Cys His Asp Gly Lys Ala Trp Leu His Val
            180                 185                 190

Cys Val Thr Gly Asp Asp Arg Asn Ala Thr Ala Ser Phe Val Tyr Asn
    195                 200                 205

Gly Met Leu Val Asp Ser Ile Gly Ser Trp Ser Arg Asn Ile Leu Arg
210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
            245                 250                 255

Ile Arg Glu Gly Lys Ile Ile His Ile Ser Pro Leu Ser Gly Ser Ala
            260                 265                 270

Gln His Ile Glu Glu Cys Ser Cys Tyr Pro Arg Tyr Pro Asn Val Arg
        275                 280                 285

Cys Val Cys Arg Asp Asn Trp Lys Gly Ser Asn Arg Pro Val Ile Asp
290                 295                 300

Ile Asn Met Ala Asp Tyr Asn Ile Asn Ser Ser Tyr Val Cys Ser Gly
305                 310                 315                 320

Leu Val Gly Asp Thr Pro Arg Asn Asp Asp Ser Ser Ser Ser Ser Asn
                325                 330                 335

Cys Lys Asp Pro Asn Asn Glu Arg Gly Asn Pro Gly Val Lys Gly Trp
            340                 345                 350

Ala Phe Asp Asn Gly Asn Asp Val Trp Met Gly Arg Thr Ile Ser Lys
            355                 360                 365

Asp Leu Arg Ser Gly Tyr Glu Thr Phe Lys Val Ile Gly Gly Trp Thr
370                 375                 380

Thr Ala Asn Ser Lys Ser Gln Val Asn Arg Gln Val Ile Val Asp Asn
385                 390                 395                 400

Asn Asn Trp Ser Gly Tyr Ser Gly Ile Phe Ser Val Glu Gly Lys Ser
                405                 410                 415

Cys Val Asn Arg Cys Phe Tyr Val Glu Leu Ile Arg Gly Gly Pro Gln
            420                 425                 430

Glu Thr Arg Val Trp Trp Thr Ser Asn Ser Ile Val Val Phe Cys Gly
            435                 440                 445

Thr Ser Gly Thr Tyr Gly Thr Gly Ser Trp Pro Asp Gly Ala Asn Ile
450                 455                 460

Asn Phe Met Pro Ile
465

<210> SEQ ID NO 13
<211> LENGTH: 20
<212> TYPE: DNA
<213> ORGANISM: artificial sequence
<220> FEATURE:
<223> OTHER INFORMATION: H3N2 NA FWD primer

<400> SEQUENCE: 13
gggaccacgc tgaacaataa                                          20

<210> SEQ ID NO 14
<211> LENGTH: 20
<212> TYPE: DNA
<213> ORGANISM: artificial sequence
<220> FEATURE:
<223> OTHER INFORMATION: H3N2 NA REV primer

<400> SEQUENCE: 14

-continued tgaaacggaa cacccaactc                                               20

<210> SEQ ID NO 15
<211> LENGTH: 21
<212> TYPE: DNA
<213> ORGANISM: artificial sequence
<220> FEATURE:
<223> OTHER INFORMATION: H3N8 NA FWD primer

<400> SEQUENCE: 15
gttcgccctc agaatgtaga a                                             21

<210> SEQ ID NO 16
<211> LENGTH: 25
<212> TYPE: DNA
<213> ORGANISM: artificial sequence
<220> FEATURE:
<223> OTHER INFORMATION: H3N8 NA REV primer

<400> SEQUENCE: 16
cctatacgga cttcgatcct ttatt                                         25

<210> SEQ ID NO 17
<211> LENGTH: 20
<212> TYPE: DNA
<213> ORGANISM: artificial sequence
<220> FEATURE:
<223> OTHER INFORMATION: Ca.H3N2.HA.390R

<400> SEQUENCE: 17
gaactccaat gtgcctgatg                                               20

<210> SEQ ID NO 18
<211> LENGTH: 22
<212> TYPE: DNA
<213> ORGANISM: artificial sequence
<220> FEATURE:
<223> OTHER INFORMATION: Ca.H3N2.HA.259F

<400> SEQUENCE: 18
ctgcacacta atagatgccc ta                                            22

<210> SEQ ID NO 19
<211> LENGTH: 20
<212> TYPE: DNA
<213> ORGANISM: artificial sequence
<220> FEATURE:
<223> OTHER INFORMATION: Ca.H3N2.HA.743F

<400> SEQUENCE: 19
ccaatctggc agaataagcg                                               20

<210> SEQ ID NO 20
<211> LENGTH: 21
<212> TYPE: DNA
<213> ORGANISM: artificial sequence
<220> FEATURE:
<223> OTHER INFORMATION: Ca.H3N2.HA.1276F

<400> SEQUENCE: 20
gaagggagga ttcaagacct t                                             21

<210> SEQ ID NO 21
<211> LENGTH: 20
<212> TYPE: DNA

<213> ORGANISM: artificial sequence
<220> FEATURE:
<223> OTHER INFORMATION: Ca.H3N2.HA.1569F

<400> SEQUENCE: 21
ggttccagat caaaggtgtt                                          20

<210> SEQ ID NO 22
<211> LENGTH: 21
<212> TYPE: DNA
<213> ORGANISM: artificial sequence
<220> FEATURE:
<223> OTHER INFORMATION: Ca.H3N2.HA.871R

<400> SEQUENCE: 22
cattcggaaa tgcaggtgtc a                                        21

<210> SEQ ID NO 23
<211> LENGTH: 21
<212> TYPE: DNA
<213> ORGANISM: artificial sequence
<220> FEATURE:
<223> OTHER INFORMATION: Ca.H3N2.HA.1408R

<400> SEQUENCE: 23
tcagcatttt ccctcaattg c                                        21

<210> SEQ ID NO 24
<211> LENGTH: 20
<212> TYPE: DNA
<213> ORGANISM: artificial sequence
<220> FEATURE:
<223> OTHER INFORMATION: Ca.H3N2.NA.429F

<400> SEQUENCE: 24
gggaccacgc tgaacaataa                                          20

<210> SEQ ID NO 25
<211> LENGTH: 20
<212> TYPE: DNA
<213> ORGANISM: artificial sequence
<220> FEATURE:
<223> OTHER INFORMATION: Ca.H3N2.NA.484R

<400> SEQUENCE: 25
tgaaacggaa cacccaactc                                          20

<210> SEQ ID NO 26
<211> LENGTH: 20
<212> TYPE: DNA
<213> ORGANISM: artificial sequence
<220> FEATURE:
<223> OTHER INFORMATION: Ca.H3N2.NA.975F

<400> SEQUENCE: 26
tcaggacttg ttggcgatac                                          20

<210> SEQ ID NO 27
<211> LENGTH: 22
<212> TYPE: DNA
<213> ORGANISM: artificial sequence
<220> FEATURE:
<223> OTHER INFORMATION: Ca.H3N2.NA.1023R

<400> SEQUENCE: 27
tcctggattc cctctctcat ta                                       22

<210> SEQ ID NO 28
<211> LENGTH: 24
<212> TYPE: DNA
<213> ORGANISM: artificial sequence
<220> FEATURE:
<223> OTHER INFORMATION: Ca.H3N2.1229F

<400> SEQUENCE: 28
actggtctgg ttattctggt attt                                          24

<210> SEQ ID NO 29
<211> LENGTH: 20
<212> TYPE: DNA
<213> ORGANISM: artificial sequence
<220> FEATURE:
<223> OTHER INFORMATION: Ca.H3N2.1279R

<400> SEQUENCE: 29
tcttgtggcc ctcctcttat                                               20

<210> SEQ ID NO 30
<211> LENGTH: 1695
<212> TYPE: DNA
<213> ORGANISM: artificial sequence
<220> FEATURE:
<223> OTHER INFORMATION: DNA encoding HA protein of H3N8 CIV strain
    A/Ca/CT/85863/11

<400> SEQUENCE: 30
atgaaaacaa ccattatttt aatactactg acccattggg cctacagtca aacccaatc    60 agtggcaata acacagccac actgtgtctg ggacaccatg cagtagcaaa tggaacattg   120
gtaaagacaa tgagtgatga tcaaattgag gtgacaaatg ctacagaatt agttcagagc   180
atttcaatgg ggaaaatatg caacaaatca tatagagttc tagatggaag aaattgcaca   240
ttaatagatg caatgctagg agaccccag tgtgacgcct ttcagtatga gagttgggac   300
ctctttatag aaagaagcaa tgctttcagc aattgctacc catatgacat ccctgactat   360
gcatcgctcc gatccattgt agcatcctca ggaacagtgg aattcacagt agagggattc   420
acatggacag gtgtcactca aaacggaaga agtggagcct gcaaaagggg atcagccgat   480
agtttcttta gccgactgaa ttggctaaca aaatctggaa gctcttaccc cacattgaat   540
gtgacaatgc ctaacaataa aaatttcgac aagctataca tctgggggat tcatcaccg   600 agctcgaatc aagagcagac aaaattgtac atccaagaat caggacgagt aacagtctca    660
acaaaaagaa gtcaacaaac aataatccct cacatcggat ctagaccgtt gatcagaggt   720
caatcaggca ggataagcat atactggacc attgtaaaac ctggagatat cctaatgata    780
aacagtaatg caacttagt tgcaccgcgg ggatatttca attgaaccc aggaaaaagc    840 tctgtaatga atccgatgt acccatagac atttgtgtgt ctgaatgtat tacaccaat     900 ggaagcatct ccaacgacaa gccattccaa aatgtgaaca agttacata tggaaaatgc   960 cccaagtata tcaggcaaaa cactttaaag ttggccactg ggatgaggaa tgtgccagaa  1020
aagcaaacca gaggaatctt tgggcgata gcgggattca tcgaaaacgg ctgggaagga  1080
atggttgatg gtggtggtgg gttccgatat caaaactctg aaggaacagg gcaagctgca  1140
gatctaaaga gcactcaagc agccatcgac cagattaatg gaaagttaaa cagggtgatt  1200
gaaagaacca atgagaaatt ccatcaaata gagaaggaat tctcagaagt agaagaaaga  1260
attcaggact tggagaaata tgtagaagac accaaaatag acctatggtc ctacaatgca  1320

```
gaactgctgg tggctctaga aaatcaacat acaattgact taacagatgc agaaatgaat    1380
aaattatttg agaagactag acgccagtta agagaaaatg cagaagacat gggagatgga    1440
tgtttcaaga tttaccacaa gtgtgataat gcatgcattg aatcaataag aactggaaca    1500
tatgaccatt acatatacag agatgaagca ataaacaacc gatttcagat caaaggtgta    1560
gaattgaaat caggctacaa agattggata ctgtggattt cattcgccat atcatgcttc    1620
ttaatttgcg ttgttctatt gggtttcatt atgtgggctt gccaaaaagg caacatcaga    1680
tgcaacattt gcatt                                                    1695

<210> SEQ ID NO 31
<211> LENGTH: 565
<212> TYPE: PRT
<213> ORGANISM: artificial sequence
<220> FEATURE:
<223> OTHER INFORMATION: HA protein of H3N8 CIV strain A/Ca/CT/85863/11

<400> SEQUENCE: 31

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
            20                  25                  30

His Ala Val Ala Asn Gly Thr Leu Val Lys Thr Met Ser Asp Asp Gln
        35                  40                  45

Ile Glu Val Thr Asn Ala Thr Glu Leu Val Gln Ser Ile Ser Met Gly
    50                  55                  60

Lys Ile Cys Asn Lys Ser Tyr Arg Val Leu Asp Gly Arg Asn Cys Thr
65                  70                  75                  80

Leu Ile Asp Ala Met Leu Gly Asp Pro Gln Cys Asp Ala Phe Gln Tyr
                85                  90                  95

Glu Ser Trp Asp Leu Phe Ile Glu Arg Ser Asn Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Val Glu Phe Thr Val Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
    210                 215                 220

Gln Gln Thr Ile Ile Pro His Ile Gly Ser Arg Pro Leu Ile Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Asn Pro Gly Lys Ser Ser Val Met Arg Ser Asp Val Pro
        275                 280                 285
```

```
Ile Asp Ile Cys Val Ser Glu Cys Ile Thr Pro Asn Gly Ser Ile Ser
    290                 295                 300
Asn Asp Lys Pro Phe Gln Asn Val Asn Lys Val Thr Tyr Gly Lys Cys
305                 310                 315                 320
Pro Lys Tyr Ile Arg Gln Asn Thr Leu Lys Leu Ala Thr Gly Met Arg
                325                 330                 335
Asn Val Pro Glu Lys Gln Thr Arg Gly Ile Phe Gly Ala Ile Ala Gly
            340                 345                 350
Phe Ile Glu Asn Gly Trp Glu Gly Met Val Asp Gly Trp Tyr Gly Phe
        355                 360                 365
Arg Tyr Gln Asn Ser Glu Gly Thr Gly Gln Ala Ala Asp Leu Lys Ser
370                 375                 380
Thr Gln Ala Ala Ile Asp Gln Ile Asn Gly Lys Leu Asn Arg Val Ile
385                 390                 395                 400
Glu Arg Thr Asn Glu Lys Phe His Gln Ile Glu Lys Glu Phe Ser Glu
                405                 410                 415
Val Glu Glu Arg Ile Gln Asp Leu Glu Lys Tyr Val Glu Asp Thr Lys
            420                 425                 430
Ile Asp Leu Trp Ser Tyr Asn Ala Glu Leu Leu Val Ala Leu Glu Asn
        435                 440                 445
Gln His Thr Ile Asp Leu Thr Asp Ala Glu Met Asn Lys Leu Phe Glu
    450                 455                 460
Lys Thr Arg Arg Gln Leu Arg Glu Asn Ala Glu Asp Met Gly Asp Gly
465                 470                 475                 480
Cys Phe Lys Ile Tyr His Lys Cys Asp Asn Ala Cys Ile Glu Ser Ile
                485                 490                 495
Arg Thr Gly Thr Tyr Asp His Tyr Ile Tyr Arg Asp Glu Ala Ile Asn
            500                 505                 510
Asn Arg Phe Gln Ile Lys Gly Val Glu Leu Lys Ser Gly Tyr Lys Asp
        515                 520                 525
Trp Ile Leu Trp Ile Ser Phe Ala Ile Ser Cys Phe Leu Ile Cys Val
    530                 535                 540
Val Leu Leu Gly Phe Ile Met Trp Ala Cys Gln Lys Gly Asn Ile Arg
545                 550                 555                 560
Cys Asn Ile Cys Ile
                565

<210> SEQ ID NO 32
<211> LENGTH: 1410
<212> TYPE: DNA
<213> ORGANISM: artificial sequence
<220> FEATURE:
<223> OTHER INFORMATION: DNA encoding NA protein of H3N8 CIV strain
      A/Ca/CT/85863/11

<400> SEQUENCE: 32
atgaacccaa atcaaaagat aatagcaatt ggatctgcat cattggggat attaatcatt      60
aatatcattc tccatgtagt cagcattata gtaacagtac tggtcctcaa taacaataga     120
acagatctga actgcaaagg gacgatcata agagagtaca tgaaacagt aagagtagaa      180 aaacttactc aatggtacaa catcagtaca accaagtaca tagagagacc ttcaaatgaa     240
tattacatga caacactga accactttgt gaggcccaag ctttgcacc attttccaaa       300 gataatggaa tacgaattgg gtcgagaggc catgttttg tgataagaga accttttgta      360
tcatgttcac cctcagaatg taaacctttt ttcctcacac agggctcatt actcaatgac     420
```

```
aaacattcta acggcacaat aaaggatcga agtccgtata ggactctgat gagtgtcaaa      480 ataggggcaat cacctaatgt atatcaagct aaatttgaat cggtggcatg gtcagcaaca     540
gcatgccatg atggaaaaaa atggatgaca gttggagtca cagggcccga caatcaagca     600
attgcagtag tgaactatgg aggtgttccg gttgatatta ttaattcatg gcaggggat      660 attttaagaa cccaagaatc atcatgcacc tgcattaaag gagactgtta ttgggtaatg     720
actgatggac cggcaaatag gcaagctaat tataggatat caaagcaaa agatggaaga      780 gtaattggac aaactgatat aagtttcaat gggggacaca tagaggagtg ttccttgttac    840 cccaatgaag ggaaggtgga atgcatatgc agagacaatt ggactggaac aaacagacca    900
attctggtaa tatcttctga tctatcgtac acagttggat atttgtgtgc tggcattccc    960
actgacaccc ctaggggaga ggatagtcaa ttcacaggct catgtacaag tcctttggga   1020
aataaaggat acggtgtcaa aggtttcggg tttcgacaag gaactgacgt atgggccgga   1080
aggacaatta gtaggacttc aagatcagga ttcgaaataa taaaaatcag gaatggctgg   1140
acacagaata gtaaggacca aatcaggagg caagtgatta tcgatgaccct aaattggtca   1200 ggatatagcg gttcttttcac attgccggtt gaattaacaa aaaaaggatg tttggtcccc   1260
tgtttctggg ttgaaatgat tagaggtaaa cctgaagaaa caacaatatg gacctctagc   1320
agctccattg tgatgtgtgg agtagatcat aaaattgcca gttggtcatg gcacgatgga   1380
gcaattcttc cctttgacat cgataagatg                                     1410
```

<210> SEQ ID NO 33
<211> LENGTH: 470
<212> TYPE: PRT
<213> ORGANISM: artificial sequence
<220> FEATURE:
<223> OTHER INFORMATION: NA protein of H3N8 CIV strain A/Ca/CT/85863/11

<400> SEQUENCE: 33

```
Met Asn Pro Asn Gln Lys Ile Ile Ala Ile Gly Ser Ala Ser Leu Gly
1               5                   10                  15

Ile Leu Ile Ile Asn Ile Ile Leu His Val Val Ser Ile Ile Val Thr
            20                  25                  30

Val Leu Val Leu Asn Asn Asn Arg Thr Asp Leu Asn Cys Lys Gly Thr
        35                  40                  45

Ile Ile Arg Glu Tyr Asn Glu Thr Val Arg Val Glu Lys Leu Thr Gln
    50                  55                  60

Trp Tyr Asn Ile Ser Thr Thr Lys Tyr Ile Glu Arg Pro Ser Asn Glu
65                  70                  75                  80

Tyr Tyr Met Asn Asn Thr Glu Pro Leu Cys Glu Ala Gln Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Glu Cys Arg
        115                 120                 125

Thr Phe Phe Leu Thr Gln Gly Ser Leu Leu Asn Asp Lys His Ser Asn
    130                 135                 140

Gly Thr Ile Lys Asp Arg Ser Pro Tyr Arg Thr Leu Met Ser Val Lys
145                 150                 155                 160

Ile Gly Gln Ser Pro Asn Val Tyr Gln Ala Lys Phe Glu Ser Val Ala
                165                 170                 175

Trp Ser Ala Thr Ala Cys His Asp Gly Lys Lys Trp Met Thr Val Gly
            180                 185                 190
```

Val Thr Gly Pro Asp Asn Gln Ala Ile Ala Val Val Asn Tyr Gly Gly
            195                 200                 205

Val Pro Val Asp Ile Ile Asn Ser Trp Ala Gly Asp Ile Leu Arg Thr
    210                 215                 220

Gln Glu Ser Ser Cys Thr Cys Ile Lys Gly Asp Cys Tyr Trp Val Met
225                 230                 235                 240

Thr Asp Gly Pro Ala Asn Arg Gln Ala Asn Tyr Arg Ile Phe Lys Ala
                245                 250                 255

Lys Asp Gly Arg Val Ile Gly Gln Thr Asp Ile Ser Phe Asn Gly Gly
            260                 265                 270

His Ile Glu Glu Cys Ser Cys Tyr Pro Asn Glu Gly Lys Val Glu Cys
        275                 280                 285

Ile Cys Arg Asp Asn Trp Thr Gly Thr Asn Arg Pro Ile Leu Val Ile
    290                 295                 300

Ser Ser Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
                325                 330                 335

Ser Pro Leu Gly Asn Lys Gly Tyr Gly Val Lys Gly Phe Gly Phe Arg
            340                 345                 350

Gln Gly Thr Asp Val Trp Ala Gly Arg Thr Ile Ser Arg Thr Ser Arg
        355                 360                 365

Ser Gly Phe Glu Ile Ile Lys Ile Arg Asn Gly Trp Thr Gln Asn Ser
    370                 375                 380

Lys Asp Gln Ile Arg Arg Gln Val Ile Ile Asp Leu Asn Trp Ser
385                 390                 395                 400

Gly Tyr Ser Gly Ser Phe Thr Leu Pro Val Glu Leu Thr Lys Lys Gly
                405                 410                 415

Cys Leu Val Pro Cys Phe Trp Val Glu Met Ile Arg Gly Lys Pro Glu
            420                 425                 430

Glu Thr Thr Ile Trp Thr Ser Ser Ser Ile Val Met Cys Gly Val
        435                 440                 445

Asp His Lys Ile Ala Ser Trp Ser Trp His Asp Gly Ala Ile Leu Pro
    450                 455                 460

Phe Asp Ile Asp Lys Met
465                 470

<210> SEQ ID NO 34
<211> LENGTH: 1695
<212> TYPE: DNA
<213> ORGANISM: artificial sequence
<220> FEATURE:
<223> OTHER INFORMATION: DNA encoding HA protein of H3N8 CIV strain
      A/canine/NY/120106.2/2011

<400> SEQUENCE: 34
atgaaaacaa ccattatttt aatactactg acccattggg cctacagtca aacccaatc      60 agtggcaata acacagccac actgtgtctg ggacaccatg cagtagcaaa tggaacattg     120
gtaaagacaa tgagtgatga tcaaattgag gtgacaaatg ttacagaatt agttcagagc     180
atttcaatgg ggaaaatatg caacaaatca tatagagttc tagatggaag aaattgcaca     240
ttaatagatg caatgctagg agaccccag tgtgacgcct ttcagtatga gagttgggac     300
ctctttatag aaagaagcaa cgctttcagc aattgctacc catatgacat ccctgactat     360
gcatcgctcc gatccattgt agcatcctca ggaacagtgg aattcacagc agagggattc     420

-continued

```
acatggacag gtgtcactca aaacggaaga agtggagcct gcaaaagggg atcagccgat    480
agtttcttta gccgactgaa ttggctaaca aaatctggaa gctcttaccc cacattgaat    540
gtaacaatgc ctaacaatga aaatttcgac aagctataca tctgggggat tcatcacccg    600
agctcgaatc aagagcagac aaaattgtac attcaagaat caggacgagt aacagtctca    660
acaaaaagaa gtcaacaaac aataattcct cacatcggat ctagaccgtt gatcagaggt    720
caatcaggca ggataagcat atactggacc attgtaaaac ctggagatat cctaatgata    780
aacagtaatg gcaacttagt tgcaccgcgg ggatatttca aattgaaccc aggaaaaagc    840
tctgtaatta gatccgatgt acccatagac atttgtgtgt ctgaatgtat tacaccaaat    900
ggaagcatct ccaacgacaa gccattccaa aatgtgaaca aagttacata tggaaaatgc    960
cccaagtata tcaggcaaaa cactttaaag ttggccactg ggatgaggaa tgtgccagaa   1020
aagcaaacca gaggaatctt tggggcgata gcgggattca tcgaaaacgg ctgggaagga   1080
atggttgatg ggtggtatgg gttccgatat caaaactctg aaggaacagg gcaagctgca   1140
gatctaaaga gcactcaagc agccatcgac cagattaatg gaaagttaaa cagggtgatt   1200
gaaagaacca atgagaaatt ccatcaaata gagaaggaat tctcagaagt agaaggaaga   1260
attcaggact tggagaaata tgtagaagac accaaaatag acctatggtc ctacaatgca   1320
gaactactgg tggctctaga aaatcaacat acaattgact taacagatgc agaaatgaat   1380
aaattatttg agaagactag acgccagtta agagaaaatg cagaagacat gggaaatgga   1440
tgtttcaaga tttaccacaa gtgtgataat gcatgcattg agtcaataag aactggaaca   1500
tatgaccatt acatatacag agatgaagca ataaacaacc gatttcagat caaaggtgta   1560
gaattgaaat caggctacaa agattggata ctgtggattt cattcgccat atcatgcttc   1620
ttaatttgcg ttgttctatt gggtttcatt atgtgggctt gccaaaaagg caacatcaga   1680
tgcaacattt gcatt                                                    1695
```

```
<210> SEQ ID NO 35
<211> LENGTH: 565
<212> TYPE: PRT
<213> ORGANISM: artificial sequence
<220> FEATURE:
<223> OTHER INFORMATION: HA protein of H3N8 CIV strain
      A/canine/NY/120106.2/2011

<400> SEQUENCE: 35

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
            20                  25                  30

His Ala Val Ala Asn Gly Thr Leu Val Lys Thr Met Ser Asp Asp Gln
        35                  40                  45

Ile Glu Val Thr Asn Val Thr Glu Leu Val Gln Ser Ile Ser Met Gly
    50                  55                  60

Lys Ile Cys Asn Lys Ser Tyr Arg Val Leu Asp Gly Arg Asn Cys Thr
65                  70                  75                  80

Leu Ile Asp Ala Met Leu Gly Asp Pro Gln Cys Asp Ala Phe Gln Tyr
                85                  90                  95

Glu Ser Trp Asp Leu Phe Ile Glu Arg Ser Asn Ala Phe Ser Asn Cys
            100                 105                 110

Tyr Pro Tyr Asp Ile Pro Asp Tyr Ala Ser Leu Arg Ser Ile Val Ala
        115                 120                 125
```

```
Ser Ser Gly Thr Val Glu Phe Thr Ala Glu Gly Phe Thr Trp Thr Gly
130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Glu Asn Phe Asp Lys Leu
                180                 185                 190

Tyr Ile Trp Gly Ile His His Pro Ser Ser Asn Gln Glu Gln Thr Lys
            195                 200                 205

Leu Tyr Ile Gln Glu Ser Gly Arg Val Thr Val Ser Thr Lys Arg Ser
210                 215                 220

Gln Gln Thr Ile Ile Pro His Ile Gly Ser Arg Pro Leu Ile Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Asn Pro Gly Lys Ser Ser Val Ile Arg Ser Asp Val Pro
        275                 280                 285

Ile Asp Ile Cys Val Ser Glu Cys Ile Thr Pro Asn Gly Ser Ile Ser
290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Thr Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ala Glu Met Asn Lys Leu Phe Glu
450                 455                 460

Lys Thr Arg Arg Gln Leu Arg Glu Asn Ala Glu Asp Met Gly Asn Gly
465                 470                 475                 480

Cys Phe Lys Ile Tyr His Lys Cys Asp Asn Ala Cys Ile Glu Ser Ile
                485                 490                 495

Arg Thr Gly Thr Tyr Asp His Tyr Ile Tyr Arg Asp Glu Ala Ile Asn
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Ile Cys Val
530                 535                 540
```

Val Leu Leu Gly Phe Ile Met Trp Ala Cys Gln Lys Gly Asn Ile Arg
545                 550                 555                 560

Cys Asn Ile Cys Ile
            565

<210> SEQ ID NO 36
<211> LENGTH: 1410
<212> TYPE: DNA
<213> ORGANISM: artificial sequence
<220> FEATURE:
<223> OTHER INFORMATION: DNA encoding NA protein of H3N8 CIV strain
      A/canine/NY/120106.2/2011

<400> SEQUENCE: 36

```
atgaatccaa atcaaaagat aatagcaatt ggatctgcat cattggggat attaatcatt      60
aatatcattc tccatgtagt cagcattata gtaacagtac tggtcctcaa taacaataga     120
acagatctga actgcaaagg gacgatcata agagagtaca atgaaacagt aagagtagaa     180
aaacttactc aatggtataa tatcagtaca attaagtaca tagagagacc ttcaaatgaa     240
tattacatga caacactga accactttgt gaggcccaag gctttgcacc attttccaaa     300
gataatggaa tacgaattgg gtcgagaggc catgttttg tgataagaga acctttgta     360
tcatgttcac cctcagaatg tagaacctt ttcctcacac agggctcatt actcaatgac     420
aaacattcta acggcacaat aaaggatcga agtccgtata ggactctgat gagtgtcaaa     480
ataggcaat cacctaatgt atatcaagct aaatttgaat cggtggcatg gtcagcaaca     540
gcatgccatg atggaaaaaa atggatgaca gttggagtca cagggcccga caatcaagca     600
attgcagtag tgaactatgg aggtgttccg gttgatatta ttaattcatg ggcaggggat     660
attttaagaa cccaagaatc atcatgcacc tgcattaaag agactgttta ttgggtaatg     720
actgatggac cggcaaatag gcaagctaat tataggatat caaagcaaa agatggaaga     780
gtaattggac aaactgatat aagtttcaat ggggacaca tagaggagtg ttcttgttac     840
cccaatgaag ggaaggtgga atgcatatgc agagacaatt ggactggaac aaacagacca     900
attctggtaa tatcttctga tctatcgtac acagttggat atttgtgtgc tggcattccc     960
actgacaccc ctagggagaa ggatagtcaa ttcacaggct catgtacaag tcctttggga    1020
aataaaggat acgtgtcaa aggtttcggg tttcgacaag aactgacgt atgggccgga    1080
aggacaatta gtaggacttc aagatcagga ttcgaaataa taaaaatcag gaatggttgg    1140
acacagaata gtaaggacca aatcaggagg caagtgatta tcgatgaccc aaaattggtca    1200
ggatatagcg gttcttcac attgccggtt gaattaacaa aaaaggatg tttggtcccc    1260
tgtttctggg ttgaaatgat tagaggtaaa cctgaagaaa caacaatatg gacctctagc    1320
agctccattg tgatgtgtgg agtagatcat aaaattgcca gttggtcatg cacgatgga    1380
gcaattcttc cctttgacat cgataagatg                                     1410
```

<210> SEQ ID NO 37
<211> LENGTH: 470
<212> TYPE: PRT
<213> ORGANISM: artificial sequence
<220> FEATURE:
<223> OTHER INFORMATION: NA protein of H3N8 CIV strain
      A/canine/NY/120106.2/2011

<400> SEQUENCE: 37

Met Asn Pro Asn Gln Lys Ile Ile Ala Ile Gly Ser Ala Ser Leu Gly
1               5                   10                  15

-continued

```
Ile Leu Ile Ile Asn Ile Ile Leu His Val Val Ser Ile Ile Val Thr
            20                  25                  30

Val Leu Val Leu Asn Asn Asn Arg Thr Asp Leu Asn Cys Lys Gly Thr
            35                  40                  45

Ile Ile Arg Glu Tyr Asn Glu Thr Val Arg Val Glu Lys Leu Thr Gln
            50                  55                  60

Trp Tyr Asn Ile Ser Thr Ile Lys Tyr Ile Glu Arg Pro Ser Asn Glu
65                  70                  75                  80

Tyr Tyr Met Asn Asn Thr Glu Pro Leu Cys Glu Ala Gln Gly Phe Ala
            85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Ser Glu Cys Arg
            115                 120                 125

Thr Phe Phe Leu Thr Gln Gly Ser Leu Leu Asn Asp Lys His Ser Asn
            130                 135                 140

Gly Thr Ile Lys Asp Arg Ser Pro Tyr Arg Thr Leu Met Ser Val Lys
145                 150                 155                 160

Ile Gly Gln Ser Pro Asn Val Tyr Gln Ala Lys Phe Glu Ser Val Ala
            165                 170                 175

Trp Ser Ala Thr Ala Cys His Asp Gly Lys Lys Trp Met Thr Val Gly
            180                 185                 190

Val Thr Gly Pro Asp Asn Gln Ala Ile Ala Val Val Asn Tyr Gly Gly
            195                 200                 205

Val Pro Val Asp Ile Ile Asn Ser Trp Ala Gly Asp Ile Leu Arg Thr
210                 215                 220

Gln Glu Ser Ser Cys Thr Cys Ile Lys Gly Asp Cys Tyr Trp Val Met
225                 230                 235                 240

Thr Asp Gly Pro Ala Asn Arg Gln Ala Asn Tyr Arg Ile Phe Lys Ala
            245                 250                 255

Lys Asp Gly Arg Val Ile Gly Gln Thr Asp Ile Ser Phe Asn Gly Gly
            260                 265                 270

His Ile Glu Glu Cys Ser Cys Tyr Pro Asn Glu Gly Lys Val Glu Cys
            275                 280                 285

Ile Cys Arg Asp Asn Trp Thr Gly Thr Asn Arg Pro Ile Leu Val Ile
            290                 295                 300

Ser Ser Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
            325                 330                 335

Ser Pro Leu Gly Asn Lys Gly Tyr Gly Val Lys Gly Phe Gly Phe Arg
            340                 345                 350

Gln Gly Thr Asp Val Trp Ala Gly Arg Thr Ile Ser Arg Thr Ser Arg
            355                 360                 365

Ser Gly Phe Glu Ile Ile Lys Ile Arg Asn Gly Trp Thr Gln Asn Ser
            370                 375                 380

Lys Asp Gln Ile Arg Arg Gln Val Ile Asp Asp Pro Asn Trp Ser
385                 390                 395                 400

Gly Tyr Ser Gly Ser Phe Thr Leu Pro Val Glu Leu Thr Lys Lys Gly
            405                 410                 415

Cys Leu Val Pro Cys Phe Trp Val Glu Met Ile Arg Gly Lys Pro Glu
            420                 425                 430

Glu Thr Thr Ile Trp Thr Ser Ser Ser Ser Ile Val Met Cys Gly Val
```

```
                435                 440                 445
Asp His Lys Ile Ala Ser Trp Ser Trp His Asp Gly Ala Ile Leu Pro
    450                 455                 460

Phe Asp Ile Asp Lys Met
465                 470

<210> SEQ ID NO 38
<211> LENGTH: 1695
<212> TYPE: DNA
<213> ORGANISM: artificial sequence
<220> FEATURE:
<223> OTHER INFORMATION: DNA encoding HA protein of H3N8 CIV strain
      WY/86033/07

<400> SEQUENCE: 38
atgaagacaa ccattatttt aatactactg acccattggg cccacagtca aacccaatc        60 agtggcaata acacagccac actgtgtctg ggacaccatg cagtagcaaa tggaacatta       120
gtaaaaacaa tgagtgatga tcaaattgag gtgacaaatg ctacagaatt agttcagagc       180
atttcaatgg ggaaaatatg caacaaatca tatagaattc tagatggaag aaattgcaca       240
ttaatagatg caatgctagg agaccccac tgtgacgcct ttcagtatga gagttgggac        300
ctctttatag aaagaagcaa cgctttcagc aattgctacc catatgacat ccctgactat      360
gcatcgctcc gatccattgt agcatcctca ggaacagtga attcacagc agagggattc       420 acatggacag gtgtcactca aaacggaaga agtggagcct gcaaagggg atcagccgat       480 agtttcttta gccgactgaa ttggctaaca aaatctggaa gctcttaccc cacattgaat       540
gtgacaatgc ctaacaataa aaatttcgac aagctataca tctggggat tcatcaccca      600 agctcaaatc aagagcagac aaaattgtac atccaagaat caggacgagt aacagtctca      660
acaaaaagaa gtcaacaaac aataatccct aacatcggat ctagaccgtt ggtcagaggt      720
caatcaggca ggataagcat atactggacc attgtaaaac ctggagatat cctaatgata      780
aacagtaatg caacttagt tgcaccgcgg ggatatttta aactgaacac agggaaaagc       840
tctgtaatga atccgatgt acccatagac atttgtgtgt ctgaatgtat tacaccaaat      900
ggaagcatct ccaacgacaa gccattccaa atgtgaaca aagttacata tggaaaatgc        960
cccaagtata tcaggcaaaa cactttaaag ctggccactg ggatgaggaa tgtaccagaa     1020
aagcaaacca gaggaatctt tggagcaata gcgggattca tcgaaaacgg ctgggaagga     1080
atggttgatg gtggtatgg gttccgatat caaaactctg aaggaacagg caagctgca       1140 gatctaaaga gcactcaagc agccatcgac cagattaatg aaagttaaa cagagtgatt     1200 gaaagaacca atgagaaatt ccatcaaata gagaaggaat tctcagaagt agaaggaaga     1260
attcaggact ggagaaata tgtagaagac accaaaatag acctatggtc ctacaatgca     1320
gaattgctgg tggctctaga aaatcaacat acaattgact aacagatgc aaaaatgaat       1380 aaattatttg agaagactag acgccagttg agagaaaacg cagaagacat gggaggtgga     1440
tgtttcaaga tttatcacaa atgtgataat gcatgcattg aatcaataag aactggaaca     1500
tatgaccatt acatatacag agatgaagca ttaaacaacc gatttcagat caaaggtgta     1560
gagttgaaat caggctacaa agattggata ctgtggatt cattcgccat atcatgcttc     1620
ttaatttgcg ttgttctatt gggtttcatt atgtgggctt gccaaaaagg caacatcaga     1680
tgcaacattt gcatt                                                     1695

<210> SEQ ID NO 39
```

```
<211> LENGTH: 565
<212> TYPE: PRT
<213> ORGANISM: artificial sequence
<220> FEATURE:
<223> OTHER INFORMATION: HA protein of H3N8 CIV strain WY/86033/07

<400> SEQUENCE: 39

Met Lys Thr Thr Ile Ile Leu Ile Leu Leu Thr His Trp Ala His Ser
1               5                   10                  15

Gln Asn Pro Ile Ser Gly Asn Asn Thr Ala Thr Leu Cys Leu Gly His
            20                  25                  30

His Ala Val Ala Asn Gly Thr Leu Val Lys Thr Met Ser Asp Asp Gln
        35                  40                  45

Ile Glu Val Thr Asn Ala Thr Glu Leu Val Gln Ser Ile Ser Met Gly
    50                  55                  60

Lys Ile Cys Asn Lys Ser Tyr Arg Ile Leu Asp Gly Arg Asn Cys Thr
65                  70                  75                  80

Leu Ile Asp Ala Met Leu Gly Asp Pro His Cys Asp Ala Phe Gln Tyr
                85                  90                  95

Glu Ser Trp Asp Leu Phe Ile Glu Arg Ser Asn Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Val Lys Phe Thr Ala Glu Gly Phe Thr Trp Thr Gly
130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
210                 215                 220

Gln Gln Thr Ile Ile Pro Asn Ile Gly Ser Arg Pro Leu Val Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Asn Thr Gly Lys Ser Ser Val Met Arg Ser Asp Val Pro
        275                 280                 285

Ile Asp Ile Cys Val Ser Glu Cys Ile Thr Pro Asn Gly Ser Ile Ser
290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Thr Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
370                 375                 380
```

| | | | | | | | | | | | | | | |
|---|---|---|---|---|---|---|---|---|---|---|---|---|---|---|
Thr | Gln | Ala | Ala | Ile | Asp | Gln | Ile | Asn | Gly | Lys | Leu | Asn | Arg | Val | Ile
385 | | | | | 390 | | | | 395 | | | | | 400

Glu Arg Thr Asn Glu Lys Phe His Gln Ile Glu Lys Glu Phe Ser Glu
              405                 410                 415

Val Glu Gly Arg Ile Gln Asp Leu Glu Lys Tyr Val Glu Asp Thr Lys
          420                 425                 430

Ile Asp Leu Trp Ser Tyr Asn Ala Glu Leu Leu Val Ala Leu Glu Asn
      435                 440                 445

Gln His Thr Ile Asp Leu Thr Asp Ala Lys Met Asn Lys Leu Phe Glu
  450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Glu Ser Ile
              485                 490                 495

Arg Thr Gly Thr Tyr Asp His Tyr Ile Tyr Arg Asp Glu Ala Leu Asn
          500                 505                 510

Asn Arg Phe Gln Ile Lys Gly Val Glu Leu Lys Ser Gly Tyr Lys Asp
      515                 520                 525

Trp Ile Leu Trp Ile Ser Phe Ala Ile Ser Cys Phe Leu Ile Cys Val
  530                 535                 540

Val Leu Leu Gly Phe Ile Met Trp Ala Cys Gln Lys Gly Asn Ile Arg
545                 550                 555                 560

Cys Asn Ile Cys Ile
              565

<210> SEQ ID NO 40
<211> LENGTH: 1410
<212> TYPE: DNA
<213> ORGANISM: artificial sequence
<220> FEATURE:
<223> OTHER INFORMATION: DNA encoding NA protein of H3N8 CIV strain
      WY/86033/07

<400> SEQUENCE: 40
atgaatccaa atcaaaagat aatagcaatt ggatttgcat cattggggat attaatcatt      60
aatgtcattc tccatgtagt cagcattata gtaacagtac tggtcctcaa taacaataga     120
acagatctga actacaaagg gacgatcata agagaataca tgaaacagt aagagtagaa     180
aaacttactc aatggtataa taccagtaca attaagtaca tagagagacc ttcaaatgaa     240
tactacatga ataacactga accactttgt gaggcccaag ctttgcacc atttccaaa      300
gataatggaa tacgaattgg gtcgagaggc catgttttg tgataagaga accttttgta     360
tcatgttcgc cctcagaatg tagaacctttt ttcctcacac agggctcatt actcaatgac     420
aaacattcta acggcacaat aaaggatcga agtccgtata ggactttgat gagtgtcaaa     480
ataggggcaat cacctaatgt atatcaagct agatttgaat cggtggcatg gtcagcaaca     540
gcatgccatg atggaaaaaa atggatgaca gttggagtca caggccccga caatcaagca     600
attgcagtag tgaactatgg aggtgttccg gttgatatta ttaattcatg gcagggggat     660
attttaagaa cccaagagtc atcatgcacc tgcattaaag agactgttta ttgggtaatg     720
actgatggac cggcaaatag gcaagctgaa tataggatat caaagcaaa agatggaaga     780
gtaattgggc aaactgatat aagtttcaat gggggacaca tagaggagtg ttcttgttac     840
cccaatgaag gaaggtgga atgcatatgc aggacaattt ggactggaac aaatagacca     900
attctggtaa tatcttctga tctatcgtac acagttggat atttgtgtgc tggcattccc     960

-continued

```
actgacactc ctaggggaga ggatagtcaa ttcacaggct catgtacaag tcctttggga    1020
aataagggat acggtgtaaa aggcttcggg tttcgacaag gaactgacgt atgggccgga    1080
aggacaatta gtagaacttc aagatcagga ttcgaaataa taaaaatcag gaatggttgg    1140
acacagaaca gtaaggacca aatcaggagg caagtgatta tcgatgaccc aaattggtca    1200
ggatatagcg gttctttcac attgccggtt gaactgacaa aaaagggatg tttggtcccc    1260
tgtttctggg ttgaaatgat tagaggtaaa cctgaagaaa caacaatatg gacctctagc    1320
agctccattg tgatgtgtgg agtagatcat aaaaattgcca gttggtcatg gcacgatgga    1380
gctattcttc cctttgacat cgataagatg                                    1410
```

<210> SEQ ID NO 41
<211> LENGTH: 470
<212> TYPE: PRT
<213> ORGANISM: artificial sequence
<220> FEATURE:
<223> OTHER INFORMATION: NA protein of H3N8 CIV strain WY/86033/07

<400> SEQUENCE: 41

```
Met Asn Pro Asn Gln Lys Ile Ile Ala Ile Gly Phe Ala Ser Leu Gly
1               5                   10                  15

Ile Leu Ile Ile Asn Val Ile Leu His Val Val Ser Ile Ile Val Thr
            20                  25                  30

Val Leu Val Leu Asn Asn Asn Arg Thr Asp Leu Asn Tyr Lys Gly Thr
        35                  40                  45

Ile Ile Arg Glu Tyr Asn Glu Thr Val Arg Val Glu Lys Leu Thr Gln
    50                  55                  60

Trp Tyr Asn Thr Ser Thr Ile Lys Tyr Ile Glu Arg Pro Ser Asn Glu
65                  70                  75                  80

Tyr Tyr Met Asn Asn Thr Glu Pro Leu Cys Glu Ala Gln Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Ser Glu Cys Arg
        115                 120                 125

Thr Phe Phe Leu Thr Gln Gly Ser Leu Leu Asn Asp Lys His Ser Asn
    130                 135                 140

Gly Thr Ile Lys Asp Arg Ser Pro Tyr Arg Thr Leu Met Ser Val Lys
145                 150                 155                 160

Ile Gly Gln Ser Pro Asn Val Tyr Gln Ala Arg Phe Glu Ser Val Ala
                165                 170                 175

Trp Ser Ala Thr Ala Cys His Asp Gly Lys Lys Trp Met Thr Val Gly
            180                 185                 190

Val Thr Gly Pro Asp Asn Gln Ala Ile Ala Val Val Asn Tyr Gly Gly
        195                 200                 205

Val Pro Val Asp Ile Ile Asn Ser Trp Ala Gly Asp Ile Leu Arg Thr
    210                 215                 220

Gln Glu Ser Ser Cys Thr Cys Ile Lys Gly Asp Cys Tyr Trp Val Met
225                 230                 235                 240

Thr Asp Gly Pro Ala Asn Arg Gln Ala Glu Tyr Arg Ile Phe Lys Ala
                245                 250                 255

Lys Asp Gly Arg Val Ile Gly Gln Thr Asp Ile Ser Phe Asn Gly Gly
            260                 265                 270

His Ile Glu Glu Cys Ser Cys Tyr Pro Asn Glu Gly Lys Val Glu Cys
```

```
                275                 280                 285
Ile Cys Arg Asp Asn Trp Thr Gly Thr Asn Arg Pro Ile Leu Val Ile
            290                 295                 300
Ser Ser Asp Leu Ser Tyr Thr Val Gly Tyr Leu Cys Ala Gly Ile Pro
305                 310                 315                 320
Thr Asp Thr Pro Arg Gly Glu Asp Ser Gln Phe Thr Gly Ser Cys Thr
                325                 330                 335
Ser Pro Leu Gly Asn Lys Gly Tyr Gly Val Lys Gly Phe Gly Phe Arg
            340                 345                 350
Gln Gly Thr Asp Val Trp Ala Gly Arg Thr Ile Ser Arg Thr Ser Arg
                355                 360                 365
Ser Gly Phe Glu Ile Ile Lys Ile Arg Asn Gly Trp Thr Gln Asn Ser
            370                 375                 380
Lys Asp Gln Ile Arg Arg Gln Val Ile Ile Asp Asp Pro Asn Trp Ser
385                 390                 395                 400
Gly Tyr Ser Gly Ser Phe Thr Leu Pro Val Glu Leu Thr Lys Lys Gly
                405                 410                 415
Cys Leu Val Pro Cys Phe Trp Val Glu Met Ile Arg Gly Lys Pro Glu
            420                 425                 430
Glu Thr Thr Ile Trp Thr Ser Ser Ser Ile Val Met Cys Gly Val
                435                 440                 445
Asp His Lys Ile Ala Ser Trp Ser Trp His Asp Gly Ala Ile Leu Pro
450                 455                 460
Phe Asp Ile Asp Lys Met
465                 470
```

<210> SEQ ID NO 42
<211> LENGTH: 1410
<212> TYPE: DNA
<213> ORGANISM: artificial sequence
<220> FEATURE:
<223> OTHER INFORMATION: DNA encoding NA protein of H3N8 CIV strain
      A/canine/NY/120106

<400> SEQUENCE: 42

```
atgaacccaa tcaaaagat  aatagcaatt ggatctgcat cattggggat attaatcatt    60
aatatcattc tccatgtagt cagcattata gtaacagtac tggtcctcaa taacaataga   120
acagatctga actgcaaagg gacgatcata agagagtaca tgaaacagt  aagagtagaa   180
aaacttactc aatggtataa tatcagtaca attaagtaca tagagagacc ttcaaatgaa   240
tattacatga caacactga  accactttgt gaggcccaag gctttgcacc attttccaaa   300
gataatggaa tacgaattgg gtcgagaggc catgtttttg tgataagaga acctttgta   360
tcatgttcac cctcagaatg tagaaccttt ttcctcacac agggctcatt actcaatgac   420
aaacattcta acggcacaat aaaggatcga agtccgtata ggactctgat gagtgtcaaa   480
atagggcaat cacctaatgt atatcaagct aaatttgaat cggtggcatg gtcagcaaca   540
gcatgccatg atggaaaaaa atggatgaca gttggagtca gggcccga   caatcaagca   600
attgcagtag tgaactatgg aggtgttccg gttgatatta ttaattcatg gcaggggat    660
atttaagaa  cccaagaatc atcatgcacc tgcattaaag agactgtta  ttgggtaatg   720
actgatggac cggcaaatag gcaagctaat tataggatat caaagcaaa  agatggaaga   780
gtaattggac aaactgatat aagtttcaat ggggacaca  tagaggagtg ttcttgttac   840
cccaatgaag ggaaggtgga atgcatatgc agagacaatt ggactggaac aaacagacca   900
```

```
attctggtaa tatcttctga tctatcgtac acagttggat atttgtgtgc tggcattccc    960
actgacaccc ctaggggaga ggatagtcaa ttcacaggct catgtacaag tcctttggga   1020
aataaaggat acggtgtcaa aggtttcggg tttcgacaag gaactgacgt atgggccgga   1080
aggacaatta gtaggacttc aagatcagga ttcgaaataa taaaaatcag gaatggttgg   1140
acacagaata gtaaggacca aatcaggagg caagtgatta tcgatgaccc aaattggtca   1200
ggatatagcg gttctttcac attgccggtt gaattaacaa aaaaaggatg tttggtcccc   1260
tgtttctggg ttgaaatgat tagaggtaaa cctgaagaaa caacaatatg gacctctagc   1320
agctccattg tgatgtgtgg agtagatcat aaaattgcca gttggtcatg gcacgatgga   1380
gcaattcttc cctttgacat cgataagatg                                    1410
```